United States Patent
Bright et al.

(10) Patent No.: US 11,246,879 B2
(45) Date of Patent: Feb. 15, 2022

(54) METHODS, AGENTS, AND DEVICES FOR LOCAL NEUROMODULATION OF AUTONOMIC NERVES

(71) Applicant: Tulavi Therapeutics, Inc., Los Altos Hills, CA (US)

(72) Inventors: Corinne Bright, Los Altos Hills, CA (US); Kondapavulur T. Venkateswara-Rao, San Jose, CA (US); Emily Stein, San Jose, CA (US)

(73) Assignee: Tulai Therapeutics, Inc., Los Altos Hills, CA (US)

( * ) Notice: Subject to any disclaimer, the term of this patent is extended or adjusted under 35 U.S.C. 154(b) by 0 days.

(21) Appl. No.: 16/076,308

(22) PCT Filed: Feb. 9, 2017

(86) PCT No.: PCT/US2017/017223
§ 371 (c)(1),
(2) Date: Aug. 7, 2018

(87) PCT Pub. No.: WO2017/139487
PCT Pub. Date: Aug. 17, 2017

(65) Prior Publication Data
US 2019/0038646 A1 Feb. 7, 2019

Related U.S. Application Data

(60) Provisional application No. 62/293,327, filed on Feb. 9, 2016.

(51) Int. Cl.
*A61K 31/704* (2006.01)
*A61K 31/445* (2006.01)
*A61N 1/36* (2006.01)

(52) U.S. Cl.
CPC .......... *A61K 31/704* (2013.01); *A61K 31/445* (2013.01); *A61N 1/36114* (2013.01)

(58) Field of Classification Search
CPC . A61K 31/704; A61K 31/445; A61N 1/36114
See application file for complete search history.

(56) References Cited

U.S. PATENT DOCUMENTS

| | | | |
|---|---|---|---|
| 2,339,482 A | 1/1944 | Huttkay | |
| 2,339,846 A | 1/1944 | Du Bois et al. | |
| 4,029,793 A | 6/1977 | Adams et al. | |
| 4,582,865 A | 4/1986 | Balazs et al. | |
| 4,601,169 A | 7/1986 | Hesse et al. | |
| 5,279,825 A | 1/1994 | Wehling | |
| 6,152,943 A | 11/2000 | Sawhney | |
| 6,165,201 A | 12/2000 | Sawhney et al. | |
| 6,179,862 B1 | 1/2001 | Sawhney | |
| 6,379,373 B1 | 4/2002 | Sawhney et al. | |
| 6,514,534 B1 | 2/2003 | Sawhney | |
| 6,545,067 B1 | 4/2003 | Büchner et al. | |
| 6,566,406 B1 | 5/2003 | Pathak et al. | |
| 6,605,294 B2 | 8/2003 | Sawhney | |
| 6,610,713 B2 | 8/2003 | Tracey | |
| 6,629,969 B2 | 10/2003 | Chan et al. | |
| 6,632,457 B1 | 10/2003 | Sawhney | |
| 6,673,093 B1 | 1/2004 | Sawhney | |
| 6,676,675 B2 | 1/2004 | Mallapragada et al. | |
| 6,689,148 B2 | 2/2004 | Sawhney et al. | |
| 6,703,047 B2 | 3/2004 | Sawhney et al. | |
| 6,746,464 B1 | 6/2004 | Makower | |
| 6,818,018 B1 | 11/2004 | Sawhney | |
| 6,887,974 B2 | 5/2005 | Pathak | |
| 6,932,971 B2 | 8/2005 | Bachmann et al. | |
| 6,937,896 B1 | 8/2005 | Kroll | |
| 7,009,034 B2 | 3/2006 | Pathak et al. | |
| 7,025,990 B2 | 4/2006 | Sawhney | |
| 7,057,019 B2 | 6/2006 | Pathak | |
| 7,211,651 B2 | 5/2007 | Pathak | |
| 7,220,270 B2 | 5/2007 | Sawhney et al. | |
| 7,332,566 B2 | 2/2008 | Pathak et al. | |
| 7,347,850 B2 | 3/2008 | Sawhney | |
| 7,413,752 B2 | 8/2008 | Sawhney | |
| 7,592,418 B2 | 9/2009 | Pathak et al. | |
| 7,597,882 B2 | 10/2009 | Pathak et al. | |
| 7,605,232 B2 | 10/2009 | Pathak | |

(Continued)

FOREIGN PATENT DOCUMENTS

| | | |
|---|---|---|
| CA | 2 351 787 A1 | 12/2001 |
| CN | 1682693 A | 10/2005 |

(Continued)

OTHER PUBLICATIONS

Abdi et al., Pain Physician, 2004, 7, p. 327-331 (Year: 2004).*
Koyama et al., Circ. J., 2002, 66, p. 645-648 (Year: 2002).*
Gloor et al., J Clin Invest., 1983, 71(5), p. 1457-1466 (Year: 1983).*
Bolderman et al., International Journal of Cardiology, 2011, 149, p. 341-346 (Year: 2011).*
U.S. Appl. No. 15/140,254, filed Apr. 27, 2016, Systems and Methods for Sympathetic Cardiopulmonary Neuromodulation.
U.S. Appl. No. 15/848,518, filed Dec. 20, 2017, Systems and Methods for Sympathetic Cardiopulmonary Neuromodulation.
U.S. Appl. No. 16/275,120, filed Feb. 13, 2019, Systems and Methods for Cardiac Plexus Neuromodulation.
U.S. Appl. No. 16/313,856, filed Dec. 27, 2018, Treatment of Sepsis and Related Inflammatory Conditions by Local Neuromodulation of the Autonomic Nervous System.
U.S. Appl. No. 16/981,199, filed Sep. 15, 2020, Systems and Methods for Gel-Based Neuromodulation.
U.S. Appl. No. 17/257,266, filed Dec. 30, 2020, Systems and Methods for Visceral Neuromodulation.

(Continued)

*Primary Examiner* — Jonathan S Lau
(74) *Attorney, Agent, or Firm* — Knobbe Martens Olson & Bear, LLP

(57) ABSTRACT

Methods, agents, and devices to treat medical conditions through local chemical neuromodulation of the autonomic nervous system are described. Drug formulations may be injected at or near ganglia, nerve plexi, ganglionated plexi, and nerves to treat different diseases. Target sites for the treatment of cardiac and other disease conditions may include extrinsic stellate (cervicothoracic) and cervical ganglia of the sympathetic chain, and intrinsic cardiac nerves and ganglionated plexi innervating the myocardium.

16 Claims, 11 Drawing Sheets

(56) References Cited

U.S. PATENT DOCUMENTS

| | | |
|---|---|---|
| 7,648,713 B2 | 1/2010 | Sawhney |
| 7,708,979 B2 | 5/2010 | Lowman et al. |
| 7,744,913 B2 | 6/2010 | Noyes |
| 7,772,359 B2 | 8/2010 | Pacetti |
| 7,776,063 B2 | 8/2010 | Sawhney et al. |
| 7,780,980 B2 | 8/2010 | Sawhney |
| 7,790,192 B2 | 9/2010 | Sawhney et al. |
| 7,862,538 B2 | 1/2011 | Sawhney et al. |
| 7,872,068 B2 | 1/2011 | Khosravi et al. |
| 7,914,541 B2 | 3/2011 | Sawhney et al. |
| 7,928,141 B2 | 4/2011 | Li |
| 8,003,705 B2 | 8/2011 | Sawhney et al. |
| 8,044,137 B2 | 10/2011 | Khosravi et al. |
| 8,105,622 B2 | 1/2012 | Sawhney |
| 8,175,711 B2 | 5/2012 | Demarais et al. |
| 8,206,299 B2 | 6/2012 | Foley et al. |
| 8,211,017 B2 | 7/2012 | Foley et al. |
| 8,257,723 B2 | 9/2012 | Noyes |
| 8,383,161 B2 | 2/2013 | Campbell et al. |
| 8,399,443 B2 | 3/2013 | Seward |
| 8,409,606 B2 | 4/2013 | Sawhney et al. |
| 8,465,752 B2 | 6/2013 | Seward |
| 8,470,362 B2 | 6/2013 | Sawhney et al. |
| 8,480,651 B2 | 7/2013 | Abuzaina et al. |
| 8,512,749 B2 | 8/2013 | Sawhney et al. |
| 8,535,705 B2 | 9/2013 | Pathak et al. |
| 8,557,535 B2 | 10/2013 | Pathak |
| 8,563,027 B2 | 10/2013 | Jarrett et al. |
| 8,708,995 B2 | 4/2014 | Seward et al. |
| 8,741,328 B2 | 6/2014 | Suzuki et al. |
| 8,795,709 B2 | 8/2014 | Sawhney et al. |
| 8,852,230 B2 | 10/2014 | Sawhney et al. |
| 8,852,646 B2 | 10/2014 | Campbell et al. |
| 8,916,611 B2 | 12/2014 | Roy et al. |
| 8,961,501 B2 | 2/2015 | Jarrett et al. |
| 8,986,730 B2 | 3/2015 | Sawhney et al. |
| 9,011,879 B2 | 4/2015 | Seward |
| 9,023,023 B2 | 5/2015 | McKay et al. |
| 9,125,807 B2 | 9/2015 | Sawhney et al. |
| 9,131,975 B2 | 9/2015 | McKay |
| 9,186,197 B2 | 11/2015 | McKay |
| 9,199,065 B2 | 12/2015 | Seward |
| 9,205,150 B2 | 12/2015 | Jarrett et al. |
| 9,254,267 B2 | 2/2016 | Sawhney |
| 9,308,283 B2 | 4/2016 | Campbell et al. |
| 9,358,374 B2 | 6/2016 | Dacey et al. |
| 9,370,485 B2 | 6/2016 | Sawhney et al. |
| 9,386,969 B2 | 7/2016 | Sawhney et al. |
| 9,386,990 B2 | 7/2016 | Muir et al. |
| 9,463,004 B2 | 10/2016 | Campbell et al. |
| 9,498,557 B2 | 11/2016 | Pathak et al. |
| 9,669,117 B2 | 6/2017 | Campbell et al. |
| 9,687,216 B2 | 6/2017 | Sawhney et al. |
| 9,707,000 B2 | 7/2017 | Hoke et al. |
| 9,730,986 B2 | 8/2017 | Roy et al. |
| 9,775,906 B2 | 10/2017 | Sawhney et al. |
| 9,789,161 B2 | 10/2017 | Roy et al. |
| 9,855,317 B2 | 1/2018 | Bright |
| 10,420,724 B2 | 9/2019 | Jarrett et al. |
| 10,842,494 B2 | 1/2020 | Agarwal et al. |
| 10,550,187 B2 | 2/2020 | Sawhney et al. |
| 10,675,085 B2 | 6/2020 | Clark et al. |
| 10,786,462 B2 | 9/2020 | Jarrett et al. |
| 2002/0037919 A1 | 3/2002 | Hunter |
| 2003/0152637 A1* | 8/2003 | Chasin ............ A61K 9/0024 424/501 |
| 2004/0096507 A1 | 5/2004 | Kwang et al. |
| 2004/0166088 A1 | 8/2004 | Shalaby |
| 2004/0186488 A1 | 9/2004 | Droese |
| 2004/0220296 A1 | 11/2004 | Lowman et al. |
| 2005/0203206 A1 | 9/2005 | Trieu |
| 2005/0228460 A1 | 10/2005 | Levin et al. |
| 2005/0261672 A1 | 11/2005 | Deem et al. |
| 2006/0159823 A1 | 7/2006 | Melvik et al. |
| 2006/0177481 A1 | 8/2006 | Sawhney |
| 2006/0184185 A1 | 8/2006 | Olausson et al. |
| 2006/0280797 A1 | 12/2006 | Shoichet et al. |
| 2006/0287678 A1 | 12/2006 | Shafer |
| 2007/0016274 A1 | 1/2007 | Boveja et al. |
| 2007/0253960 A1 | 11/2007 | Roy et al. |
| 2007/0255379 A1 | 11/2007 | Williams et al. |
| 2008/0114092 A1 | 5/2008 | Sawhney |
| 2008/0147137 A1 | 6/2008 | Cohen et al. |
| 2009/0047349 A1 | 2/2009 | Bennett et al. |
| 2010/0119451 A1 | 5/2010 | Sawhney |
| 2010/0168625 A1 | 7/2010 | Swain et al. |
| 2010/0255060 A1 | 10/2010 | Kajii et al. |
| 2011/0104061 A1 | 5/2011 | Seward |
| 2012/0039862 A1 | 2/2012 | Borodic |
| 2012/0049689 A1 | 3/2012 | Bennett et al. |
| 2013/0035682 A1 | 2/2013 | Weil |
| 2013/0071462 A1 | 3/2013 | Jarrett et al. |
| 2013/0204068 A1 | 8/2013 | Gnanashanmugam et al. |
| 2013/0225664 A1 | 8/2013 | Horsager et al. |
| 2013/0274674 A1 | 10/2013 | Fischell et al. |
| 2013/0287698 A1 | 10/2013 | Seward |
| 2013/0296646 A1 | 11/2013 | Barbut et al. |
| 2013/0304174 A1 | 11/2013 | Langhals et al. |
| 2014/0052168 A1 | 2/2014 | Sawhney |
| 2014/0094932 A1 | 4/2014 | Deister et al. |
| 2014/0221975 A1 | 8/2014 | Gnanashanmugam et al. |
| 2014/0271717 A1 | 9/2014 | Goshayeshgar et al. |
| 2014/0276590 A1 | 9/2014 | Hiller et al. |
| 2014/0341836 A1 | 11/2014 | Sawhney et al. |
| 2014/0350327 A1 | 11/2014 | Poon et al. |
| 2014/0363382 A1 | 12/2014 | Campbell et al. |
| 2014/0363498 A1 | 12/2014 | Sawhney et al. |
| 2015/0065945 A1 | 3/2015 | Zarins et al. |
| 2015/0132409 A1 | 5/2015 | Stein et al. |
| 2015/0305799 A1 | 10/2015 | Trieu |
| 2015/0374887 A1 | 12/2015 | Romero-Ortega et al. |
| 2016/0045602 A1 | 2/2016 | Jarrett et al. |
| 2016/0106587 A1 | 4/2016 | Jarrett et al. |
| 2016/0166504 A1 | 6/2016 | Jarrett et al. |
| 2016/0296623 A1 | 10/2016 | Sawhney et al. |
| 2016/0331738 A1 | 11/2016 | Jarrett et al. |
| 2016/0367235 A1 | 12/2016 | Campbell et al. |
| 2017/0020729 A1 | 1/2017 | Jarrett et al. |
| 2017/0143409 A1 | 5/2017 | Clark et al. |
| 2017/0266324 A1 | 9/2017 | Campbell et al. |
| 2018/0147260 A1 | 5/2018 | Bright |
| 2018/0185390 A1 | 7/2018 | Eviston et al. |
| 2019/0216899 A1 | 7/2019 | Bright |
| 2020/0085809 A1 | 3/2020 | Bright et al. |
| 2020/0206365 A1 | 7/2020 | Campbell et al. |
| 2020/0206366 A1 | 7/2020 | Campbell et al. |
| 2020/0206367 A1 | 7/2020 | Campbell et al. |
| 2020/0207860 A1 | 7/2020 | Sawhney et al. |
| 2021/0046221 A1 | 2/2021 | Deister |
| 2021/0187160 A1 | 6/2021 | Bright et al. |
| 2021/0205501 A1 | 7/2021 | Bright |
| 2021/0268271 A1 | 9/2021 | Bright |

FOREIGN PATENT DOCUMENTS

| | | |
|---|---|---|
| CN | 102125516 A | 7/2011 |
| CN | 103385850 A | 11/2013 |
| CN | 103750919 A | 4/2014 |
| CN | 103816111 A | 5/2014 |
| CN | 104069485 A | 10/2014 |
| CN | 104288091 A | 1/2015 |
| CN | 104399131 A | 3/2015 |
| CN | 109395165 A | 3/2019 |
| JP | 2000-139976 | 5/2000 |
| JP | 5453776 B2 | 3/2014 |
| RU | 2582226 C1 | 4/2016 |
| WO | WO 2001/089526 | 11/2001 |
| WO | WO 2004/002449 | 1/2004 |
| WO | WO 2009/146030 | 12/2009 |
| WO | WO 2011/085166 | 7/2011 |
| WO | WO 2012/075337 | 6/2012 |
| WO | WO 2013/165714 | 11/2013 |
| WO | WO 2014/130419 | 8/2014 |
| WO | WO 2016/019000 | 4/2016 |

(56) References Cited

FOREIGN PATENT DOCUMENTS

| WO | WO 2016/144166 | 9/2016 |
| WO | WO 2016/176333 | 11/2016 |
| WO | WO 2017/139487 | 8/2017 |
| WO | WO 2018/005848 | 1/2018 |
| WO | WO 2018/125822 | 7/2018 |
| WO | WO 2019/027272 | 2/2019 |
| WO | WO 2019/178564 | 9/2019 |
| WO | WO 2020/010123 | 1/2020 |
| WO | WO 2020/010164 | 1/2020 |
| WO | WO 2021/0146330 | 7/2021 |

OTHER PUBLICATIONS

U.S. Appl. No. 17/138,703, filed Dec. 30, 2020, Methods and Devices for In Situ Formed Nerve Cap.
U.S. Appl. No. 17/148,427, filed Jan. 13, 2021, Methods and Devices for In Situ Formed Nerve Cap with Rapid Release.
U.S. Appl. No. 15/848,518, filed Dec. 20, 2017, Systems and Methods for Sympathetic Cardopulmonary Neuromodulation.
Abbott, O. A., W. A. Hopkins, et al. (1950). "Therapeutic status of pulmonary autonomic nerve surgery." J Thorac Surg 20(4): 571-83; passim.
Adar, R., A. Kurchin, et al. (1977). "Palmar hyperhidrosis and its surgical treatment: a report of 100 cases." Ann Surg 186(1): 34-41.
Albers, James, et al. "Interventions for preventing neuropathy caused by cisplatin and related compounds." Cochrane Database Syst Rev 1.1 (2007).
Antila, H., and O. Kirvelä. "Neurolytic thoracic paravertebral block in cancer pain." Acta anaesthesiologica scandinavica 42.5 (1998): 581-585.
Antolak SJ, et al. "Therapeutic Pudendal Nerve Blocks Using Corticosteriods Cure Pelvic Pain after Failure of Sacral Neuromodulation" Pain Medicine 2009, vol. 10, No. 1, pp. 185-189.
B Braun Plexus Anaesthesia product guide (2014) in 10 pages.
Baumgartner, F. J. (2008). "Surgical approaches and techniques in the management of severe hyperhidrosis." Thorac Surg Clin 18(2): 167-81.
Baumgartner, Fritz J., et al. "Thoracoscopic sympathicotomy for disabling palmar hyperhidrosis: a prospective randomized comparison between two levels." The Annals of thoracic surgery 92.6 (2011): 2015-2019.
BD PuraMatrix Peptide Hydrogel Brochure (2004) in 4 pages.
Blades, B., E. J. Beattie, Jr., et al. (1950). "The surgical treatment of intractable asthma." J Thorac Surg 20(4): 584-91; passim.
Boezaart, André P. Atlas of peripheral nerve blocks and anatomy for orthopaedic anesthesia. Elsevier Health Sciences, p. 218, 2008.
Cai, "Injectable glycosaminoglycan hydrogels for controlled release of human basic fibroblast growth factor" Biomaterials 26 (2005) 6054-6067 (Year: 2005).
Carli, Mirjana, et al. "Tph2 gene deletion enhances amphetamine-induced hypermotility: effect of 5-HT restoration and role of striatal noradrenaline release." Journal of neurochemistry 135.4 (2015): 674-685.
Carr, D. and H. Chandler (1948). "Dorsal sympathetic ganglionectomy for intractable asthma." J Thorac Surg 17(1): 1-12.
Chaibundit, Chiraphon, et al. "Effect of ethanol on the gelation of aqueous solutions of Pluronic F127." Journal of colloid and interface science 351.1 (2010): 190-196.
Chaibundit, Chiraphon, et al. "Effect of Ethanol on the Micellization and Gelation of Pluronic P123." Langmuir 24.21 (2008): 12260-12266.
Chang, Jason Y., Kevin D. Phelan, and Janet A. Chavis. "Neurotoxicity of 25-OH-cholesterol on sympathetic neurons." Brain research bulletin 45.6 (1998): 615-622.
Cheema, S., J. Richardson, and P. McGurgan. "Factors affecting the spread of bupivacaine in the adult thoracic paravertebral space." Anaesthesia 58.7 (2003): 684-687.
Cressman, Erik NK, and David A. Jahangir. "Dual mode single agent thermochemical ablation by simultaneous release of heat energy and acid: hydrolysis of electrophiles." International Journal of Hyperthermia 29.1 (2013): 71-78.
Cunningham, D. J. (1913). Cunningham's Textbook of Anatomy, William Wood (648-734).
Da Rocha, R. P., A. Vengjer, et al. (2002). "Size of the collateral intercostal artery in adults: anatomical considerations in relation to thoracocentesis and thoracoscopy." Surg Radiol Anat 24(1): 23-6.
Denby, Christine, et al. "Temporary sympathectomy in chronic refractory angina: a randomised, doubleblind, placebo-controlled trial." British journal of pain 9.3 (2015): 142-148.
Dimitrov-Szokodi, D., G. Balogh, et al. (1957). "Lung denervation in the therapy of intractable bronchial asthma." J Thorac Surg 33(2): 166-84.
Downing, S. Evans, and John C. Lee. "Nervous control of the pulmonary circulation." Annual Review of Physiology 42.1 (1980): 199-210.
Drott, C. and G. Claes (1996). "Hyperhidrosis treated by thoracoscopic sympathicotomy." Cardiovasc Surg 4(6): 788-90; discussion 790-1.
Dumont, Pascal. "Side effects and complications of surgery for hyperhidrosis." Thoracic surgery clinics 18.2 (2008): 193-207.
Dun, N. J., and A. G. Karczmar. "Evidence for a presynaptic inhibitory action of 5-hydroxytryptamine in a mammalian sympathetic ganglion." Journal of Pharmacology and Experimental Therapeutics 217.3 (1981): 714-718.
Evicore. Clinical Guidelines. Aug. 11, 2017. [Retrieved Sep. 3, 2019] Retrieved from online URL: https://www.evicore.com/-/media/files/evicore/clinical-guidelines/solut1on /m sk-advance/archive/cmm-207—oain-eoidural-adhesiolvsiseffOB1117 102118.pdf.
Feinberg, Samuel M. "Progress in Asthma: Literature for 1934 and 1935." Journal of Allergy 7.3 (1936): 268-294.
Finucane 2017, "complications of regional anesthesia" published by Springer, 2017 p. 213.
Fredman, B., E. Zohar, et al. (2000). "Video-assisted transthoracic sympathectomy in the treatment of primary hyperhidrosis: friend or foe?" Surg Laparosc Endosc Percutan Tech 10(4): 226-9.
Freeman, N. E., R. H. Smithwick, et al. (1934). "Adrenal Secretion in Man." Am. J. Physiol. 107(3): 529.
http://www.fziomed.com/core-science/ web page last updated Aug. 19, 2016 in 2 pages.
Garcia-Morales, Luis et al., "Intraoperative Surgical Sealant Application during Cardia Defect Repair", Texas Heart Institute Journal, vol. 41, No. 4, Aug. 1, 2014, pp. 440-442.
Gay, L. N. and W. M. Reinhoff (1934). "Further Observations on the Treatment of Intractable Bronchial Asthma by Bilateral Resection of the Pulmonary Plexus." J. Allergy 13(6): 626-631.
Gossot, D., H. Kabiri, et al. (2001). "Early complications of thoracic endoscopic sympathectomy: a prospective study of 940 procedures." Ann Thorac Surg 71 (4): 1116-9.
Gossot, D., L. Toledo, et al. (1997). "Thoracoscopic sympathectomy for upper limb hyperhidrosis: looking for the right operation." Ann Thorac Surg 64(4): 975-8.
Haam, Seokjin, et al. "An anatomical study of the relationship between the sympathetic trunk and intercostal veins of the third and fourth intercostal spaces during thoracoscopy." Clinical Anatomy 23.6 (2010): 702-706.
Hayakawa, Kazuhiro, et al. "Nerve growth factor prevention of aged-rat sympathetic neuron injury by cisplatin, vincristine and taxol—in vitro explant study." Neuroscience letters 274.2 (1999): 103-106.
Hsu, C. P., C. Y. Chen, et al. (1998). "Resympathectomy for palmar and axillary hyperhidrosis." Br J Surg 85(11): 1504-5.
Huang, B., et al. "[Therapeutic feasibility of percutaneous puncture and chemical neurolysis of thoracic sympathetic nerve block in palmar hyperhidrosis under the guidance of computed tomograph]." Zhonghua yi xue za zhi 91.38 (2011): 2710-2713.
Ilfeld, et al. "Ultrasound-guided Percutaneous Peripheral Nerve Stimulation for Analgesia Following Total Knee Arthroplsaty: a Prospective Feasibility Study" Journal of Orthopaedic Surgery and Research 2017, vol. 12, No. 4, pp. 1-9.
Imrich, Richard, et al. "Functional effects of cardiac sympathetic denervation in neurogenic orthostatic hypotension." Parkinsonism & related disorders 15.2 (2009): 122-127.

(56) References Cited

OTHER PUBLICATIONS

Ireland, S. J., and C. C. Jordan. "Pharmacological characterization of 5-hydroxytryptamine-induced hyperpolarization of the rat superior cervical ganglion." British journal of pharmacology 92.2 (1987): 417-427.

Ischemia. Wikipedia. Dec. 24, 2017. [Retrieved Sep. 3, 2019] Retrieved from online URL:https://en.wikipedia.org/w/index.php?title=Ischemia&oldid=816854406.

Karmakar, M. K., T. Gin, and AM-H. Ho. "Ipsilateral thoracolumbar anaesthesia and paravertebral spread after low thoracic paravertebral injection." British journal of anaesthesia 87.2 (2001): 312-316.

Kaur, Gurjinder, et al. "Estrogen regulation of neurotrophin expression in sympathetic neurons and vascular targets." Brain research 1139 (2007): 6-14.

Kimura, Tomohiko, Toshitake Shimamura, and Susumu Satoh. "Effects of pirenzepine and hexamethonium on adrenal catecholamine release in responses to endogenous and exogenous acetylcholine in anesthetized dogs." Journal of cardiovascular pharmacology 20.6 (1992): 870-874.

Klodell, Charles T., et al. "Oximetry-derived perfusion index for intraoperative identification of successful thoracic sympathectomy." The Annals of thoracic surgery 80.2 (2005): 467-470.

Krediet, Annelot C., et al. "Different Approaches to Ultrasound-guided Thoracic Paravertebral BlockAn Illustrated Review." The Journal of the American Society of Anesthesiologists 123.2 (2015): 459-474.

Lee, Ju Young, et al. "In vivo efficacy of paclitaxel-loaded injectable in situ-forming gel against subcutaneous tumor growth." International journal of pharmaceutics 392.1 (2010): 51-56.

Lee, Sang Beom, et al. "Morphometric Study of the Upper Thoracic Sympathetic Ganglia." Journal of Korean Neurosurgical Society 50.1 (2011): 30-35.

Levin, G. L. (1935). "The Treatment of Bronchial Asthma by Dorsal Sympathectomy: Direct and Indirect." Ann Surg 102(2): 161-70.

Li, et al. "Controlled Release of Protein from Biodegradable Mutio-Senstitive Injectable Poly (etherurethane) Hydrogel" ACS Appl. Mater. Interfaces 2014, vol. 6, No. 5, pp. 3640-3647.

Lin K L et al. "DuraSeal as a Ligature in the Anastomosis of rat Sciatic Nerve Gap Injury", Journal of Surgical Research, Academic Press Inc. San Diego CA US, vol. 161, No. 1, Jun. 1, 2010, pp. 101-110.

Lin, Zhiqiang, et al. "Novel thermo-sensitive hydrogel system with paclitaxel nanocrystals: High drug-loading sustained drug release and extended local retention guaranteeing better efficacy and lower toxicity." Journal of Controlled Release 174 (2014): 161-170.

Liu, et al., 2009, European J of Cariothoracic Surgery, 35, 398-402.

Macaya, D., and M. Spector. "Injectable hydrogel materials for spinal cord regeneration: a review." Biomedical materials 7.1 (2012): 012001.

Mahajan, Mohit, P. Utreja, and S. K. Jain. "Paclitaxel Loaded Nanoliposomes in Thermosensitive Hydrogel: A Dual Approach for Sustained and Localized Delivery." Anti-cancer agents in medicinal chemistry (2015).

Malik, Tariq. "Ultrasound-Guided Paravertebral Neurolytic Block: A Report of Two Cases." Pain Practice 14.4 (2014): 346-349.

Marinescu, Mark A., et al. "Coronary microvascular dysfunction, microvascular angina, and treatment strategies." JACC: Cardiovascular Imaging 8.2 (2015): 210-220.

Matchett, Gerald. "Intercostal Nerve Block and Neurolysis for Intractable Cancer Pain." Journal of Pain & Palliative Care Pharmacotherapy (2016): 1-4.

Mehdizadeh, Mohammadreza, and Jian Yang. "Design strategies and applications of tissue bioadhesives." Macromolecular bioscience 13.3 (2013): 271-288.

Microstimulation. Wikipedia. Jun. 30, 2016. [Retrieved Sep. 3, 2019) Retrieved from online URL:https://en.Wikipedia.org/w/index.php?title=Microstimulation&oldid=727594711.

Moawad, H. M. M., and H. Jain. "Development of nano-macroporous soda-lime phosphofluorosilicate bioactive glass and glass-ceramics." Journal of Materials Science: Materials in Medicine 20.7 (2009): 1409-1418.

Murray, Gary L., and Joseph Colombo. "Ranolazine preserves and improves left ventricular ejection fraction and autonomic measures when added to guideline-driven therapy in chronic heart failure." Heart International 9.2 (2014): 66-73.

Naja, M. Z., et al. "Varying anatomical injection points within the thoracic paravertebral space: effect on spread of solution and nerve blockade." Anaesthesia 59.5 (2004): 459-463.

Ng, Ivan, and Tseng-Tsai Yeo. "Palmar hyperhidrosis: intraoperative monitoring with laser Doppler blood flow as a guide for success after endoscopic thoracic sympathectomy." Neurosurgery 52.1 (2003): 127-131.

Nunn, J. F., and G. Slavin. "Posterior intercostal nerve block for pain relief after cholecystectomy anatomical basis and efficacy." British journal of anaesthesia 52.3 (1980): 253-260.

Oblasti primeneniya protivospacchnogo gelya Mezogel [online] 20 Oct. 11, 27 retrieved on Aug. 2, 2016 from URL: http://www.mesogel.ru/prod/mesogel4.htm>.

Ostermann Pa et al. "The ligament system of the spleen and its significance for surgical interventions" Langenbecks Arch Chir 1987;371 (3):207-16, abstract.

Pai, et al., "Spleen Anatomy" (Medscape, 2014, p. 1-6). (Year: 2014).

Pandin, Pierre, Samia Rettab, and Alphonse Lubansu. "Ultrasound Guidance Is Helpful for Paravertebral Block Performance and Catheter Placement in Patients with Laminectomy after Thoracotomy or Lumbotomy: A Case Series Imaging Study." (2013).

Paredi, P. and P. J. Barnes (2009). "The airway vasculature: recent advances and clinical implications." Thorax 64(5): 444-50.

Parlato, Matthew, et al. "Adaptable poly (ethylene glycol) microspheres capable of mixed-mode degradation." Acta biomaterialia 9.12 (2013): 9270-9280.

Phillips, E. W. and W. J. M. Scott (1929). "The Surgical Treatment of Bronchial Asthma." Arch Surg. 19(6): 1425-1456.

Pierce, Nathan E. et al., "Hydrogel sutureless facial nerve repair: Pilot Clinical Investigation: Sutureless Facial Nerve Repair", The Laryngoscope, Jun. 2015. vol. 125, No. 6, First Published, Dec. 4, 2014, pp. 1456-1459.

Ponce Gonzalez, M. A., G. J. Serda, et al. (2005). "Long-term pulmonary function after thoracic sympathectomy." The Journal of Thoracic and Cardiovascular Surgery 129(6): 1379-1382.

Richardson and Lonnqvist, (1998) "Thoracic Paravertebral Block" British Journal of Anaesthesia 81: 230-238.

Rienhoff WF Jr, G. L. (1938). "Treatment of Intractable Bronchial Asthma by Bilateral Resection of the Posterior Pulmonary Plexus." Arch Surg. 37(3): 456-469.

Riquet, M. (2007). "Bronchial arteries and lymphatics of the lung." Thorac Surg Clin 17(4): 619-38, viii.

Robinson, Eric A., et al. "Estimating sympathetic tone by recording subcutaneous nerve activity in ambulatory dogs." Journal of cardiovascular electrophysiology 26.1 (2015): 70-78.

Rongen, Gerard A., et al. "Presynaptic inhibition of norepinephrine release from sympathetic nerve endings by endogenous adenosine." Hypertension 27.4 (1996): 933-938.

Rosas-Ballina, et al., "Cholingergic control of inflammation" J. Intern Med.Jun. 2009; 265(6): 663-679.

Shvaichak E. Zavisimost vyazkosti vodnogo rastvora gialuronovoi kisloty ot ee mikrostruktury. Chast 1. Rossysky zhurnal biomekhaniki, tom 7, No. 3: 87-98, 2003.

Singh, Narendra K., and Doo Sung Lee. "In situ gelling pH-and temperature-sensitive biodegradable block copolymer hydrogels fordrug delivery." Journal of Controlled Release 193 (2014): 214-227.

Takatori, Mayumi, Yoshihiro Kuroda, and Munetaka Hirose. "Local anesthetics suppress nerve growth factor-mediated neurite outgrowth by inhibition of tyrosine kinase activity of TrkA." Anesthesia & Analgesia 102.2 (2006): 462-467.

Vallieres, E. (2007). "The costovertebral angle." Thorac Surg Clin 17(4): 503-10.

(56) References Cited

OTHER PUBLICATIONS van der Velden, Vincent HJ, and Anthon R. Hulsmann. "Autonomic innervation of human airways: structure, function, and pathophysiology in asthma." Neuroimmunomodulation 6.3 (1999): 145-159.
van Maanen, et al., "The cholinergic anti-inflammatory pathway: towards innovative treatment of rheumatoid arthritis" (Nature Reviews, Rheumatology, 5, Apr. 2009, 229-232) (Year: 2009).
Vanaclocha, V., N. Saiz-Sapena, et al. (2000). "Uniportal endoscopic superior thoracic sympathectomy." Neurosurgery 46(4): 924-8.
Vida, Gergely, et al., "α7-Cholinergic Receptor Mediates Vagal Induction of Splenic Norepinephrine", J Immunol 2011; 186:4340-4346; Prepublished online Feb. 21, 2011.
Vida, Gergely, et al., "β2-Adrenoreceptors of regulatory lymphocytes are essential for vagal neuromodulcation of the innate immune system", The FASEB Journal, vol. 25, Dec. 2011, pp. 4476-4485.
Wallace D G et al., "A tissue sealant based on reactive multifunctional polyethylene glycol", Journal of BioMedical Materials Research, Wiley, New York, NY US. vol. 58, No. 5, Apr. 25, 2015 pp. 545-555.
Wang, Peizong, et al. "Antinociceptive effect of intrathecal amiloride on neuropathic pain in rats." Neuroscience letters 604 (2015): 24-29.
Wang, William et al.: "Clinical efficacy of epicardial application of drug-releasing hydrogels to prevent postoperative atrial fibrillation", Journal of thoracic and Cardiovascular Surgery, vol. 151, No. 1, First read: Apr. 25, 2015, pp. 80-85.
Weksler et al., 2008, Thorac Surg Clin, 18, 183-191.
Westerlund, Taina, Ville Vuorinen, and Matias Röyttä. "The perineurium modifies the effects of phenol and glycerol in rat sciatic nerve." Acta neuropathologica 108.4 (2004): 319-331.
Wilensky, H. M. (1940). "Peri-Sympathetic Injection Treatment of Asthma." Can Med Assoc J 43(1): 59-62.
Xu, Xian, et al. "Hyaluronic acid-based hydrogels: from a natural polysaccharide to complex networks." Soft matter 8.12 (2012): 3280-3294.
Yahagi, Naoki, Tsuyoshi Akiyama, and Toji Yamazaki. "Effects of ω-conotoxin GVIA on cardiac sympathetic nerve function." Journal of the autonomic nervous system 68.1 (1998): 43-48.
Yamazaki, Toji, Tsuyoshi Akiyama, and Toru Kawada. "Effects of ouabain on in situ cardiac sympathetic nerve endings." Neurochemistry international 35.6 (1999): 439-445.
Yohn, Samantha E., et al. "Not all antidepressants are created equal: differential effects of monoamine uptake inhibitors on effort-related choice behavior." Neuropsychopharmacology (2015).
Zarse, Markus, et al. "Selective increase of cardiac neuronal sympathetic tone: a catheter-based access to modulate left ventricular contractility." Journal of the American College of Cardiology 46.7 (2005): 1354-1359.
Zhang, Hongling, and Javier Cuevas. "Sigma Receptors Inhibit High-Voltage—Activated Calcium Channels in Rat Sympathetic and Parasympathetic Neurons." Journal of neurophysiology 87.6 (2002): 2867-2879.
Zhao, Ying-Zheng, et al. "Using NGF heparin-poloxamer thermosensitive hydrogels to enhance the nerve regeneration for spinal cord injury." Acta biomaterialia 29 (2016): 71-80.
Ajijola, "Bilateral Cardiac Sympathetic Denervation for the Management of Electrical Storm" JACC, 2012; 59(1): 91-92.
Ajijola, "Remodeling of stellate ganglion neurons after spatially targeted myocardial infarction: neuropeptide and morphologic changes" Hearth Rhythm, 2015; 12(5), 1027-1035.
Collura, "Left cardiac sympathetic denevation for the treatment of long QT syndrome and catecholaminergic polymorphic ventricular tachycardia using video-assisted thoracic surgery" heart Rhythm, 2009; 6: 752-59.
Fernandez, "Adrenergic and Cholinergic Plasticity in Heart Failure" Circulation Research, 2015; 116: 1639-1642.
Fukuda, "Cardiac Innervation and Sudden Cardiac Death" Circulation Research, 2015; 116: 2005-2019.
Kopecek, "Peptide-directed self assembly of hydrogels" Acta Biomater. Mar. 2009; 5(3): 805-816 (Year: 2009).
Ripplinger, "The nervous heart" Progress in Biophysics and Molecular Biology, 2016; 120: 199-209.
Schlaich, "Sympathetic Augmentation in Hypertension Role of Nerve Firing, Norepinephrine Reuptake, and Angiotensin Neuromodulation" Hypertension, 2004; 43: 169-175.
Schwartz, "Prevention of Sudden Cardiac Death After a First Myocardial Infarction by Pharmacologic or Surgical Antiadrenergic Interventions" J. Cardiovasc Electrophysiol, 1992; 3: 2-16.
Shen, "Role of the Autonomic Nervous System in Modulating Cardiac Arryhtmias" Circulation Research, 2014; 114: 1004-1021.
Sudoh, "Tricyclic antidepressants as long-acting local anesthetics" Pain 103 (2003) 49-55 (Year: 2003).
Vaseghi, "Cardiac sympathetic denervation in patients with refractory ventricular arrhythmias or electrical storm: Intermediate and long-term follow-up" Heart Rhythm, 2014; 11: 360-366.

\* cited by examiner

METHODS, AGENTS, AND DEVICES FOR LOCAL NEUROMODULATION OF AUTONOMIC NERVES

CROSS-REFERENCE TO RELATED APPLICATION

This application is the U.S. National Stage under 37 C.F.R. § 371 of PCT App. No. PCT/US2017/017223, filed Feb. 9, 2017, which in turn claims the benefit of U.S. provisional application No. 62/293,327, filed Feb. 9, 2016, which is hereby incorporated by reference in its entirety.

BACKGROUND

There is increasing experimental and clinical evidence that the autonomic regulation is essential to maintain normal physiologic function and response in organs and autonomic dysfunction plays a significant role in the development of chronic diseases. Abnormalities in the sympathetic and parasympathetic branches of the autonomic nervous system have been shown to be associated with several medical conditions including, hypertension, cardiac disease (angina, myocardial infarction, atrial and ventricular arrhythmias, cardiac arrest, sudden cardiac death, and heart failure, channelopathies), pulmonary hypertension, sleep apnea, chronic kidney disease, metabolic syndrome (obesity, glucose metabolism and insulin sensitivity), chronic obstructive pulmonary disease (COPD), stroke, pain, glaucoma (and other ocular diseases), hyperhidrosis, gut disease (Crohn's disease, irritable bowel syndrome), and polycystic ovary syndrome.

A majority of these diseases are currently treated by systemic daily use of oral medications, some of which may not specifically target the autonomic nervous system or sympathetic nerves. Drugs have side effects and some patients are not responsive to drug therapy. Moreover, patients may not be compliant daily medication limiting the effectiveness of treatment.

A few device-based therapies are currently available or are under clinical investigation to treat different disease states. Implantable cardioverting defibrillators (ICDs) and pace makers are used to treat cardiac arrhythmias through electrical energy stimulation of at nerve conduction sites in the heart. Implantable neurostimulation devices activate the vagus nerve, spinal cord, and carotid body (or baroreceptors), to affect the autonomic function, are in clinical use or development to treat hypertension, heart failure, and chronic pain. Implant-based treatments are invasive and require the implantation of an expensive electrical generator and electrical leads to continuously monitor nerve signals and stimulate the nerves. Tissue-ablation catheters, based on radiofrequency (RF), ultrasound, and cryothermal energy forms, are in development or clinical use to treat cardiac arrhythmias, hypertension, pulmonary hypertension, and COPD by ablating tissue near specific organs. Ablation treatments may cause collateral damage to surrounding tissue and their long-term efficacy could be improved.

Local chemical neuromodulation methods that overcome these limitations are described. Target nerve, ganglion, and nerve plexus sites inside the body, that mediate chronic diseases are described. Methods to access and verify nerve location, affect nerve function, and treat diseases are described. Treatments may include a one-time administration of a neuromodulating or nerve-affecting drug composition, locally, at or near neuronal tissue sites (neurons, ganglia, plexi, and combinations). Drug compositions and formulations are also described.

SUMMARY

Methods are described for treating disease by inserting a therapy delivery device inside the body, advancing the device to a nerve site of the autonomic nervous system, measuring the nerve activity at the target site, and administering a small volume of drug formulation, locally, at or near the target nerve site to affect nerve function and treat the disease.

Nerve sites may include the cervicothoracic ganglion, also known as the stellate ganglion, adjacent cervical and thoracic ganglia (C1 to T4) of the sympathetic chain, interconnecting nerves between them, and rami communicantes. Other diseases and organ-specific nerve sites and ganglia are also described.

Medical conditions treated may include cardiac disease condition like angina, myocardial infarction (acute and late), atrial arrhythmias (fibrillation), ventricular arrhythmias (ventricular fibrillation, ventricular tachycardia), heart failure, channelopathies (long-QT syndrome, polymorphic ventricular tachycardia), cardiomyopathy, cardiac arrest, and sudden cardiac death. Other disease conditions that may be treated include stroke, hypertension, pulmonary hypertension, pain, chronic regional pain syndrome, post-traumatic stress syndrome, and hot flashes.

Agents may include drug formulations based on ion pump and ion channel antagonists, G-protein coupled receptor (GPCR) agonists and antagonists, etc. Drug formulations may be administered at or near target nerves or ganglia directly, or may be mixed with excipients and polymers to provide sustained drug release over time to permanently affect nerve function and treat the disease for several days to several years.

Neuromodulatory effects of drug compositions described may include blocking nerves (to stop nerve signal transmission), upregulating nerves (to increase sympathetic nerve activity), and downregulating nerves (to reduce parasympathetic nerve activity) over short or long periods of time. Drug compositions are described which may treat disease by permanently killing nerves through apoptosis and preventing nerve regeneration, while reducing damage to surrounding organs and tissue.

Also described are methods and devices for accessing ganglia, plexi, ganglionated plexi, sympathetic nerves and nerve fibers inside the body; for visualizing and measuring autonomic activity at target nerve sites before treatment; for locally administering drug formulations at or near nerve target sites and treat disease; and for monitoring autonomic feedback during and after treatment.

Methods are described to identify, screen, and qualify patients with chronic diseases mediated by autonomic dysfunction. Devices and methods are described to monitor nerve activity and other diagnostic markers to verify disease mechanisms and target nerve locations for disease.

Treatments described may be used either as an adjunctive treatment or an alternative treatment to other therapies in clinical practice or under clinical investigation. Treatments described may be administered at the time of primary procedure. Treatment may also be performed, 3 weeks to 3 months, prior to a second procedure to allow sufficient time for reduction in catecholamine levels.

Drug formulations described may be injected at one or more target nerve locations inside the body to treat one medical condition. Drug formulations, administered at different sites, may be different to achieve desired therapeutic benefits at specific locations over desired time periods.

DESCRIPTION

Methods, agents, and devices are described to treat diseases and medical conditions through local chemical neuromodulation at or near nerve target sites inside of the autonomic nervous system, such as the sympathetic nerves, ganglia, and nerve plexi inside the body.

Anatomy of the Autonomic Nervous System and the Sympathetic Chain

Figure 1A:
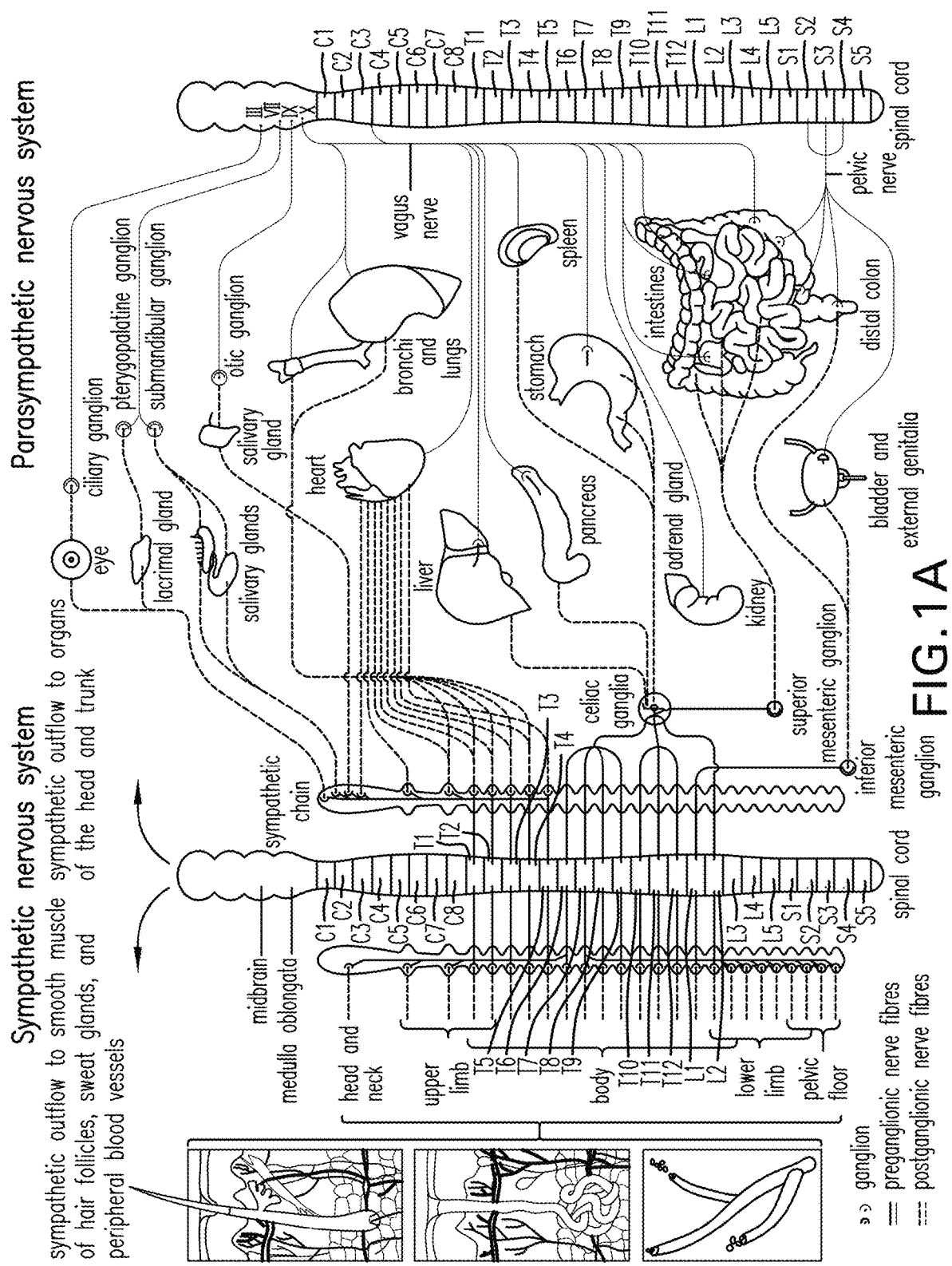
FIG. 1A shows the autonomic nervous system, including the sympathetic and parasympathetic nervous system and the sympathetic chain ganglia, innervating various organs in the body.

The autonomic nervous system (ANS) is the division of the peripheral nervous system that acts as a control system to influence internal organs and unconsciously regulate bodily functions, such as heart rate, digestion, and respiration rate etc., as shown in FIG. 1A. The ANS has two divisions, the sympathetic nervous system (SNS) and the parasympathetic nervous system (PSNS). The SNS is considered the "fight or flight" system and the PSNS is considered the "rest and digest" system. In most cases, sympathetic and parasympathetic nervous systems have opposing actions of activating and inhibiting a physiological response and form feedback loops within various organs and systems inside the body. The functions of the ANS may be further divided into sensory (afferent, sending signals to the brain and central nervous system) and motor (efferent, affecting end organs) subsystems.

Sympathetic Nervous System:

The SNS includes nerve cells with bodies in a column along either side (left and right) of the vertebral bodies from the T1 to L2/3 vertebrae. These cell bodies are general visceral efferent, preganglionic neurons and they can synapse with their postganglionic neurons at several locations—paravertebral ganglia, prevertebral ganglia and chromaffin cells. As shown in FIG. 1A, the paravertebral ganglia of the sympathetic chain include cervical ganglia, thoracic ganglia, lumbar ganglia, and sacral ganglia linked together on each side of the human body, also referred to as the sympathetic trunks.

The cervical ganglia are paravertebral ganglia of the SNS and include the superior-cervical ganglion adjacent to C2 and C3 (innervating the heart, head and neck), middle cervical ganglion (adjacent to C6) innervating the heart and the neck, and the inferior cervical ganglion (adjacent to C7). The inferior cervical ganglion is often fused to the first thoracic ganglion to form a single structure, called the stellate ganglion or cervicothoracic ganglion, innervating the heart, lower neck, arm, and posterior cranial arteries. The thoracic ganglia are 12 paravertebral ganglia. Thoracic (cardiopulmonary, the greater, lesser and least) splanchnic nerves emerging from the ganglia innervate the abdominal structures. The lumbar ganglia, typically four, are paravertebral ganglia. Lumbar splanchnic nerves arise from these ganglia and supply sympathetic efferent nerve fibers to nearby plexi—the celiac plexus, superior mesenteric plexus, inferior mesenteric plexus, renal plexus, and aortic plexus. The sacral ganglia are paravertebral ganglia of sympathetic trunk. Generally there are 4-5 sacral ganglia provide sympathetic nerve fibers to the sacral splanchnic nerves to join the hypogastric plexus.

Figure 1B:
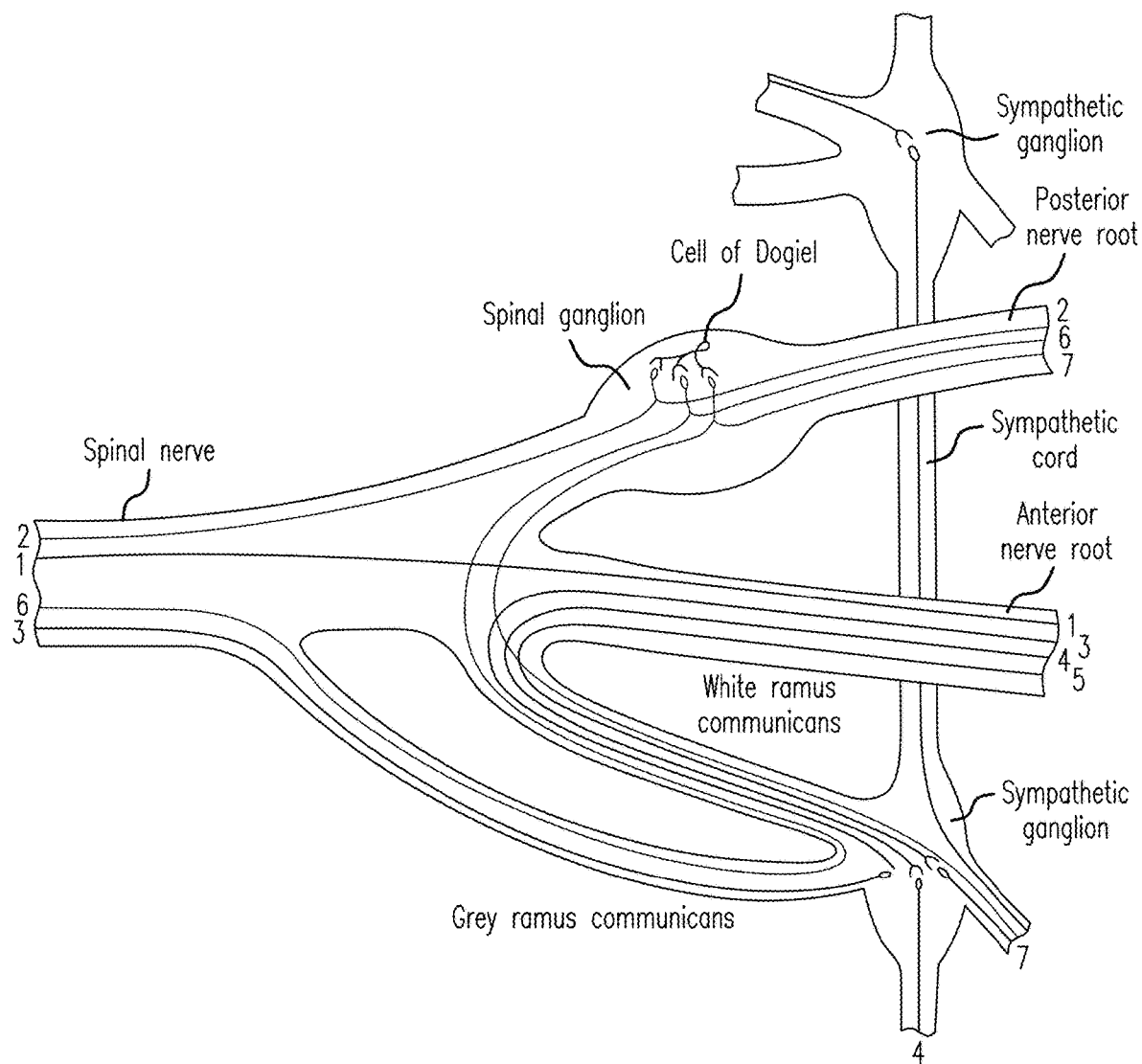
FIGS. 1B-1D show pathways of the grey and white rami communicantes connecting the spinal nerves and the sympathetic nervous system near the dorsal root ganglia.
Figure 1C:
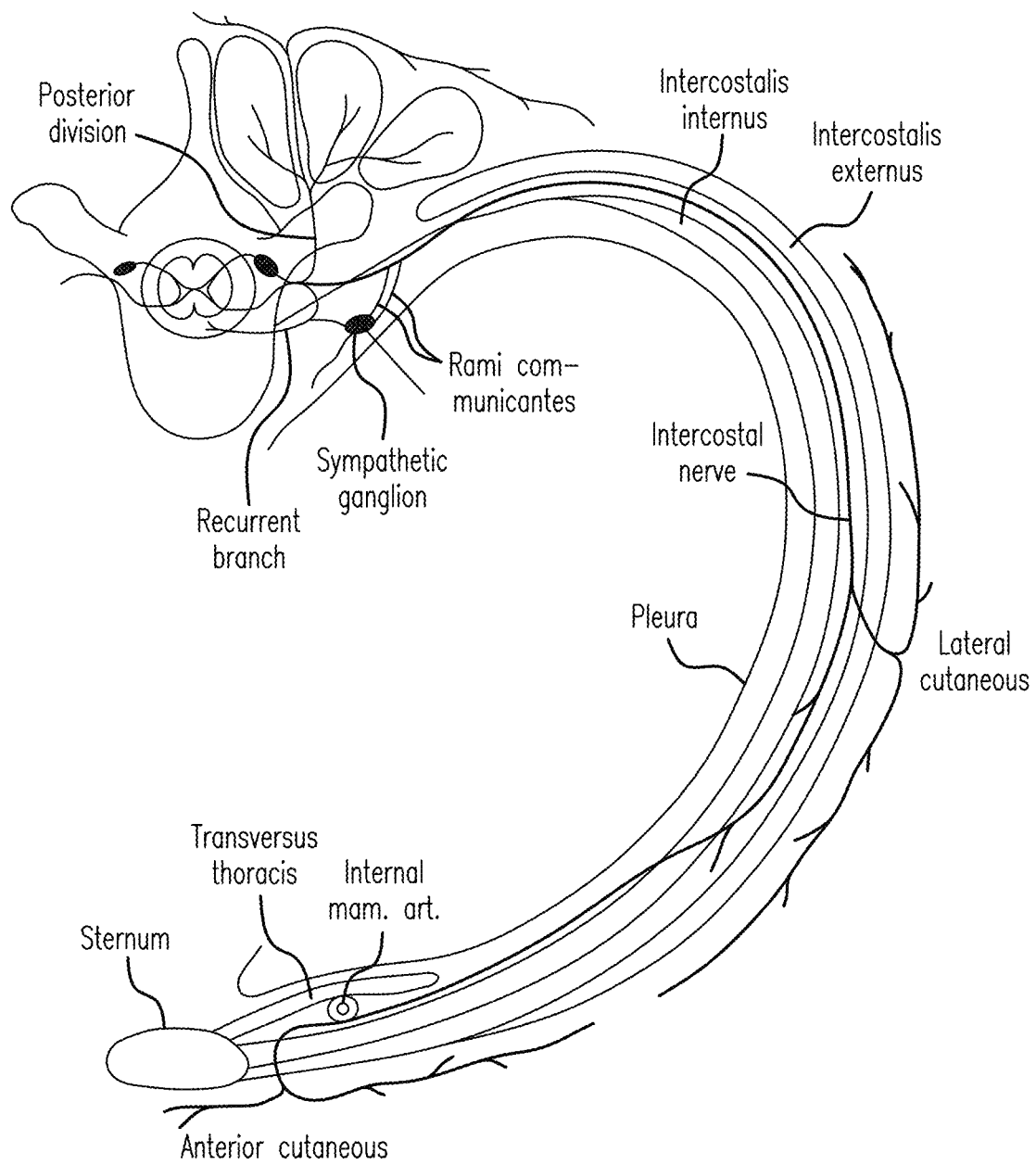
Figure 1D:
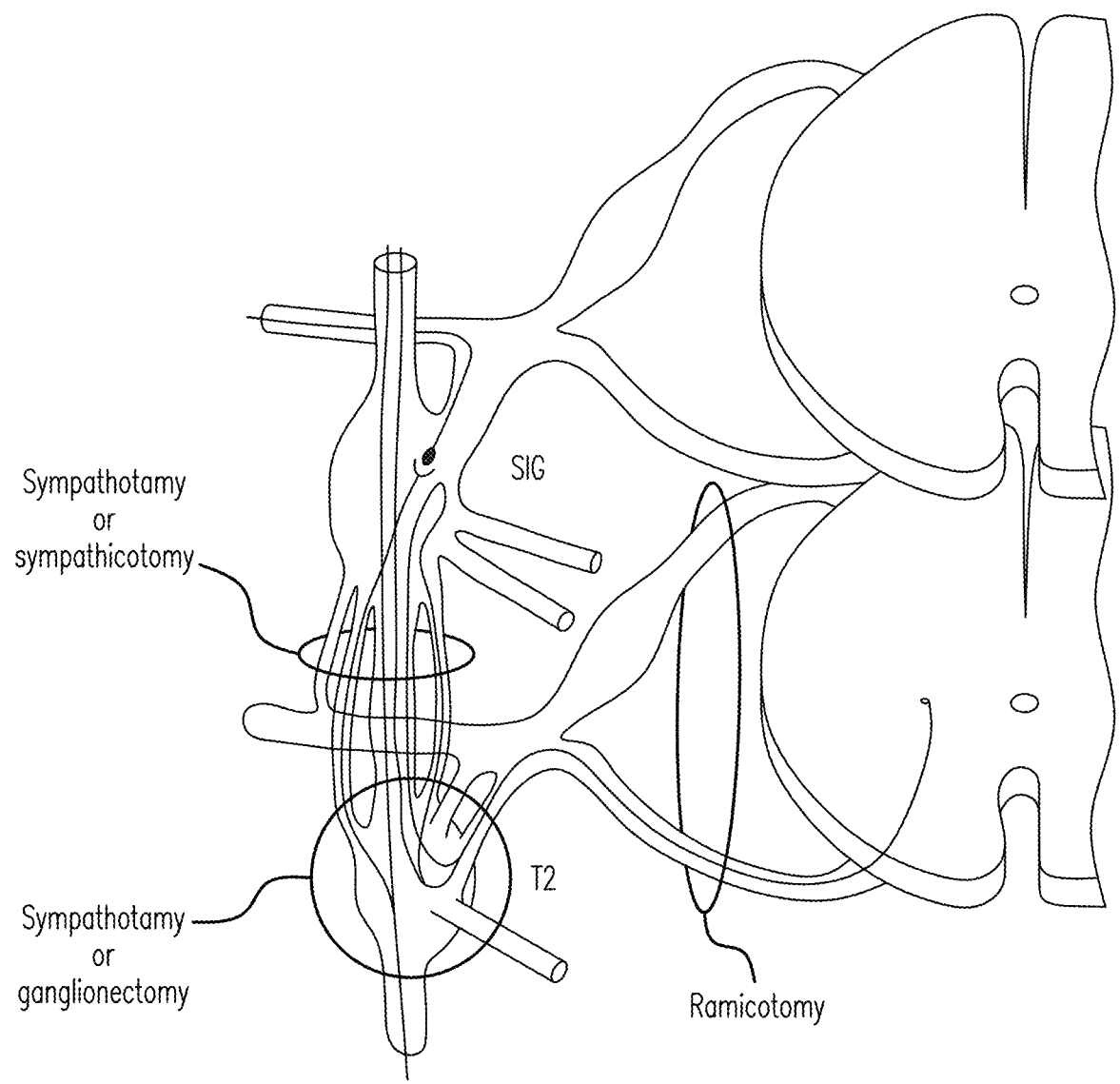

The sympathetic truck connects with the spinal nerves through structures called rami communicantes, as shown in FIGS. 1B-1D. A ramus communicans is a connecting nerve branch between a spinal nerve and the sympathetic trunk. Two kinds of rami communicantes, white and grey, are responsible for conveying ANS signals, specifically for the SNS. Grey rami communicantes are more myelinated that white rami and exist at every level of the spinal cord. They are responsible for carrying post-ganglionic nerve fibers from the paravertebral ganglia to their destination, and for carrying the pre-ganglionic fibers, which enter the paravertebral ganglia but do not synapse. White rami communicantes are only present near the intermediolateral cell column (T1-L2) and are responsible for carrying pre-ganglionic nerve fibers from the spinal cord to the paravertebral ganglia.

The prevertebral ganglia are sympathetic ganglia that lie between the paravertebral ganglia and the target organ. They consist of the celiac ganglion, aortico-renal ganglion, superior mesenteric ganglion and inferior mesenteric ganglion. Post-ganglionic neurons that synapse in these ganglia innervate the pelvic viscera through different (greater-T5 to T9; lesser-T10-T11; and least-T12) splanchnic nerves, including the enteric nervous system, kidneys, bladder and other organs present in the abdomen.

Parasympathetic Nervous System:

The PSNS consists of nerve cells with preganglionic bodies in brain stem (cranial nerves II, VII, IX, X) and the spinal cord (S2, S3 and S4). They synapse with post-ganglionic neurons near the parasympathetic ganglia of the head (ciliary, submandibular, pterygopalatine and otic ganglia) or near the organ wall innervated by the vagus or sacral nerves. Post-ganglionic parasympathetic splanchnic nerves and the vagus nerve innervate the organs such as the heart, lungs, liver and stomach. Vagal efferents extend from the medulla to post-ganglionic nerves that innervate the atria in the heart.

Neurotransmitters:

Norepinephrine (NE) is the primary neurotransmitter in post-ganglionic nerves of the SNS and acetylcholine (ACh) the neurotransmitter in pre-ganglionic nerves responsible for nerve function, signal conduction, sensory perception and motor function. Sympathetic nerve fibers that secrete NE are also called adrenergic fibers. Dopamine, nitric oxide, neuropeptide Y, vasoactive intestinal peptide, and adenosine may also play a role depending on the nerve location, type and disease state. Acetylcholine is the chief neurotransmitter of the PSNS, and acts on muscarinic and nicotinic cholinergic receptors. Parasympathetic nerve fibers that secrete ACh are referred to as cholinergic fibers.

General Role of ANS and Nerve Targets:

Experimental and clinical evidence shows that the autonomic nervous system, and more specifically the SNS, plays an important role in the pathogenesis of many diseases. Aberrant afferent signaling from organ receptors to the CNS can reflexively cause excessive efferent activity to specific target organs resulting in organ remodeling and disease progression. Such effects of excessive efferent and afferent activity may not be systemic throughout the body and may be localized to specific organs. Treating target sites within the body may reduce efferent and afferent SNS overactivity and restore autonomic balance.

For example, there is considerable evidence that essential hypertension is neurogenic and is initiated and by SNS overactivity. Various mechanisms have been proposed. They include the increased central sympathetic outflow, reduced local neurotransmitter (or catecholamine, norepinephrine) reuptake into neurons, lower arterial baroreflex sensitivity, and sympathetic neuromodulation by angiotensin II. Among these, reports by Schlaich et al., show that increased rates of sympathetic nerve firing and reduced neuronal NE reuptake are the major contributors for sympathetic overactivation; the role of angiotensin II and baroreflex restraint II are minimal. Hypertensive patients had higher nerve firing rated (increased muscle sympathetic nerve activity) and elevated total systemic, cardiac, and renal NE spillover levels. Their cardiac neuronal NE reuptake was also lower compared to normotensive subjects. In addition, the older patients showed greater neurogenic (neurotransmitter level) sensitivity to stress factors (like physical exercise, hypoglycemia or upright posture) compared to the young. The higher plasma NE levels, from enhanced SNA and neurotransmitter release, compensate for decreased functional response of the target organ to adrenergic stimulation, and cause organ damage and disease. Similar detrimental SNA overactivity, higher levels of neurotransmitters and resultant cellular remodeling is observed in other organs and organ tissue, and contribute to various medical conditions and chronic diseases.

Oral medication is the primary treatment for a many chronic diseases. Pharmacologic treatments for reducing SNS overactivity are not targeted to specific organs, organ systems; nerves nerve endings or physiological changes and produce a global reduction in SNA or systemic reduction in catecholamine or neurotransmitter levels. Such treatments may be inappropriate for non-target organs and organ systems and may not be effective where the disease mechanism is mediated by local activation and transport of neurotransmitters at specific nerve sites. Thus, targeting autonomic nerves innervating organs, at locations inside the body, may be more desirable to treat chronic diseases and improve organ function, compared to daily use of oral drugs. Drugs often have undesirable side effects, and patients are not compliant to their daily medication, both of which are significant problems facing healthcare. Methods are described to overcome these limitations and treat chronic diseases by local neuromodulation of sympathetic nerves, located in the cervical and thoracic ganglia of the sympathetic chain of the autonomic nervous system, and located within target organs and interconnecting nerve fibers, and through local administration of drug formulations.

Nerve locations inside the body include nerve bundles, nerve fibers or nerve clusters innervating organs, ganglia containing nerve bodies, nerve plexi (nerve junctions), and ganglionated plexi and glial cells. They also include portions of the nerve, including the nucleus, axon, Schwann cells, and the synaptic terminal. Agents may be delivered locally to a targeted nerve or portion of a nerve; to a ganglion, a portion of a ganglion or ganglia; to a nerve plexus, a portion of a nerve plexus or nerve plexi; to a ganglionated nerve plexus, a portion of a ganglionated nerve plexus or a nerve plexi at different anatomic locations inside the body. Examples of various disease states or medical conditions, treatment methods, formulations, and devices are described below.

Cardiac Medical Conditions and Therapies

Figure 1E:
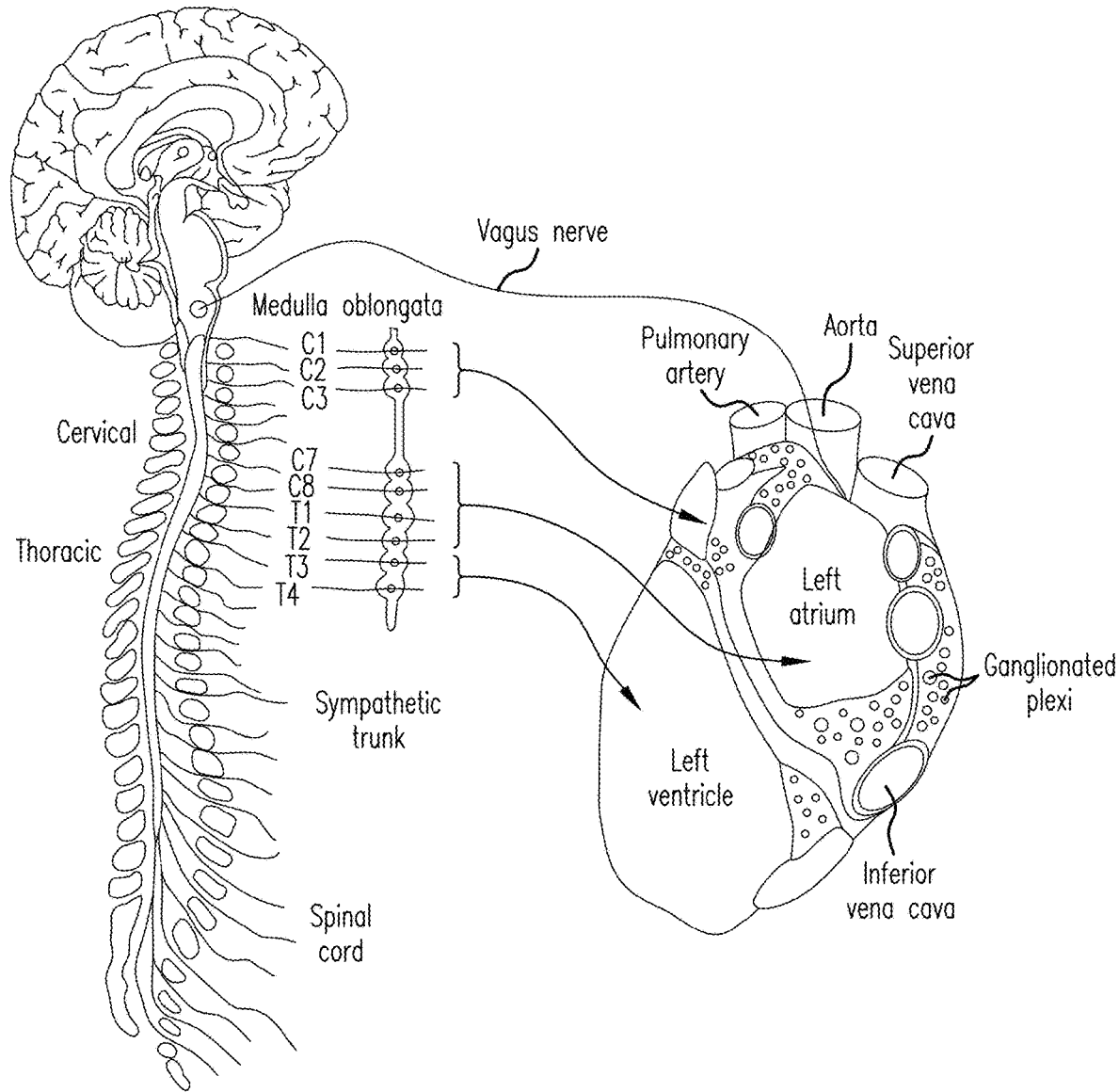
FIGS. 1E and 1F show the post-ganglionic extrinsic cardiac sympathetic nerves and intrinsic ganglionated plexi innervating the heart.
Figure 1F:
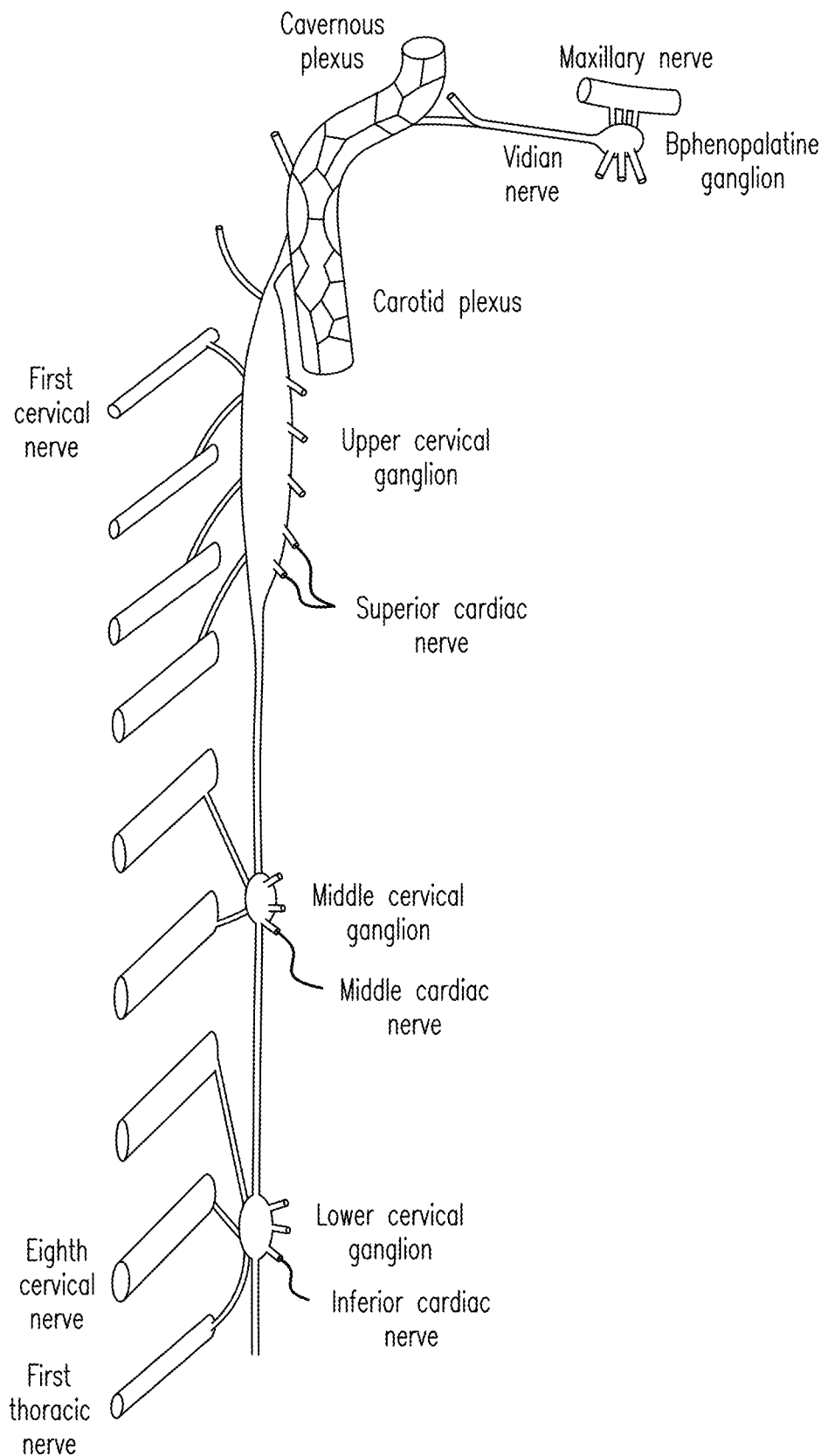

Cardiac Arrhythmias and Sudden Cardiac Death:

The cardiac nervous system consists of the extrinsic and intrinsic nervous component systems. The extrinsic cardiac nervous system (ECNS) provides sympathetic connections between the myocardium and the cervical, stellate and thoracic ganglia and parasympathetic connections between the atrial myocardium and the medulla oblongata, as shown in FIGS. 1E and 1F. Sympathetic innervation is provided by the superior cervical ganglia and the cervicothoracic (stellate) ganglia which communicate with the cervical nerves C1-C3, and with the cervical nerves C7-C8 to the thoracic nerves T1-T2. The thoracic ganglia (as low as at least the 4th thoracic ganglion) also contribute to the sympathetic innervation of the heart. The superior, middle, and inferior cardiac nerves from these ganglia innervate the heart by following the brachiocephalic trunk, common carotid arteries, and subclavian arteries. The thoracic cardiac nerves in the posterior mediastinum follow a more complex course to reach the heart in the middle mediastinum. Parasympathetic innervation to the heart is mediated by the vagus nerves. The vagal nerve fibers converge at a distinct fat pad between the superior vena cava and the aorta (known as the 'third fat pad') en route to the sinus and atrioventricular nodes.

The intrinsic cardiac nervous system (ICNS) is composed of a complex neural network of ganglionated plexi (GPs), which are concentrated within epicardial fat pads, interconnecting ganglia and axons in the heart (FIG. 1E). It is a network that transduces local cardiac signals and inputs from central neurons. Other regions that are richly innervated by the ICNS and have a high density of major GPs are the fat pads at the left and right pulmonary vein (PV)-atrial junctions and the along the ligament of Marshall. These pulmonary vein ganglia (PVG) serve as 'integration centers' for the right and left vagosympathetic trunks and modulate cardiac rhythm and AF inducibility. In addition to the major GPs, recent studies have shown there is an extensive atrial neural network composed of axons and ganglia (containing a small number of cholinergic, adrenergic, efferent and interconnecting neurons) scattered throughout the atrial parenchyma. This network is a peripheral extension of the intrinsic cardiac autonomic system directly connects with the sino-atrial node (SAN) controls heart rhythm. The sinus node is primarily innervated by the right-atrial GP, whereas the atrioventricular (AV) node is innervated by the inferior vena cava inferior atrial GP.

Figure 3A:
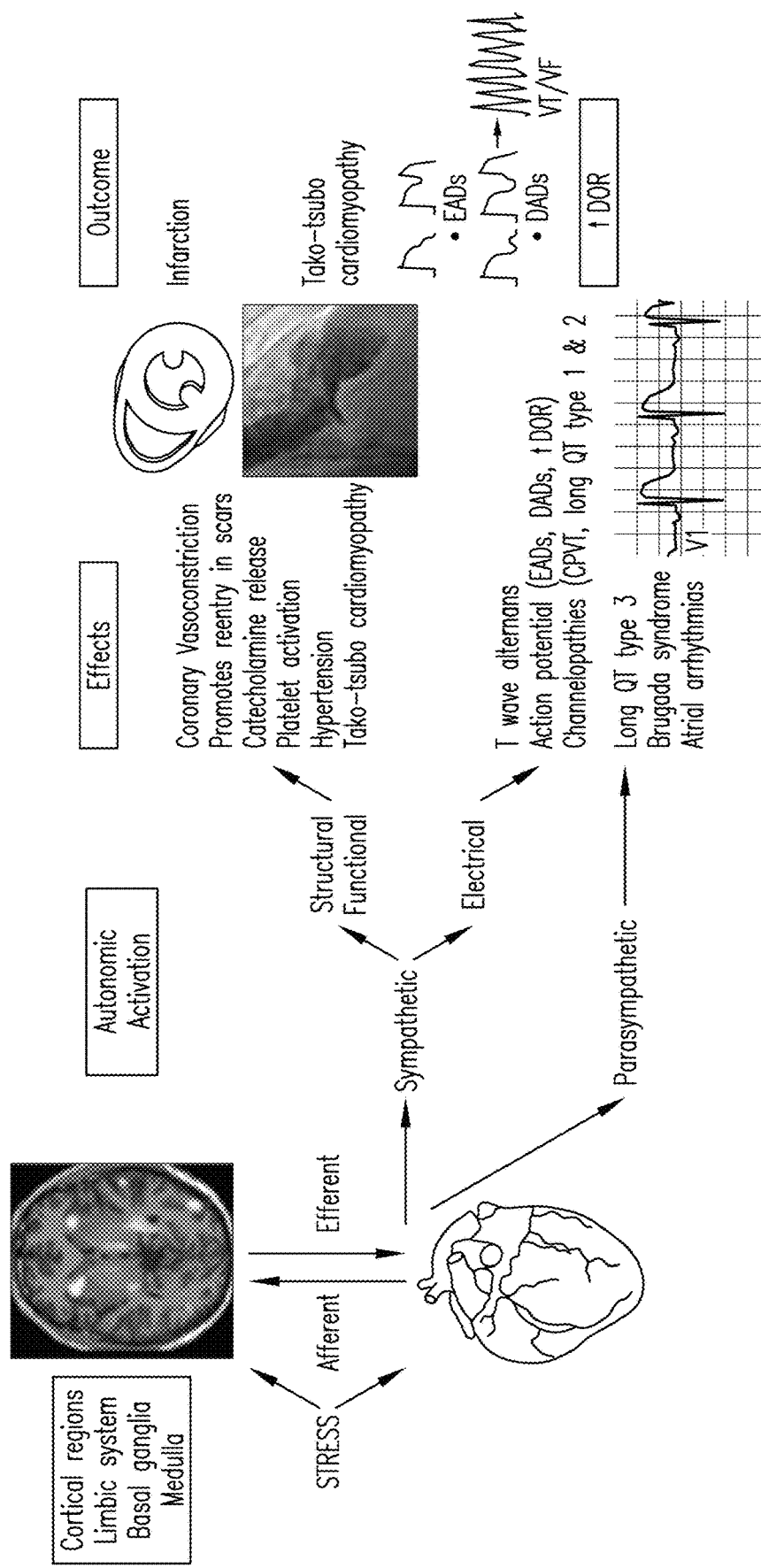
FIG. 3A shows the ANS interactions between the brain and the heart (mechanism of action) for the development of cardiac arrhythmias at the macroscopic level.
Figure 3B:
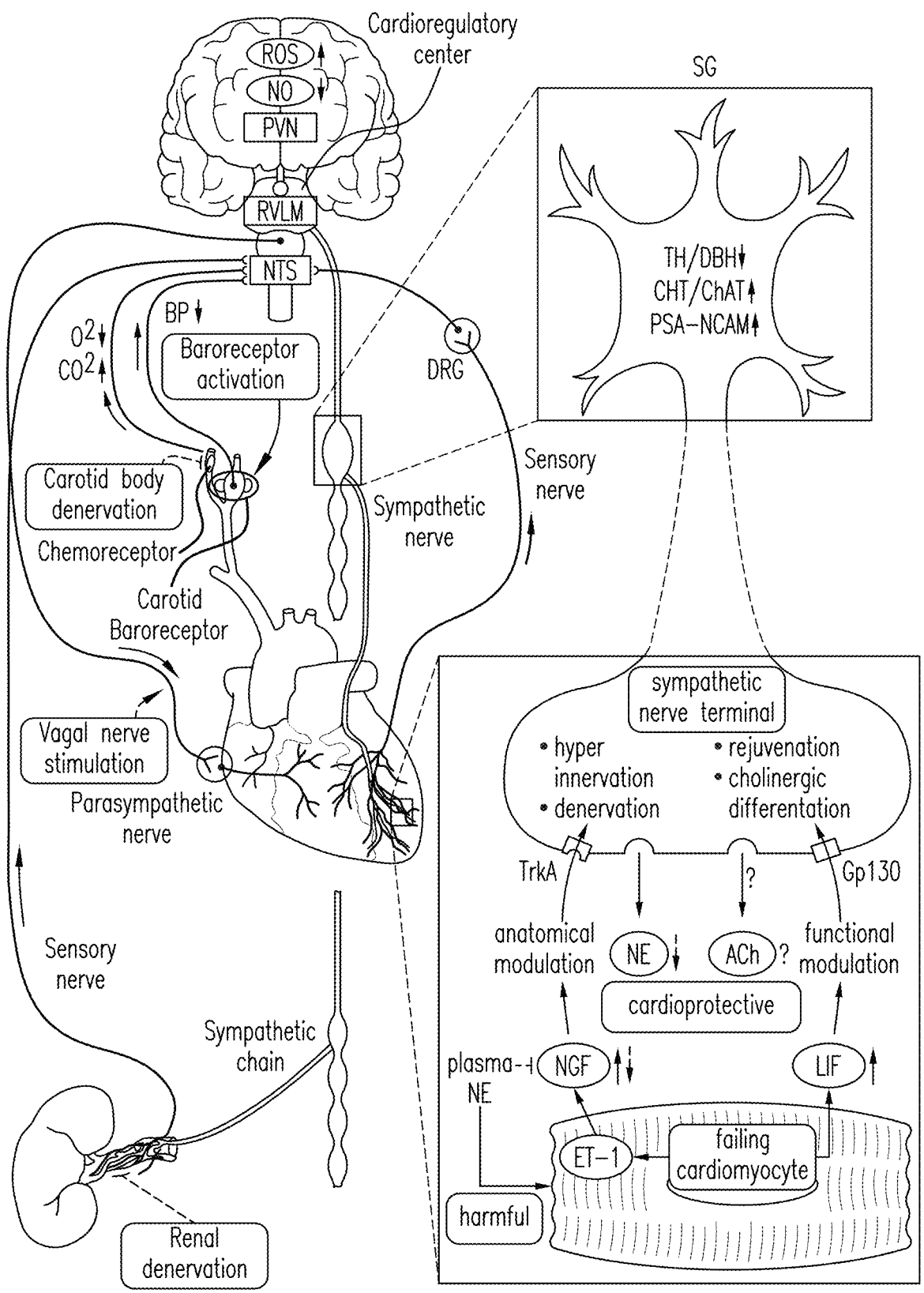
FIG. 3B shows the various sympathetic and parasympathetic nerve pathways involved with ANS dysfunction, nerve target sites for treatment, and mechanism of action at the microscopic/cellular level in the stellate ganglion and cardiac nerves in the heart.

The autonomic nervous system plays a major role in the pathophysiology of arrhythmias, both atrial and ventricular, and sudden cardiac death. Various autonomic pathways and interactions between nerves and organs at the macroscopic and microscopic level, are shown in FIGS. 3A and 3B, respectively. Therapies and therapeutic targets in development like carotid body denervation (carotid baroreceptors), cardiac ganglion (vagal nerve stimulation), and renal nerves (renal denervation) are also shown in FIG. 3B. Interactions between the brain and heart (neuro-cardiac axis), due to stress, emotion, exercise, metabolism, etc., can alter afferent and efferent cardiac signaling resulting in electrical and structural dysfunction of the heart. Negatively-charged emotion can result in sympathetically-mediated coronary ischemia, platelet activation, changes in hemodynamics, and catecholamine (NE) release. Coronary artery disease from atherosclerosis can also block the blood vessels supplying oxygen to the heart, resulting in heart attack or myocardial infarction (MI). Such electrical and mechanical disturbances along with inflammation, fibrosis, and genetics, can damage cardiac muscle (scar formation) and reduce the structural performance or pumping efficiency of the heart. Specific role of these electrical, structural, and autonomic remodeling in the development of atrial and ventricular arrhythmias is detailed below.

Atrial Arrhythmias:

The ICNS consisting of the major GPs and interconnected neural network in the atrium contributes to initiation of AF and progression to different states of AF-paroxysmal (PAF), persistent and long-standing persistent AF. Hyperactivity of the ICNS causes the release of excessive amount of acetylcholine and catecholamines and may lead to rapid firing from PVs or non-PV sites. Focal firing from GPs near PV roots (or PVGs) and left atrial appendage (LAA) has been associated with occurrence of PAF. Five GP anatomic sites known to be associated with AF and accessible from the left-atrial endocardium are the superior left GP (SLGP), anterior right GP (ARGP), inferior left GP (ILGP), inferior right GP (IRGP), and Marshall tract GP (MTGP). At the cellular level, the release of adrenergic neurotransmitters (like norepinephrine) mobilizes excess intracellular calcium leading to early after depolarizations (EADs), which can trigger ectopic firing of the PV cells. PVGs function as local integration centers between the heart and the ECNS as well as act independently to affect SAN automaticity and myocardial contractility functions.

Other (reentrant) forms of AF can also be initiated by myocytes with a significantly shorter action potential. The atrial neural network can be a major contributor in the progression from paroxysmal to persistent and longstanding persistent AF by providing additional sources of rotors (reentry circuits) as well as focal drivers for initiation and maintenance of AF. A gradient of atrial refractory periods (ARPs) is present from the PVG toward the atrial appendage and adjacent PV with a progressive decrease of ARP and increase of AF inducibility with GP activation. GP activation can also induce acetylcholine-mediated complex fractionated atrial electrograms (CFAEs) in the atrial myocardium, prior to the onset of AF, similar to the onset of AF at the PV-atrial junction.

Thus atrial arrhythmias may be associated with disturbances in ECNS and ICNS activity. Myocardial infarction (MI) induces morphological and neurochemical remodeling in the extrinsic stellate ganglion neurons, independent of infarct size, as reported by Ajijola et al, in preclinical models. Changes cause neuronal enlargement of adrenergic and non-adrenergic (cholinergic) neurons in both stellate ganglia as well as an increase in neuropeptide Y immunoactivity, neural cell adhesion molecule (NCAM, a binding glycoprotein) and choline acetyltransferase (ChAT) inside the stellate ganglion (SG inset of FIG. 3B); Tyrosine hydroxylase (TH) decreases locally in the ganglion. Abnormal signaling from the left stellate ganglion and the left thoracic vagal nerve of the ECNS causes AF and VF, as described in the following sections. However, bursts of activity in the ICNS, without input from ECNS or higher autonomic centers, can also trigger AF. Paroxysmal atrial tachycardia and atrial fibrillation episodes were invariably preceded by intrinsic cardiac nerve activity. Local administration of drug formulations may be used to correct the abnormal nerve signaling from the ECNS and ICNS. Drug formulations may be applied at or near the cervical ganglia, stellate ganglion, PVGs, cardiac fat pads containing the GPs, ganglia and plexi in the atrial neuronal network and interconnecting nerves, axons, and glial cells. In one embodiment a drug formulation may be applied at one or more locations to affect ECNS function. Drug formulations may be injected at or near the left stellate ganglion, right stellate ganglion, or both. In another embodiment, a drug formulation may be applied at one or more locations to affect ICNS function. In another embodiment, one or more drug formulations may be applied to treat the ECNS and ICNS.

Structural remodeling of heart from injury can result in scar tissue. Scar tissue can cause the systemic excitation of the neuroendocrine system and increase the production of hormones/catecholamines like norepinephrine (NE) and nerve-growth factor (NGF), as shown in FIG. 3B, near the sympathetic nerve terminal/junction between the cardiac nerve and cardiomyocyte (synaptic end of the extrinsic cardiac nerve originating at the stellate ganglion). The substances, along with circulating plasma NE levels, result in neurochemical remodeling, nerve sprouting (regrowth of nerves, reinnervation), or hyperinnervation in the myocardium resulting in local anatomical and functional neuromodulation at the cellular level. Cardiac hyperinnervation can also be caused by hypercholesterolemia, heart failure, and inflammation and is characterized by non-uniform increase in local nerve density. This process modifies the cardiac substrate and can lead to irregularities in the propagation of electrical impulses through cardiac tissue.

Myocardial ischemia and nerve regrowth act to lower the threshold for cardiac arrhythmias, leading to atrial fibrillation (AF). Once established, AF induces mechanisms for self-perpetuation CAF begets AF'). The arrhythmias also induce structural, electrical, and autonomic remodeling superimposed upon pre-existing abnormalities to increase susceptibility to recurrent and more persistent AF. For example, there are several peripheral GPs located on the periphery of the atria. These peripheral plexi can also become independently hyperactive, particularly when separated from the major GP as a result of acute injury or chronic scarring.

Therefore, blocking the production of NGF, NE and other catecholamines in cardiac nerve tissue through the local administration of drug formulations into the atrial myocardium can prevent nerve sprouting and preserve the health of the cardiac substrate. As a result, the patients have normal cardiac rhythm since the thresholds for AF inducibility are sustained and not lowered.

Radiofrequency (RF) ablation is currently used to treat atrial arrhythmias and has major limitations. Cardiac tissue ablation in the GPs has variable success rates; between 25-78% of patients were reported to be free from AF at one year. Pulmonary vein ablation to isolate them from the cardiac nervous system (referred to as pulmonary vein isolation, or PVI), alone or in combination with GP ablation, is also performed. PVI+GP ablation shows improved results. Atrial ablation of myocardial substrate, in regions that responsible for originating CFAEs, has also shown benefit to treat AF. But CFAE treatment effects are not durable and repeat ablation procedures are needed. Moreover, the ablation procedures are long. Some treatments require over 50 ablations and can take 3-4 hours. They damage surrounding tissue and the treatment effects are not durable. Clinical procedures are described that may be completed in less than 30 minutes. Drug formulations are targeted to act on neuronal circuits, conduction pathways, and tissue with reduced collateral damage. They alter feedback loops inside the body that are responsible for AF and provide durable treatment that lasts a few years.

Other treatment methods like low-level vagal nerve stimulation (LL-VNS), low-level carotid baroreceptor stimulation (LL-CBS) spinal cord stimulation (SCS) and renal denervation (RDN) are also in development to treat atrial arrhythmias. They involve the placement of multipolar electrodes, near at the T1-T4 level to stimulate the vagosympathetic trunk and the stellate ganglia T1 spinal level, connected to a neurostimulator which generates electrical pulses. Low level VNS, CBS, and SCS therapies are mediated by the parasympathetic branches of the ECNS. They restore autonomic balance by increasing the central vagal tone through electrical stimulation and decreasing the sympathetic tone via central reflex activation. While these therapies have demonstrated the feasibility to suppress AF inducibility, the procedures require invasive surgery for the implantation of expensive generators and electrical leads. Minimally-invasive and cost-effective methods are described for treating atrial arrhythmias. Renal denervation therapy, alone or in combination with PVI, also shows promise to treat AF. All treatments need further clinical studies to show sustained clinical benefit.

In another embodiment, local chemo-neuromodulation (LCN) may be combined with one or more of the above procedures to treat atrial arrhythmias by acting on the extrinsic and intrinsic cardiac autonomic nerve pathways at two different nerve locations inside the body. Combinatorial treatments may also be more effective in restoring autonomic balance between the sympathetic and parasympathetic feedback loops inside the body. Examples include LCN+SCS and LCN+CBS and LCN+RDN.

Ventricular Arrhythmias, Electrical Storm, Cardiac Arrest and Cardiac Death:

Disruption of the ANS may lead to ventricular arrhythmias involving increased extrinsic central sympathetic drive or decreased parasympathetic activity due to changes in density, distribution, excitability, and neurotransmitter content of the intrinsic efferent innervation of the ventricles. Sympathetic hyperinnervation and denervation are two prominent mechanisms responsible for ventricular arrhythmogenesis. Hyperinnervation occurs after injury to the myocardium from MI, heart failure or inflammation as described above; NGF production leads to non-uniform nerve growth, as described by Fukuda et al. and illustrated in FIGS. 3A and 3B. Denervation is also caused by MI, diabetic neuropathy and HF from release of proNGF, the precursor to NGF, and chondroitin sulfate proteoglycans which trigger axonal degeneration after myocardial infarction. Heterogeneities in cardiac innervation and resultant effect on SNA is the one of the main reasons for arrhythmias.

At the macroscopic level, myocardial injury increases the synaptic density of bilateral stellate ganglia of the ECNS. This increase in the ganglionic activity suggests remodeling of the extrinsic cardiac autonomic nervous system that can lead to chronic stimulation of sympathetic b-AR activity. Left stellate or right stellate ganglion stimulation is associated with ventricular tachyarrhythmias. Left cardiac sympathetic denervation (LCSD) through surgical excision of the stellate ganglion, 2nd thoracic ganglion and 3rd thoracic ganglion has been used to treat ventricular arrhythmias in high risk patients susceptible to sudden death.

At the cellular level, sympathetic activation of the ECNS releases NE, which binds to beta-adrenergic receptor (b-AR), activates protein kinase-A (PKA), phosphorylates several intracellular targets and leads to shortening of the action-potential duration (APD). Locally high NE concentrations also affect ion (calcium, sodium, potassium and protons) exchange and ion-channel function and cause focal arrhythmias. Shortening of APD during nerve conduction may increase the dispersion of repolarization (DOR) due to non-uniform innervation and resulting spatially non-uniform b-AR activation. These conditions are favorable for early after depolarizations (EADs) and delayed after depolarizations (DADs). EADs may contribute to increased DOR, and both EADs and DADs contribute to ectopic activity and focal arrhythmias. While EAD is believed to contribute to atrial arrhythmias, DAD induces arrhythmias in ventricular myocytes.

Hyperinnervation, nerve sprouting and localized release of NE (a b-AR agonist) affect the ICNS innervating the ventricle and increase the risk of ventricular arrhythmias. Chronic sympathetic denervation, on the other hand, can cause b-AR supersensitivity of myocytes, due to the down-regulation of G-protein receptor kinase 2 (GRK2, which inhibits b-AR during stimulation). The loss of GRK2 combined with increase in circulating NE levels sets up a positive feedback loop that renders the ventricular cardiac substrate arrhythmogenic. The local mismatch between the adrenergic receptors in the heterogeneous (hyperinnervated and denervated) myocardium prevents rhythmic signal conduction through the heart and causes arrhythmias. Cardiac nerves can also switch phenotype, i.e., transform from being adrenergic (NE-mediated signal conduction) to cholinergic (ACh-mediated nerve conduction) and render the cardiac substrate to be arrhythmogenic. Clinical studies with nuclear imaging have shown that sympathetic denervation (hypoinnervation) is a significant predictor ventricular arrhythmias, cardiac arrest and sudden cardiac death.

These remodeling processes or loops, if uncorrected, can further damage the ICNS in the cardiac substrate. The non-uniform sympathetic activation increases the likelihood of focal arrhythmia triggers like action potential gradients, (or gradients in APD), EADs, DADs or increased DOR, unidirectional conduction block, wave break, increasing the susceptibility to reentrant arrhythmia (ventricular tachycardia/ventricular fibrillation, VT/VF). Differential spatial APD patterns are observed in response to sympathetic stimulation (local NE levels) compared to circulating NE levels suggesting that the local heterogeneity in distribution of intrinsic ventricular nerve fibers is a factor in ventricular arrhythmias. During periods of high sympathetic activity, like exercise or stress, these factors can invoke a perfect storm of arrhythmic conditions that become uncontrolled due to the positive feedback loops and cause cardiac arrest and sudden cardiac death. Data from the American heart association show that the incidence of out-of-hospital cardiac arrest is nearly 7-fold higher in adults (between 50-79 years of age) with prior heart disease compared to healthy patients. Among heart disease patients, the risk of cardiac arrest was two-fold and four-fold higher in prior-MI and HF patients, respectively.

A study of 1275 health maintenance organization enrollees 50 to 79 years of age who had cardiac arrest showed that the incidence of out-of-hospital cardiac arrest was 6.0 per 1000 person-years in subjects with any clinically recognized HD compared with 0.8 per 1000 person-years in subjects without HD. In subgroups with HD, incidence was 13.6 per 1000 person-years in subjects with prior MI and 21.9 per 1000 person-years in subjects with HF.

Similar effects are noted on the ECNS induced stimulation of sympathetic activity. Differential changes in regional myocardial polarization are observed in animal models after stellate ganglion stimulation. Regional DOR was greatest on the anterior wall of the left ventricle and the apex with LSG stimulation. RSG stimulation causes the greatest dispersion on the posterior wall and posterior base of the right ventricle. Local DOR did not correlate with shortening in action recovery intervals suggesting that increased dispersion may be related to the sparse and heterogeneous innervation by stellate ganglia of the ECNS. Regional changes in DOR were consistent with T-wave changes observed during initiation of ventricular tachyarrhythmia.

Electrical storm (ES) is a more severe form of ventricular arrhythmia. It is a medical condition characterized by highly malignant and unstable episodes of VT or VF, usually three or more episodes within a 24 hour period. ES mainly affects patients with advanced dilated cardiomyopathy, both ischemic and non-ischemic, with gradual progression of disease in the arrhythmic substrate. It can also affect patients with structural heart disease (aortic or mitral valve regurgitation, valvular leaks or congenital heart disease), as well as patients without structural heart disease (e.g., Brugada syndrome).

Currently ventricular arrhythmias (VT, VF, and ES) and ES are treated using drugs and implantable cardioverting defibrillators (ICDs) to prevent the initiation and propagation of the local arrhythmias generated through neurohormonal, structural, and electrical remodeling processes occurring at the cellular level. Both ICDs and drugs are known to prevent VT, VF, cardiac arrest and sudden cardiac death. Beta blocker drugs reduce sympathetic activation, local NE production levels and arrest local arrhythmias. However, about 20-30% of patients are either not responsive or are intolerant to beta-blocker treatment. ICDs sense arrhythmias and, when they exceed a set threshold, send electrical shock signals into the ventricles and arrest the propagation of the arrhythmic wave by preventing the positive feedback loop from becoming uncontrolled. ICDs are very expensive and involve major surgery for implanting an electrical generator and conduction leads. In addition, ICDs have also been reported to provide inappropriate shocks, which are traumatic to patients, and affect their quality of life.

Treatments are described to overcome these limitations. In one embodiment of, a method is described to treat ventricular arrhythmias by reducing the extrinsic cardiac nerve activity and b-AR activation by treating the stellate ganglion, second thoracic ganglion and third thoracic ganglion through the administration of a drug formulation, locally at or near these ganglia and the interconnecting nerve chain fibers between them. The drug acts to block b-AR activity, attenuate stellate ganglion activity and reduce sympathetic stimulation of the heart through the ECNS. Formulations and methods to access and treat the stellate ganglion are described in the following sections.

In one embodiment, a drug formulation is injected locally at or near the left-stellate ganglion to treat ventricular arrhythmias. In other embodiments other ganglia of T2-T4 are also treated to reduce ANS activity and treat VTs. In some cases, the preganglionic fibers may extend to C7 and T5 ganglia. Methods and procedures are described to reach these ganglia and treat them by injecting small volumes of drug formulation. In other embodiments, the right stellate ganglion and its adjacent chain ganglia from C7 to T5 and the interconnecting nerve fibers may be treated.

Typically, nerve fibers from the left stellate ganglion widely innervate the posterior wall of the ventricles, and those from the right stellate ganglion are partially distributed in the anterior wall. However, cardiac disease (myocardial infarction and hypertrophy) can cause nerve sprouting to extend to regions normally innervated by the left and right stellate ganglia. In such cases, diagnostic sensing (nerve stimulation or cardiac imaging) may be used to confirm the nerve site location for treatment and determine if the unilateral-left or unilateral-right or bilateral stellate ganglion treatments are needed. For example, stimulation of the stellate ganglia (right or left) or the ansae subclaviae (right or left) may be performed to confirm target nerves that innervate the scar tissue surrounding the infarcted myocardium. Alternatively, the myocardium may be imaged using iodine-123 MIBG to assess the local degrees of cardiac denervation and/or innervation to determine if uni- or bilateral stellate ganglion treatment is needed. Stellate ganglion stimulation and MIBG imaging are described in following sections.

Another embodiment includes treating ventricular arrhythmias by local administration of drug formulations, described below, into the ventricular myocardium to reduce the heterogeneity of ICNS innervation and resultant sympathetic nerve signal transmission. The formulations prevent cardiac denervation and/or hyperinnervation to maintain autonomic balance and reduce b-AR supersensitivity and increase the thresholds for the initiation and propagation of VT and VF. Such formulations may be based on b-AR antagonists and other drugs as described in detail in the following sections.

Thoracic epidural anesthesia by injection analgesics (like clonidine), LCSD and renal denervation have been used to treat patients that are at high risk of death from VT/VF, cardiac arrest, electrical storm and sudden death. Analgesic effects are not long lasting and surgical procedures are invasive and expensive. These treatments are under investigation and used to treat high-risk patients that are refractory to conventional treatments; clinical trials are needed to establish their long-term benefit. Minimally-invasive and cost effective methods are described for treating ventricular arrhythmias which address these limitations.

Another pathway to correct cardiac autonomic imbalance is by stimulating the parasympathetic ECNS. Direct stimulation of the cervical pre-ganglionic parasympathetic fibers can enhance the cardiac vagal tone and prevent ventricular arrhythmias. Similarly, thoracic spinal cord stimulation (SCS) has demonstrated the potential to protect against ischemic ventricular arrhythmias in animal models. SCS also treated spontaneous non-sustained VT and sustained VT in an ischemia reperfusion model. Both approaches are invasive, expensive and involve the implantation of an electrical generator and leads. Minimally-invasive and cost effective methods are described for treating ventricular arrhythmias and preventing cardiac arrest or cardiac death which address these limitations.

Another embodiment includes neuromodulating the afferent nerves, located at the T1-T4 thoracic dorsal root ganglia, through local administration of drug formulations, described below. These nerve fibers transmit afferent nerve signals to the spinal cord. Interrupting the afferent signaling reflex modulates the sympathetic efferent output to the heart. Porcine studies show that unilateral disruption of cardiac afferent input to the spinal cord increased sympathetic tone to the heart, as noted by a reduction in action recovery interval (ARI) and tachycardia, during stellate ganglion stimulation. Bilateral disruption showed no difference in ARI or dispersion; a reduction in basal left-ventricular (LV) inotropic function and systolic blood pressure was noted.

Cardiac Channelopathies:

Channelopathy is a heart rhythm disorder that can potentially cause fast, chaotic heartbeats. It is caused by disturbed function of ion channel subunits of cells or the proteins that regulate ion channels. The disorders may be either congenital (due to mutations in the encoding genes) or acquired (from autoimmune attack on the ion channel). Examples of cardiac medical conditions affected by ion channel dysfunction include long QT syndrome (LQTS), catecholaminergic polymorphic ventricular tachycardia (CPVT), Brugada syndrome, and atrial arrhythmias. These conditions are most common in children and young adults and, if left untreated, can cause syncope, cardiac arrest and even sudden death. Current studies indicate that imbalance between parasympathetic and sympathetic nerve activity is one of the important triggers for the disease.

LQTS is a cardiac medical condition, characterized by abnormally long ventricular repolarization, and increases the risk of irregular heart beat that originates from the ventricles (ventricular tachyarrhythmias), also referred to as episodes of torsades de pointes (TdP). It is a neuronally-mediated disease that can lead to palpitations, syncope (fainting) and sudden death due to ventricular fibrillation, which can occur during conditions of physical or emotional stress. Normally the QT interval duration on an electrocardiogram (ECG/EKG) of a healthy person ranges between 350-440 milliseconds. LQTS patients are considered to be at high risk for arrhythmias, when their QTc (defined as the ratio of the QT interval to the square root of the RR interval) is greater than 500 milliseconds and low if QTc is less than 500 milliseconds.

LQTS may be genetic in origin resulting from gene mutation and different types of LQTS (Types 1 through 13) depending on the mutation type have been identified. Type 1 (LQT1) and Type 2 (LQT2) are the most common, associated with mutations in potassium ion channels, and make up about 50-65% of LQTS cases. Type 3 (LQT3) syndrome is associated with mutation in sodium ion channel. Sudden increases in sympathetic activity can lead to malignant VTs.

LQTS can also result from remodeling of the ICNS and ventricular substrate. EADs in LQTS patients are thought to be associated with reopening of L-type calcium channels during the plateau phase of the cardiac action potential. DADs are caused by an increased calcium-ion filling of the sarcoplasmic reticulum. Adrenergic (NE-mediated) stimulation can increase the activity of these channels. Afterdepolarizations can propagate to neighboring cardiac cells due to the differences in the refractory periods, leading to ventricular arrhythmias.

Malignant ventricular tachyarrythmias, associated with LQTS, can also be elicited by ECNS. Sudden increases in sympathetic activity, mostly mediated by the left stellate ganglion. Tissue samples of ganglia from stellectomy-treated patients suggest that inflammation (or T-cell mediated cytotoxicity) of the sympathetic ganglion cells may boost adrenergic activity and trigger or enhance electric instability.

Beta blockers are the first treatment of choice and are shown to be effective in preventing syncope in some patients. Additional treatments are necessary since 20-25% of patients continue to have syncopal episodes and remain at high risk for sudden cardiac death despite the use of beta blockers. ICDs are also implanted in LQTS patients, when beta blockers fail or are not well tolerated, to prevent VT and VF. ICDs also have significant side effects, especially among young people, and are costly. Left cardiac sympathetic denervation (LCSD), by removing left cervicothoracic or high thoracic left sympathetic ganglia (resection of the cervical sympathetic chain, also referred to as stellectomy), has been performed to treat patients suffering from LQTS and refractory to conventional treatment. Both stellectomy and ICD implantations are surgically-invasive procedures.

Minimally-invasive methods are described to treat patients suffering from LQTS by local neuromodulation of the left stellate ganglion through a one-time administration of a drug formulation, as detailed in subsequent sections. For some types of LQTS, both the left and right stellate ganglia may be treated by local injection of drugs to resolve cardiac arrhythmic events. In other embodiments, one or more or a portion of the cervical and thoracic ganglia may be treated using methods and formulations described below.

CPVT is another lethal cardiac ion channelopathy causing arrhythmias from ion-channel dysfunction and inappropriate handling of calcium release in cardiomyocytes due to unbalanced autonomic innervation of the heart. Like LQTS, it affects children and young adults. The arrhythmias cause syncope, seizure, cardiac arrest and sudden unexpected death (SUD). Nearly 30% of patients experience SUD as an initial presentation and up to 50% experience cardiac arrest by the age of 20-30. Although beta blockers are the standard therapy for CPVT, they are not well tolerated in some patients and treatment failure is reported in others. Limited studies have shown that CPVT patients can benefit from LCSD and placement of ICDs. Limitations on ICDs include cost and inappropriate shocks and the incidence of electrical storm in about 20% of patients. Both ICDs and LCSD are surgically invasive procedures. Minimally-invasive and cost-effective methods are described to treat CPVT.

Myocardial Infarction:

Patients who survive acute myocardial infarction (AMI) have a high incidence of ventricular arrhythmia and risk of sudden cardiac death (SCD). MI induces neural and electrical remodeling at scar border zones, as previously described, causing nerve sprouting (see FIGS. 3A and 3B). Acute arrhythmias may be caused by re-entry circuits in the damaged myocardium from coronary artery occlusion or reperfusion immediately after revascularization. Late ventricular tachycardias may result from re-entrant circuits in the healed-infarct and peri-infarct zones. Increased cardiac sympathetic activation worsens dispersion of repolarization (DOR) in the myocardium and renders it proarrhythmic. Studies have also shown that APDs and electrophysiological (EP) characteristics vary between myocytes in the three myocardial layers of the heart. The mid-myocardial myocytes have longer APDs than the epicardial and endocardial myocytes. Following myocardial injury, the EP characteristics of the ventricular substrate are altered by ICNS remodeling, which leads to the amplification of the DOR, causing ventricular transmural reentrant arrhythmias. In addition, various adrenergic receptors can mediate the cardiac ventricular EP effects from efferent sympathetic nerve activity relative to effects from circulating systemic NE levels.

Excessive ECNS sympathetic activity of the left stellate ganglion (LSG) nerve activity is also attributed to the initiation of ventricular arrhythmias. Stimulation or the infusion of nerve growth factor to the left stellate ganglion in dogs, that suffered MI, intensified the magnitude of LSG activity and caused a high incidence of SCD. Targeted attenuation of cardiac sympathetic neurons in the stellate ganglia reduced the incidence of MI-induced sustained VT in rats. Blocking the LSG activity in rabbits prolonged APD (in all three layers), reduced transmural DOR and increased the effective refractory period (ERP) and the ventricular fibrillation threshold (VTF). Thus reducing ECNS sympathetic activity may also benefit MI patients.

Currently patients suffering from myocardial infarction are treated using drugs, an interventional procedure or coronary artery bypass graft (CABG) surgery. Drugs are used to dilate arteries and increase blood supply and oxygen to the myocardium. A percutaneous coronary interventional (PCI) procedure, involving a balloon, stent, or a drug-eluting stent, is performed to open occluded arteries and restore blood flow. When the vessel blockages are complex, open CABG, off-pump CABG, or beating-heart surgical methods are used to treat patients and increase the supply of oxygen to the myocardium. However, a significant number of patients suffer episodes of atrial and ventricular fibrillation after these treatments.

Nearly 1 in 2 patients experiencing an acute MI (AMI), usually in the form of ST segment elevation MI (STEMI), are at risk of sudden cardiac death before receiving medical attention. Survival rates improved in the past two decades due to the increasing use drugs (beta-blockers, statins, angiotensin-converting-enzyme (ACE) inhibitors, angiotensin-II receptor blockers (ARBs), and anti-platelet drugs), rise in PCI procedures (reperfusion therapy to open blocked coronary arteries), and reduction in door to balloon time (improved medical attention). However, post-MI patients still have a life-long risk of ventricular arrhythmias and SCD that is nearly four times higher compared to the general population. Current in-hospital mortality rates after acute MI range between 5-6%; 1-year mortality rates range between 7-18%. Diabetic, dialysis, and kidney disease patients perform far worse, and nearly 70% of coronary artery disease (CAD)-related deaths in these populations present as cardiac arrest prior to presenting to hospital. A large study on patients treated by PCI after MI reported that 30-day, 1-year, and 5-year cardiac mortality rate were 7.3%, 8.4%, and 13.8%. The main causes of early death within 30 days are cardiogenic shock, brain damage (due to cardiac arrest) and malignant arrhythmia.

Malignant arrhythmias are reported in AMI and MI patients after PCI intervention. Secondary prevention of SCD can be achieved through ICD implantation, when malignant ventricular arrhythmias occur late (>48 h) after an MI, and are not due to reversible or correctable causes. Clinical guidelines for the primary use of ICDs to prevent SCD during the first 1-3 months after ST-elevation MI for patients who have low LVEF are evolving. ICDs may implanted in patients developing syncope or non-sustained VT, who have inducible sustained VT at the EP study, and in patients with an indication for a permanent pacemaker due to bradyarrhythmias. As noted, previously ICDS are invasive and expensive. Similarly, 20-40% of patients after cardiac surgery (coronary artery bypass grafting and cardiac valve replacement) suffer from abnormal heart rhythm 2-4 days after the procedure. This lengthens the hospital stay and Increases their risk of perioperative stroke and mortality. AF is the most common form of arrhythmia with onset occurring within 48 hours after surgery. The episodes may spontaneously convert to sinus rhythm or may persist over a week and require treatment to restore normal rhythm. HF and SCD accounted for nearly two-thirds of cardiac deaths in patients after trans-aortic valve replacement (TAVR). LVEF and new-onset persistent left bundle-branch block following TAVR were independent predictors of SCD.

Minimally-invasive methods are described to treat patients suffering from acute MI (with or without ST-segment elevation), angina, MI and cardiac valvular disease local neuromodulation of the left stellate ganglion through a one-time administration of a drug formulation, as detailed in subsequent sections. Not only does this treatment prevent the occurrence of VT/VF episodes, but it also resets the autonomic balance and decelerates the deterioration in the cardiac substrate and progression of disease. Attenuation of stellate ganglion activity may also be supplemented by the injection of a different drug formulation into regions of the ventricular myocardium to treat the maladaptive changes in the ICNS. In other embodiments, one or more or a portion of the cervical and thoracic ganglia may be treated using methods and formulations described below.

Treatments described may be used as an adjunctive treatment to other treatments like PCI and CABG. Stellate and thoracic ganglia may be preemptively treated by local chemical neuromodulation before coronary balloon angioplasty, stenting or bypass surgery to reduce post-interventional or post-surgical complications. Local drug administration may be done a few weeks to a few months, such as between 3 weeks to 3 months, prior to currently-accepted treatments for MI or valve repair to allow sufficient time for reduction in catecholamine levels.

Cardiomyopathy:

Cardiomyopathy (CM) is a medical condition associated with deterioration in the heart muscle, and its ability to contract and pump blood, leading to heart failure. It can take many structural forms—dilated, hypertrophic and restrictive, all of which impair heart pump function. Patients with CM are at risk for irregular heart rate and sudden cardiac death.

The use of ICDs to prevent sudden cardiac death has resulted in an increasing number of patients presenting with recurrent, appropriate ICD shocks for VT. Since pharmacologic therapy has not shown benefit, VT ablation is commonly used to treat patients with limited long-term efficacy and significant complications. The ThermoCool VT ablation trial reported recurrence of VT in 47% of patients at 6 months and a peri-procedural complication rate of 7.3%. Therefore, adjunctive or alternative treatment approaches are desirable in this patient population Since the modulation of the ANS can be used to treat ventricular arrhythmias, methods are described to treat cardiomyopathy patients by local neuromodulation of the left stellate ganglion through a one-time administration of a drug formulation, as detailed in subsequent sections. In some cases, both the left and right stellate ganglia may be treated by local injection of drugs to resolve cardiac arrhythmic events. In some cases, treatment may be administered at or near the stellate ganglion and in the myopathic cardiac substrate. In other embodiments, one or more or a portion of the cervical and thoracic ganglia may be treated using methods and formulations described below.

Heart Failure:

Heart failure is another ANS-mediated cardiac disease, influenced by complex neurohormonal mechanisms, which impairs the ability of the heart to pump blood. Most prominent among the neurohormonal mechanisms is the elevated adrenergic or SNS activity. In healthy hearts, the activation of ANS following cardiac injury restores cardiac function and output. For example, the SNS (adrenergic) branch of the ANS accelerates heart rate (positive chronotropy, predisposing to arrhythmias), increases cardiac contractility (positive inotropy) and cardiac relaxation (positive lusitropy), a decrease in venous capacitance, and constriction of blood vessels, all of which increase cardiac output as part of the body's fight-or-flight response. The parasympathetic (cholinergic) branch slows the heart rate (bradycardia) through vagal nerve impulses with minimal effect on cardiac contractility. Cardiac ventricles, that pump blood into the systemic and pulmonary circulations, are primarily innervated by adrenergic sympathetic nerves. Cholinergic parasympathetic fibers run alongside the vagus nerve sub-endocardially with minimal PSNS innervation to the ventricular myocardium. Thus, while heart rate can be controlled by SNS and PSNS, cardiac output is mostly controlled by the SNS. When the injury persists over time, the ANS is unable to maintain cardiac function; the hyperactive ANS activates the heart to work harder than the cardiac muscle can handle, resulting in a failing heart. ANS hyperactivity becomes a major problem in HF, conferring significant toxicity to the failing heart, and markedly increasing the morbidity and mortality of patients.

The cardiac neuronal system comprises afferent, efferent, and interconnecting neurons which behave as a control system. Afferent fibers project to the CNS by the autonomic nerves, whereas efferent impulses travel from the CNS to peripheral organs. The ANS outflow to the heart and peripheral circulation is regulated by cardiovascular reflexes originating from the aortic arch and the carotid baroreceptors and cardiopulmonary baroreceptors that are responsible for ANS inhibition, and cardiovascular low-threshold polymodal receptors and peripheral chemoreceptors, which are responsible for ANS activation.

ANS activation in the cardiovascular system is mediated by norepinephrine and epinephrine through the following steps: (a) NE is released by cardiac sympathetic nerve terminals located in the right stellate ganglion reaching the sinus and atrioventricular nodes (increase in heart rate and shortening of atrioventricular conduction) and through the left stellate ganglion reaching the left ventricle (increase in contractile strength), although NE release and reuptake can occur systemically throughout the heart and body; (b) epinephrine is released systemically into the circulation by the adrenal medulla, affecting both the myocardium and peripheral vessels; and (c) local release of NE and epinephrine by various peripheral ANS's that can synthesize and release these catecholamines in an autocrine/paracrine manner and are located in blood vessels and in cardiomyocytes.

Systolic HF is associated with neurohormonal hyperactivity as a compensatory mechanism to maintain cardiac output as cardiac function declines. Neuronal part is caused by ANS cardiac nerve terminals and the hormonal part is caused by increased secretion of NE, epinephrine, angiotensin II, and aldosterone hormones. ANS hyperactivity is noted as increased plasma NE and epinephrine levels, elevated (central) sympathetic outflow, and elevated NE spillover from activated cardiac sympathetic nerve terminals into the circulation. Systolic HF patients may, in fact, have a decreased ANS neuronal density and function, resulting in decreased NE concentration in the heart. Depletion of cardiac ANS neuronal NE stores (from reduced beta-adrenergic receptor density) and impaired neuronal NE reuptake via the NE transporter (from chronic overstimulation of adrenergic receptors) can cause a net enhancement of NE release and lead to worsening of HF failure, changes in receptor signaling, cardiac remodeling and sudden death.

Cholinergic remodeling can also occur in HF patients from neurotransmitter plasticity in the sympathetic ganglia in conjunction with postsynaptic receptors on cardiomyocytes, as noted by Fernandez and Canty. In the normal hearts, extrinsic cardiac nerves originating from the stellate ganglion secrete NE, increase heart rate and myocardial contractility through b1-adrenergic receptor signaling. The synaptic or interstitial NE level is the net amount of NE released and amount of reuptake. In HF patients, neuronal plasticity causes some cell bodies in the sympathetic ganglia to transdifferentiate into cholinergic type, expressing choline acetyltransferase (ChAT) causing a decrease in TH expression (see SG inset in FIG. 3B). The change from adrenergic to cholinergic type is promoted by NGF released from the myocardium, leukemia inhibitory factor (LIF) and cardiotrophin-1 expression. Lower NE reuptake and higher circulating NE levels (from sympathetic nerve overactivity) elevate interstitial NE and cause a reduction in the b1-receptor density and b-adrenergic signaling. In HF, cardiomyocytes also increase the expression of muscarinic (M2) receptors which can further reduce b-adrenergic activity and cause bradycardia and reduced contractility leading to diminished pumping inefficiency of the heart.

The role of chronic ANS activation in diastolic HF, without impaired left-ventricular ejection fraction (LVEF), is limited. ANS hyperactivity may contribute LVEF dysfunction in hypertensive patients and increase their risk to develop HF.

Patient symptoms of HF are classified according to the severity of their symptoms into four categories based on the New York Heart Association (NYHA) Functional Classification. Class I patients have no limitation of physical activity. Class II patients have mild limitation on physical activity. Ordinary physical activity results in fatigue, palpitation, or dyspnea (shortness of breath). Class III patients have marked limitation of physical activity and less than ordinary activities cause fatigue, palpitation, or dyspnea. Class IV patients are unable to carry on any physical activity without discomfort.

Medical management of chronic HF has shown benefit in some patients and is currently the best treatment of heart failure. Heart failure patients may need multiple medications including ACE inhibitors, ARBs, beta blockers and angiotensin-receptor neprilysin Inhibitors (ARNIs), hydralazine and isosorbide dinitrate, aldosterone antagonists, and diuretics.

Device-based therapies are used to supplement care in patients with advanced HF. Cardiac resynchronization therapy (CRT) is the most successful device-based therapy which improves the synchronization between the left ventricle and right ventricular apex through electrical stimulation (pacing) using an implantable generator and a lead, similar to an ICD. CRT is recommended in patients with a left bundle branch block (LBBB) pattern, LVEF<=35%, QRS duration >150 milliseconds, and class III or IV symptoms. A major limitation of CRT is that it cannot treat all HF population. It treats a quarter of HF patients that prolonged QRS duration; as many as 18-52% of patients receiving CRT are non-responders. Cardiac contractility modulation (to improve ventricular contractile function independent of QRS, by delivering a non-excitatory electrical signal during the refractory period of the cardiac cycle), vagus nerve stimulation (of preganglionic parasympathetic neurons in the brain stem), spinal cord stimulation (of the spinal nerve fibers leading to increased vagal tone and decreased sympathetic tone), carotid sinus stimulation (of the baroreceptors that activate efferent vagal nerve fibers), controlled interatrial shunts, and ventricular restoration devices are also in development. In extremely severe cases a left-ventricular assist device (LVAD) is also implanted as a bridge to a heart transplant or for long-term therapy. Heart transplant is the last option for patients that do not benefit from drugs and devices. As can be appreciated, all these treatments require invasive surgery, for the placement of an implant or electrical generator with leads, and are expensive.

Treatments are described which treat HF by affecting (the neurohormonal and electrical pathways of) the ANS through local neuromodulation of the stellate ganglion using drug formulations detailed in subsequent sections. One or both (left and right) stellate ganglia may be treated by local injection of drugs to affect the cardiac ANS, correct the cardiac conduction pathways, and improve left ventricular function of the heart to prevent cardiac arrest and sudden cardiac death. In some cases, drugs may be administered at two locations, the stellate ganglion and in the diseases cardiac muscle. In other embodiments, one or more or a portion of the cervical and thoracic ganglia may be treated using methods and formulations described below.

Chagas Disease:

Chagas disease is a tropical parasitic disease that is spread mostly by insects. It affects 7-8 million people in Mexico, South America, and Central America, and led to 12,500 deaths in 2006. The disease occurs in two stages, an acute stage and a chronic stage. The chronic stage disease symptoms develop 10-30 years after the initial infection (acute stage) in between 30-40% of patients. Among those, 20-30% of patients the chronic damage affects the ANS, digestive system, and the heart. Cardiac damage causes enlargement of the ventricles (dilated cardiomyopathy), heart rhythm disturbances, and heart failure. Patients are treated by drugs (amiodarone, beta blockers, ACE inhibitors, lidocaine and propafenone), ICDs, or cardiac tissue ablation.

Treating the ANS through renal denervation has been shown to reduce VT/VF episodes in patients suffering from Chagas disease despite the implantation of an ICD, refractory to medical therapy and cardiac ablation. Methods are described to treat cardiac and other ANS-mediated disorders caused by Chagas disease through neuromodulation of the ANS by local injection of drug formulations at or near the stellate ganglion, as described in the subsequent sections. One or both (left and right) stellate ganglia may be treated by local injection of drugs to affect the cardiac ANS, correct the cardiac conduction pathways, and improve left ventricular arrhythmias to prevent HF, cardiac arrest, and sudden cardiac death.

Other Cardiac Conditions:

Other ANS-mediated cardiac and cardiovascular disease conditions include angina, post-MI rehabilitation, microvascular ischemia, acute coronary syndrome, shock (hypovolemic, septic, neurogenic), valvular disease, cardiac structural abnormalities such as septal defects, myocardial contractility disorder, hypertension, orthopnea, dyspnea, orthostatic hypotension, dysautonomia, syncope, vasovagal reflex, carotid sinus hypersensitivity, and pericardial effusion.

Modulation of the autonomic nervous system (ANS) is emerging as an effective therapy to prevent such pathophysiological progress in cardiac disease. Various nerve targets have been identified as potential sites to modulate autonomic function. Examples include high-thoracic epidural anesthesia (HTEA), low-level vagal nerve stimulation, baroreflex stimulation, and renal nerve stimulation, ablation of GP in the heart, carotid body ablation, and stellate ganglion ablation. HTEA reduces afferent and efferent sympathetic nerve impulses to the heart and is used to stabilize cardiac electrical function. Bioelectric therapies, applied to the thoracic dorsal column or cervical to paravertebral sympathetic chain, can modulate ANS and reduce arrhythmias.

Methods are described to treat cardiac disease by locally neuromodulating the ANS, at nerve sites along the sympathetic chain of ganglia, that run along both (left and right) sides of the spinal cord and interconnecting nerve fibers nerves between them. Nerves, ganglia, plexi, ganglionated plexi, sympathetic nerves, and portions of ganglia, plexi, nerves, and nerve fibers inside the body are accessed using various devices, visualized and treated using drug formulations. Neuronal activity is monitored before, during, and after treatment to ensure completeness of treatment. Drug formulations are described that act on neuronal tissue and affect local ANS activity to treat cardiac disease without detrimental effects associated with systemic daily use of drugs, their side effects, and potential organ damage. Treatments are designed for a one-time administration of a small volume of the drug formulation at or near the nerve target sites to treat disease, and the efficacy is expected to last 1 day to over ten years, depending on the clinical application.

In one embodiment, a method of modulating the nerve activity at the cervicothoracic sympathetic ganglion (also referred to as the stellate ganglion) and nearby sympathetic nerves, nerve fibers, and neurons is described by locally delivering a drug formulation. Stellate ganglion ablation treatment was introduced in 1971 for adrenergically-mediated life-threatening ventricular arrhythmias to prevent sudden cardiac death. The procedure increases the threshold for causing arrhythmias by completely resecting the entire left stellate ganglion through surgery. In humans, the stellate ganglion is star-shaped structure, measuring about 1.5 cm3, situated lateral and posterior to the lateral edge of the longus colli muscle anterior to the first rib and posterior to the subclavian artery. It results from the fusion of the inferior cervical ganglion and the first thoracic ganglion into a single nerve body. While most individuals have a fused anatomy, unfused ganglia that lay in a similar area anterior to the transverse process of the C7 vertebra are also observed. Preclinical studies in dogs have shown that removing the stellate ganglion can increase VF thresholds, decrease cardiac excitability, and reduce the incidence of arrhythmias after myocardial infarction. In particular, the left stellate ganglion (LSG) is often the therapeutic target since left-sided cardiac sympathetic nerves have higher arrhythmogenic potential, increased dispersion of refractoriness, promote reentry and enhance automaticity. For example, NGF injection into the LSG caused sympathetic nerve sprouting, prolonged QTc interval and increased the risk of SCD (50%) in an experimental dog model. Similar NGF treatment on the right stellate ganglion shortened QTc and did not cause SCD, despite nerve sprouting.

Another method to regulate autonomic function by modulating cardiac nerves is left cardiac sympathetic denervation (LCSD), also referred to as high thoracic left sympathectomy (HTLS). LCSD involves surgical ablation or removal of the lower ½-⅔rd of the left stellate ganglion and the T2, T3, and T4 (and sometimes the T5) thoracic ganglia. This procedure provides adequate denervation and is associated with minimal effects of Homers syndrome.

Methods are described to treat the left stellate ganglion and nearby thoracic ganglia, sympathetic nerves, rami communicantes, nerve fibers, and portions of nerve or nerve fiber through the local administration of a small volume (for example, approximately 0.01-20 mL) of drug to modulate or ablate the lower half of the left stellate ganglion and T2, T3, and T4 thoracic ganglia. The drug may be administered using a needle under fluoroscopic (X-ray), CT, or ultrasound guidance to using the cervical and thoracic vertebral landmarks. Drug formulations, methods of administration, and visualization methods are described in detail in subsequent sections.

Drugs may be delivered locally into other anatomical locations of the heart to treat cardiac disease. The heart is innervated by endocardial, myocardial, epicardial, and pericardial nerve fibers. A small volume of a drug may be injected into selective regions within these layers. The pericardium is a protective sac which contains a small amount of fluid. Drug formulations described in the sections below may be injected into the pericardial sac to affect nerves or ganglia innervating the heart and restore autonomic balance.

Other anatomical targets inside the body may also be treated to regulate the autonomic nervous system and treat cardiac disease. For example, denervation of renal nerves near the kidney has been shown to decrease sympathetic nerve activity and plasma norepinephrine levels and treat atrial fibrillation. The carotid body is another target for modulating sympathetic nerve activity to treat heart failure.

Non-Cardiac Medical Conditions and Therapies

Pulmonary Hypertension:

Recent studies have shown that the SNS is activated in pulmonary arterial hypertension (PAH) patients, in addition to the known imbalance of vasoactive mediators like nitric oxide and arginase. Abnormal sympathetic hyperactivity has been shown to be an independent indicator in patients with PAH to show decreased functional capacity compared to those with normal sympathetic tone.

Most PAH patients are currently managed on oral drugs that are taken daily. Newer treatments are currently in development. Pulmonary artery denervation in the main pulmonary artery has been shown to treat PAH in experimental studies. Sympathetic ganglion block, by injecting a local anesthetic to the superior cervical ganglion, in rats (monocrotaline-induced PAH model) showed a reduction in the medial wall thickness of muscular pulmonary arteries compared to controls and attenuate the progression of PAH disease.

Methods are described to treat PAH through neuromodulation of the SNS and ganglia of the sympathetic chain. A small volume (for example, approximately 0.01-20 mL) of a drug may be administered at or near the left superior cervical ganglion to one or more of modulate, block, and ablate the nerves and reduce sympathetic nerve overactivity. Formulations are described in the following sections to achieve the desired extent of nerve modulation and the treatment time period. The drug may be administered using a needle under fluoroscopic (X-ray), CT, or ultrasound guidance to using the cervical and thoracic vertebral landmarks. Drug formulations, methods of administration, and visualization methods are described in subsequent sections.

Hot Flashes, Chronic Regional Pain Syndrome and Post-Traumatic Stress Syndrome:

Hormone replacement therapy (HRT) is currently in clinical practice for the treatment for hot flashes in symptomatic women with a clinical efficacy of 80%-90%. However, HRT is not recommended for patients with breast cancer. There are reports indicating that stellate ganglion block (SGB) for the treatment of vasomotor symptoms in symptomatic women, with a diagnosis of breast cancer are promising, may be effective.

Chronic or complex regional pain syndrome (CRPS), also known as reflex sympathetic dystrophy (RSD), is a medical condition that is characterized by pain, swelling, and vasomotor dysfunction of an extremity (limb, neck, chest, or head-termed CRPS Types I and II). It is often therapy-resistant with an unclear pathophysiology and unpredictable clinical course. Women are more affected than men. Sympathetic block is the currently used to treat CRPS. Nerve block of the stellate ganglion is achieved by repeated injections of a local anesthetic agent (lidocaine, bupivacaine, morphine), guanethidine, or by radiofrequency ablation, or by phenol neurolysis. Lumbar and cervical sympathetic blocks and plexus brachialis block are also performed using local anesthetic injections. Spinal cord and peripheral nerve stimulation (with surgically placed electrodes and generators) are also under evaluation. Sympathetic block treatments for CRPS, however, may not be durable; they also require multiple daily injections over several weeks. Implant-based therapies like spinal cord or peripheral nerve stimulation are invasive and expensive. Irradiation using linear polarized near-infrared light therapy has been used to treat CRPS with mixed results. Two out of six patients reported a reduction in pain, and four patients noted minimal or no improvement; no significant changes in autonomic function were noted. Besides, irradiation therapies are difficult to localize the treatment to the stellate ganglion and may damage surrounding tissue.

Post-traumatic stress disorder (PTSD) is a chronic anxiety disorder caused by seeing or experiencing traumatic events. Symptoms include anxiety, anger, or hypervigilance with clinically significant distress and/or functional impairment over an extended period of time. The SNS is known to be chronically activated (with higher NE levels in cerebrospinal fluid and urine) over the normal baseline levels in PTSD patients. Such high SNS activity among PTSD patients suggests that reducing noradrenergic activity in the central nervous system (CNS) could provide therapeutic benefit. Prazosin (a sympatholytic, alpha-adrenergic blocker) and clonidine (alpha-2 adrenergic receptor antagonist) are two drugs used to treat PTSD. Cervical sympathetic system modulation is also used to treat PTSD. The stellate ganglion and upper thoracic ganglion (T-2) are the upper sympathetic ganglions that innervate the upper chest, the head, and the brain. Many of the efferent sympathetic fibers from the thoracic ganglia (T-2) pass through the stellate ganglion. Clipping the sympathetic ganglia, via an endoscopic sympathetic block, at the T2 thoracic vertebra was found to be successful in treating PTSD. Studies on SGB, using a long-acting anesthetic in a group of nerves in the cervicothoracic ganglion, are also underway to treat PTSD.

Shingles (or herpes zoster) is a medical condition that is characterized by a painful and debilitating skin rash caused by the varicella zoster virus. It usually appears in a band, strip, or a small region of the face of the body. The virus causes chicken pox and following treatment stays dormant in the nerve roots. In some patients, the virus becomes active again through stress, age, and disease and weakens the immune system. Stellate ganglion block (SGB) and intercostal nerve block treatments are currently performed by pain specialists to treat pain from shingles.

Hyperhidrosis is a medical condition associated with excessive and unpredictable sweating even when the patient is at rest or the temperature is cool. The condition may be treated by antiperspirants and medications. More complex treatments involve underarm surgery to remove the sweat glands in the armpits by cutting, lasers, scraping, or liposuction. Iontophoresis therapy, using a gentle current of electricity, is also to treat sweating of the hands and feet. Injection of botulinum toxin into the underarm to block the nerves that stimulate sweating is also a treatment option; side effects include injection site pain and flu-like symptoms.

Endoscopic thoracic chain sympathectomy and stellate ganglion block are performed to treat severe forms of facial, palmar, and plantar hyperhidrosis. The second thoracic sympathetic ganglion is considered the major innervation center connected to the upper extremities, and hence, is the main target nerve site for nerve block or sympathectomy to treat hyperhidrosis. Surgical sympathectomy to treat palmar hyperhidrosis involves the removal or electrical cauterization or ablation of the T2 and/or T3 sympathetic ganglion. Compensatory hyperhidrosis (CH) is the most common complication of sympathectomy. Another technique involves a simple disconnection (excision) of the sympathetic chain between the T2 ganglion and the stellate ganglion, thereby preserving the ganglia. This procedure, known as sympathotomy or sympathicotomy, produces excellent results and clinically diminishes the chances of severe CH. Ramicotomy is another surgical procedure which disconnects or removes a section of the sympathetic (gray) rami, which connect the stellate ganglion to the brachial plexus, and treats hyperhidrosis, as shown in FIG. 1D. Both ramicotomy and sympathicotomy are under evaluation for the postoperative risk of severe CH.

Other complications of stellate ganglion block using a percutaneous needle-based approach or a video assisted thoracic approach include damage to the brachial plexus, trauma to the trachea and esophagus, injury to the pleura and the lung (pneumothorax or hemothorax), bleeding at the injection site, and hematoma. Airway compression and vasovagal can also occur along with infectious complications, when there is a breach in the aseptic barrier, including local abscess, cellulitis, and osteitis of the vertebral body and transverse process. Hoarseness of the voice due to paralysis of the recurrent laryngeal nerve and respiratory distress due to paralysis of the phrenic nerve are pharmacological complications associated with variabilities in the volume, dose, type, and exact injection site of the anesthetic formulation. Other adverse events may include seizures, loss of consciousness, hypotension, air embolism, and bradycardia.

Although the exact mechanism for hot flashes, CRPS, and PTSD are not exactly clear, it has been postulated that they could have common origins. In women, estrogen is known to regulate the production of nerve growth factor in sympathetic nerves. A decrease in estrogen leads to a nerve growth factor increase, which increases norepinephrine (NE) levels in the brain mediated by an overactive SNS. Stellate-ganglion block (SGB), results in a reduction in SNS activity and NE levels. This interaction leads to a reduction of many symptoms associated with these conditions. For example, nerve growth factor increases in pathological states with chronic stress. Hypoxia, neurogenic inflammation (by excretion of neuropeptides from nociceptive C-fibers) and sympathetic dysfunction are cited as potential causes for CRPS. Higher adrenergic SNS activity and circulating NE levels have been reported in PTSD patients compared healthy patients.

Methods are described to treat hot flashes through neuromodulation of the SNS and ganglia of the sympathetic chain. A small volume (for example, approximately 0.01-20 mL) of a drug may be administered at or near the left stellate ganglion to one or more of modulate, block, and ablate the nerves and reduce sympathetic nerve overactivity.

Methods are described to treat CRPS I and II conditions through neuromodulation of the SNS and ganglia of the sympathetic chain. A small volume (for example, approximately 0.01-20 mL) of a drug may be administered at or near one or more of the stellate ganglion, thoracic ganglia, lumbar ganglia, and the brachial plexus n to one or more of modulate, block, and ablate the nerves and reduce sympathetic nerve overactivity.

Methods are described to treat PTSD through neuromodulation of the SNS and ganglia of the sympathetic chain. A small volume (for example, approximately 0.01-20 mL) of a drug may be administered at or near one or more of the cervical ganglia, stellate ganglion, and thoracic ganglia to one or more of modulate, block, and ablate the nerves and reduce sympathetic nerve overactivity.

Methods are described to treat shingles through neuromodulation of the SNS and ganglia of the sympathetic chain. A small volume (for example, approximately 0.01-20 mL) of a drug may be administered at or near the stellate ganglion and/or the intercostal nerve to one or more of modulate, block, and ablate the nerves and reduce sympathetic nerve overactivity.

Methods are described to treat hyperhidrosis through neuromodulation of the SNS and ganglia of the sympathetic chain. A small volume (for example, approximately 0.01-20 mL) of a drug may be administered at or near the second (T2) and/or third (T3) thoracic ganglia to one or more of modulate, block, and ablate the nerves and reduce excessive sweating. Depending on the location and severity of hyperhidrosis, other target nerve locations for neuromodulation and nerve block include the sympathetic chain connections between the ganglia (e.g., the chain between T2 and T3 ganglia), the stellate ganglion, portions of the stellate ganglion, other thoracic ganglia, and chains between ganglia for the treatment of hyperhidrosis.

The drug may be administered using a needle under fluoroscopic (X-ray), CT, or ultrasound guidance to using the cervical and thoracic vertebral landmarks. Formulations are described to achieve the desired degree of nerve modulation over the treatment time period. For example, the nerves may be blocked temporarily for a few hours or a few weeks. Nerve function may be excited (upregulated) or impaired (downregulated) using drug compositions and concentrations. Nerves and nerve function may also be permanently impaired preventing nerve regrowth and regeneration. Drug formulations, methods of administration, and visualization methods to achieve the above are described in detail in subsequent sections.

Stroke and Vasospasm:

Stroke is a major cerebrovascular disease that is caused by a blocked blood vessel or bleeding (hemorrhage) in the brain. Specifically, cerebral vasospasm after aneurysmal subarachnoid hemorrhage (SAH) can cause a 1.5- to 3-fold increase in mortality within the first 2 weeks after SAH. When patients survive stroke, it is the major cause of major disability, with a 25% reduction in excellent outcome. Current treatments for cerebral vasospasm consist of hypervolemic, hypertensive, hemodilutional (HHH) therapy, and neuroradiological procedures. These treatment options have technical limitations and have demonstrated significant variability in clinical outcomes.

New approaches targeting the ANS, with temporary block of the intracranial autonomic sympathetic inflow, have shown to improve cerebral blood flow in humans and preclinical models. Perivascular sympathetic nerves play an active role on the regulation of cerebrovascular resistance. The cerebral vasculature in the pial vessels is densely supplied by noradrenergic sympathetic nerve fibers originating in the superior cervical ganglion, running along the carotid artery, and projecting into the ipsilateral hemisphere. Intracerebral vessels constrict in response to cervical sympathetic stimulation and dilate when the nerve fibers are blocked. Ganglion blockade decreased the systolic blood pressure and cerebral blood flow in healthy human subjects suggesting autonomic neural control of the cerebral circulation. Cervical sympathetic ganglion or nerve block, at the level of the superior cervical ganglion, of the ascending cervical sympathetic chain, using a local anesthetic agent (bupivacaine, clonidine and/or propranolol) or an adrenergic blocker (norepinephrine, tyramine, phentolamine), has been shown to prevent worsening and reverse neurological symptoms in patients suffering from cerebral vasospasm. This technique may be used as a primary therapy or as an adjunct to the standard therapy to improve cerebral perfusion and treat neurological symptoms.

Increased or altered autonomic activity has also been cited as a mechanism by which intracranial hemorrhage produces myocardial damage and cardiac arrhythmias. Atrial and ventricular arrhythmias and various degrees of A-V block were reported in patients suffering from SAH and animals after intracranial hemorrhage. Thus, autonomic nerve blockade in patients with intracranial hemorrhage may also be useful in preventing myocardial damage and cardiac arrhythmias.

Methods are described to treat hemorrhagic stroke and resultant cardiac medical conditions (arrhythmias, myocardial infarction, etc.) through local chemical neuromodulation of the ANS, ganglia and nerve fibers of sympathetic chain. A small volume (for example, approximately 0.01-20 mL) of a drug may be administered at or near the cervical ganglia or the stellate ganglion to one or more of modulate, block, and ablate the nerves to vasodilate the cerebral arteries and increase blood flow and oxygen supply to the brain. The treatment may also be used to treat patients that suffered a recent non-hemorrhagic stroke by increasing oxygen supply to the brain, through vasodilation and enhanced microcirculation within collateral channels, induced by ganglion or nerve blockade.

The drug may be administered using a needle under fluoroscopic (X-ray), CT, or ultrasound guidance to using the cervical vertebrae as landmarks. Formulations are described to achieve the desired nerve block degree and treatment period. For example, the nerves may be blocked temporarily for a few hours, weeks or months. Nerves and nerve function may also be permanently impaired preventing nerve regrowth and regeneration. Drug formulations, methods of administration, and visualization methods to achieve the above are described in detail in subsequent sections.

Pain—Trigeminal Neuralgia:

Trigeminal neuralgia (TN) is a neuropathic pain medical condition that affects the trigeminal or fifth cranial nerve due to nerve injury or nerve lesion. Typically, Type 1 or TN1 is characterized by extreme, sporadic, burning or shock-like facial pain that lasts a few seconds to two minutes per episode. Such episodes can occur in succession and last up to two hours. Another form (Type 2 or TN2) is characterized by constant aching and stabbing pain of lower intensity than Type 1. Both pain forms may occur in the same person, sometimes at the same time, and the intensity can be physically and mentally incapacitating.

The trigeminal nerve is one of twelve pairs of nerves that are attached to the brain. The nerve has three branches that conduct sensations from the upper, middle, and lower portions of the face, as well as the oral cavity, to the brain. The ophthalmic, or upper, branch supplies sensation to most of the scalp, forehead, and front of the head. The maxillary, or middle, branch stimulates the cheek, upper jaw, top lip, teeth and gums, and to the side of the nose. The mandibular, or lower, branch supplies nerves to the lower jaw, teeth and gums, and bottom lip. More than one nerve branch can be affected by this medical condition.

Current treatments for TN include oral anticonvulsant drugs (carbamazepine, oxcarbazepine, gabapentin etc.), tricyclic antidepressants (amitriptyline or nortriptyline). Common analgesics and opioids are not helpful. Medications are not always effective and can have considerable side effects. Neurosurgical procedures (rhizotomy or rhizolysis) are also performed to damage the cranial nerve fibers and block pain. Several forms of rhizotomy are available including balloon compression (to squeeze a portion of the nerve against the hard edge of the brain and the skull), glycerol injection near the trigeminal nerve center (or ganglion, the central part of the nerve from which the nerve impulses are transmitted to the brain), radiofrequency thermal lesioning (heating the nerve using electrodes), stereotactic radiosurgery (using Gamma Knife, Cyber Knife focused beam of energy to create lesions on the nerve to disrupt the transmission of sensory signals) and microvascular decompression (involving invasive surgery to move the artery or tissue compressing the nerve by placing a soft cushion between the nerve and vessel). A partial resection of the nerve or neurectomy may also be performed. Among these, microvascular decompression treatment surgery is the most durable; about half of the patients are relieved of pain for 12-15 years. All other treatments are effective for 1-3 years. Accordingly, there is a need for newer treatments that are less invasive and more durable.

Methods are described to treat TN through neuromodulation. A small volume (for example, approximately 0.01-20 mL) of a drug may be administered at or near one or more of the trigeminal nerve, stellate ganglion, branches of the TN, and nerve fibers to one or more of modulate, block, and ablate the nerves and reduce sympathetic nerve overactivity. A small volume of a drug formulation may be administered at or near the stellate ganglion to cause a nerve block for a prolonged period, lasting a few days to several months or years to treat Bell's palsy and other orofacial pain syndromes including neuropathic orofacial pain.

The drug may be administered using a needle under fluoroscopic (X-ray), CT, or ultrasound guidance. Formulations are described to achieve the desired degree of nerve modulation over the treatment time period. Nerves and nerve function may also be permanently impaired preventing nerve regrowth and regeneration. Drug formulations, methods of administration, and visualization methods to achieve the above are described in detail in subsequent sections.

Pain—Cancer, Chronic Pain and Post-Surgical Recovery Pain:

Most patients suffering from cancer experience pain. Acute and chronic pain can be nociceptive (mediated by mechanical, chemical, and thermal stimuli) or neuropathic (mediated by the dysfunction of nervous system). Nociceptive pain can be somatic pain or visceral pain. Somatic pain is mediated by the somatic nervous system, which innervates the skin, bone, and muscle, and is sharp, aching, or throbbing. Visceral pain is mediated by the ANS, which innervates internal structures such as the gastrointestinal tract, and is often difficult to localize or describe and sometimes characterized as crampy. Neuropathic pain can be either peripheral or central. The nerves may be damaged by ischemia, compression, infiltration, metabolic injury, or transection. For example, neuroma may be formed after thoracotomy due to aberrant healing after surgery. Neuropathic pain may involve dysfunction of the nervous system.

Repetitive nociceptive pain stimuli can cause increased sensitivity of the spinal cord neurons (known as central facilitation) without structural damage to the nerves. Neuropathic pain tends to be associated with burning, tingling, numbness, shooting, stabbing, or electric-like feelings.

A three-step management of cancer pain based on World Health Organization (WHO) guidelines is in practice today. Patients with mild pain (Step 1, with a pain score of 1-3 on a 10-point numerical scale) are treated by aspirin, acetaminophen, non-steroidal anti-inflammatory drugs (NSAIDs), and adjuvants. Adjuvants are co-administered to enhance analgesia and manage the adverse effects of drugs and opioids. Patients with moderate pain (Step 2, with a pain score of 4-6) are treated by aspirin or acetaminophen, codeine, hydrocodone, oxycodone, dihydrocodeine, tramadol, and adjuvants. Patients with severe pain (Step 3, with a pain score of 7-10) are treated by morphine, hydromorphine, methadone, levarphanol, fentanyl, oxycodone, non-opioid analgesics, and adjuvants. Drugs may be administered via oral, intravenous, intramuscular, enteral, subcutaneous, parenteral, or intraspinal routes to obtain desired pain relief. These pharmacological regimens have significant side effects causing patients, especially cancer patients, with significant discomfort and compromise in their quality of life. Constipation, dry mouth, nausea, vomiting, sedation, and sweats are common side effects; delirium, hallucinations, and urinary retention are rare but reported. Such limitations could be minimized by administering a significantly small dose/volume of drug locally at or near target nerve fibers associated with pain. Secondly, the continued use of opioid analgesics for pain management following significant surgery, arthritis, migraines, and chronic back pain can lead to drug addiction, which is a significant healthcare and social problem in the United States.

About 20-30% of cancer patients are refractory to pain medication or have excessive side effects. An interventional approach to treating pain is recommended by WHO for those patients. For example, the celiac plexus block is commonly used to treat upper abdominal pain in patients suffering from pancreatic cancer. The celiac plexus block involves autonomic neural blockade of the sympathetic axis by infusing a local anesthetic agent like lidocaine or bupivacaine. This may be followed by the superior hypogastric plexus block and the ganglion of impar block for patients with lower abdominal or pelvic pain. For patients with regional pain, a peripheral nerve block can be applied to any peripheral nerve, including the femoral, sciatic, paravertebral, brachial plexus, and interpleural nerves. For patients with severe pain, neural blocks are considered the primary mode of treatment.

Typically, the anesthetic drug is administered at the target nerve or tissue site inside the body, once or twice (as a bolus) and then, the nerve/tissue is continuously infused with drug for a few days to weeks using a catheter. When longer infusions are needed, an implantable drug pump is used to provide pain relief. Current drugs have significant side effects and, in some cases, the treatments may not effective. Moreover, the catheters and implantable devices are inconvenient to cancer and terminally ill patients that suffer from severe pain. Thus, new treatment methods and drug formulations are needed to manage and treat pain in cancer patients and patients recovering from complex surgery, that are safe and effective, to permanently block the target nerves and provide durable pain relief without the inconvenience of intubated devices or undesirable side effects from drug infusions.

Methods are described to treat chronic pain through neuromodulation. A small volume (for example, approximately 0.01-20 mL) of a drug may be administered at or near the target nerve or tissue location to one or more of modulate, block, and ablate the nerves and reduce sympathetic nerve overactivity. The drug formulation may be administered at or near the stellate ganglion to treat neuropathic pain syndromes in cancer patients to achieve sustained pain block, over a period of days to months. The drug may be administered using a needle or a catheter under fluoroscopic (X-ray), CT, or ultrasound guidance. Formulations are described to achieve the desired degree of extent of nerve modulation over the treatment time period. Nerves and nerve function may also be permanently impaired preventing nerve regrowth and regeneration. Drug formulations, methods of administration, devices, and visualization methods to achieve the above are described in detail in subsequent sections.

Dermatology, Goiter and Fibromyalgia:

Goiter is a medical condition caused by enlargement of the thyroid gland, more commonly affecting women. In some cases, the goiter may disappear on its own or become larger and may stop making thyroid hormone, a condition that is called hypothyroidism. In some cases, a goiter becomes toxic and produces thyroid hormone on its own increasing hormone levels, a condition referred to as hyperthyroidism. Fibromyalgia is a medical condition or disorder that causes widespread pain and fatigue. Stellate ganglion block using bupivacaine and guanethidine has been used to treat fibromyalgia patients with mixed efficacy. Bilateral stellate-ganglion irradiation using xenon-light also showed an improvement in pain score immediately after treatment. Long-term durability and potential damage to surrounding tissue are the major limitations; patients are expected to receive treatment at regular intervals.

Other Conditions—Hypertension, Etc.

Medical conditions like hypertension, chronic and vascular insufficiency, and vascular disorder of the upper extremities such as Raynaud's disease, intra-arterial embolization, and vasospasm may be treated. Lymphatic drainage and edema of the upper extremity following breast surgery, post-herpetic neuralgia, phantom limb pain, and amputation stump pain may also be treated. Quinine poisoning, Meniere's disease (spontaneous episodes of vertigo, fluctuating hearing loss and feeling of pressure or fullness in the ear), tinnitus (ringing in the ear) and vascular headaches, like cluster and migraine headaches, may also be treated.

A small volume of a drug may be administered at or near the stellate ganglion or ganglia of the sympathetic chain or nerves in between or portions of ganglia or nerves and nerve fibers to achieve nerve block of sufficient duration. They may be effective for a day and longer-lasting than an anesthetic without concomitant side effects. Such treatment may last a few weeks, months, or years depending on the drug formulation and drug release kinetics, as described in the following sections. A nerve block may last between one to eight weeks. Examples of target medical conditions and nerve target sites are listed in the Table 1 below.

TABLE 1

Treatment of Medical Conditions and Nerve Target Sites
(One or more sites)

| Medical Condition | Target Nerve Locations |
|---|---|
| Cardiac | |
| Atrial arrhythmias | Stellate ganglion, ganglionated plexi, atrial myocardium, pulmonary veins, cardiac fat pads, rami communicantes |
| Ventricular arrhythmias | Stellate ganglion, cervical ganglion, ventricular myocardium, dorsal thoracic nerve fibers, pericardial sac; rami communicantes |
| Sudden cardiac death | Stellate ganglion, C7-T2 sympathetic ganglia; rami communicantes |
| Myocardial infarction | Stellate ganglion, cardiac substrate, C7-T2 sympathetic ganglia; rami communicantes; atrial or ventricular myocardium |
| Angina | Stellate ganglion, C7-T2 sympathetic ganglia; rami communicantes; atrial or ventricular myocardium |
| Heart failure | Stellate ganglion, C7-T2 sympathetic ganglia; rami communicantes; atrial or ventricular myocardium |
| Cardiomyopathy | Stellate ganglion, C7-T2 sympathetic ganglia; rami communicantes; atrial or ventral myocardium |
| Chagas disease | Stellate ganglion, C7-T2 sympathetic ganglia; rami communicantes |
| Channelopathies | |
| Long QT syndrome, CPVT | Stellate ganglion, C7-T2 sympathetic ganglia; rami communicantes |
| Brugada syndrome | Stellate ganglion, C7-T2 sympathetic ganglia; rami communicantes |
| Fibromyalgia | Stellate ganglion, C7-T2 sympathetic ganglia; rami communicantes |
| Short QT syndrome | Stellate ganglion, C7-T2 sympathetic ganglia; rami communicantes |
| Tinnitus, Seizures | Stellate ganglion, C7-T2 sympathetic ganglia; rami communicantes |
| Pain | |
| CRPS | Stellate ganglion, C7-T2 sympathetic ganglia; rami communicantes |
| Cancer | Nerves innervating the target tumor tissue |
| Trigeminal neuralgia | Stellate ganglion, branches of trigeminal nerve |
| Surgical pain | Nerves affected by surgery |
| Chronic pain | Nerves and nerve fibers near target pain locations |
| Hot flashes | Stellate ganglion, C7-T2 sympathetic ganglia; rami communicantes |
| PTSD | Stellate ganglion, C7-T2 sympathetic ganglia; rami communicantes |
| Stroke | Stellate ganglion, C7-T2 sympathetic ganglia; rami communicantes |
| Other | |
| Goiter | Stellate ganglion, C7-T2 sympathetic ganglia; rami communicantes |
| Raynaud's disease | Stellate ganglion, C7-T2 sympathetic ganglia; rami communicantes |
| Meniere's disease | Stellate ganglion, C7-T2 sympathetic ganglia; rami communicantes |

Drug Neuromodulatory Effects: Mechanism of Action

Neuronal noise is a general term that is defined herein as random influences on the transmembrane voltage of single neurons, and by extension, the firing frequency of neural networks. This noise can influence the transmission and integration of signals from other neurons, as well as, alter the firing activity of neurons in isolation. This noise can also affect innervated tissue homeostasis and generate disturbances in cell signaling and physiology. Perturbation of neuronal noise can lead to, or is associated with, disease states listed above.

Ion Pump and Ion Channel Antagonists:

Ion channels are ion-permeable pores in the lipid membranes of all cells. The channels open and close in response to stimuli, and thus gate the flow of specific small ions. The ions flow downhill thermodynamically to enter or egress cells.

Ion pumps are non-ion permeable pumps in the lipid membranes of all cells that use chemical energy (in the form of adenosine triphosphate (ATP) hydrolysis) to power the transport of ions against an electrochemical gradient (uphill, thermodynamically).

Both ion channels and ion pumps are highly abundant on cells in a ganglion, as ion homeostasis (the regulation of ions that enable maintenance of normal cellular responses) is a hallmark of a neuron. Indeed, the average charge difference across a neuronal membrane when at rest (−70 mV) differs significantly from the charge difference across the membrane of an actively firing neuron (30 mV). The neuron utilizes both ion channels and ion pumps for membrane depolarization (opening of sodium channels) and repolarization (opening of potassium channels). The Na+/K+ pump is responsible for maintaining the electrochemical gradient of the resting potential (−70 mV). Perturbations in its activity can lead to prolonged resting periods, cessation in neuronal firing (block) and/or death.

Conductance fluctuations in ion channels are driven by thermal fluctuations, and in some sense, amplify these fluctuations. These protein channels are made up of subunits and complex domains that weave in and out of the cytoplasmic membrane, and undergo spontaneous changes in conformations between various open and closed states in a heat-influenced manner. The open state is characterized by a pore that allows specific types of ionic species to migrate through the membrane, under the influence of an electrochemical driving force. Such a force arises due to gradients in voltage and ionic concentration across the neural membrane. In a neuron where there are a large number of channels, single channel fluctuations have minimal impact on neuronal ion homeostasis. When the number of channels is not large, single channel fluctuations can be described by a Markov process and can lead to action potentials (Strassberg and DeFelice, 1993). Similarly, in a neuron where there are a large number of channels, it requires multiple channels to undergo fluctuation to lead to action potentials.

The main component of the noise experienced by a neuron originates in the myriad of synapses made by other cells onto it. Every spike arriving at this synapse contributes a random amount of charge to the cell due to the release noise. During the time a channel is open, ions migrate in complex ways and varying amounts across the membrane. The associated fluctuations are called channel shot noise. Continued perturbations may lead to downstream dysfunction within a neuron and downstream from said neuron.

Discussed herein are drugs that may be used to regulate ion flow by agonistic or antagonistic interaction with ion channels or ion pumps to reduce shot noise, synaptic noise, or to regulate neuronal activity in the ANS.

In some embodiments, it may be advantageous to contact a tissue with a channel blocker to affect ganglionic activity in the adjacent tissue. In other embodiments, it may be advantageous to contact a tissue with an ion pump antagonist to affect ganglionic activity in the adjacent tissue. Examples of channel blockers and ion pump antagonists for use in modulating ANS activity in ganglionic cells, nerve fibers, ganglia, and nerve plexi include:

Na/K, H/K and Vacuolar ATPase Blockers:

Cardiac glycosides may be used to locally modulate the ANS. They inhibit Na(+)/K(+) ATPase, disrupt ion homeostasis, control aberrant ion homeostasis, induce cell block or induce cytotoxicity in neurons. Cardiac glycosides may also regulate gene expression of MDR (Pgp), MRP (MRP1), CFTR or cAMP-activated Cl— channels, and other. 3,4,5, 6-Tetrahydroxyxanthone is another Na/K-ATPase inhibitor that inhibits pump function without activating the kinase signaling function. It inhibits Na/K ATPase pump action with an affinity comparable to ouabain, but does not alter sodium or ATP affinity, is not blocked by potassium, and it does not activate the Src complex or downstream kinases. Other examples of cardiac glycosides that may be used to locally neuromodulate the ANS and related nerves include acetyldigoxin; G-strophanthin; digoxin; digitoxin; ouabain; ouabagenin; lanatoside C; proscillaridin; bufalin; oleandrin; deslanoside; marinobufagenin, and their variants.

SCH-28080 is a potent inhibitor of gastric H+ and K+-ATPase. The antiulcer agents, SCH-28080 and SCH-32651 were examined for their ability to inhibit the H+K+ ATPase enzyme activity in a preparation of microsomal membranes from rabbit fundic mucosa. SCH-28080 inhibited the isolated enzyme activity with a potency similar to omeprazole, IC50s of 2.5 and 4.0 µM respectively. SCH 32651 was less potent exhibiting an IC50 of 200.0 µM. Both compounds may therefore exert their antisecretory activity via a direct inhibition of the parietal cell H+K+ ATPase.

Rabeprazole sodium is a gastric proton pump inhibitor. It suppresses the production of acid in the stomach by inhibiting the gastric H+/K+ ATPase (hydrogen-potassium adenosine triphosphatase) at the secretory surface of the gastric parietal cell. Rabeprazole sodium has been used clinically to treat acid-reflux disorders (GERD), peptic ulcer disease, *H. pylori* eradication, and prevent gastrointestinal bleeds associated with NSAID use.

KM91104 is a cell-permeable vacuolar ATPase (V-ATPase) inhibitor that specifically targets the V-ATPase a3-B2 subunits interaction. Bafilomycin A1 is another specific inhibitor of V-ATPase. Both can be used in small volumes to locally neuromodulate the ANS and treat chronic medical conditions.

Na/K, Na/H and Na/Ca Blockers:

Apamin, a potent Na/K channel blocker, and amiloride and its variants are selective inhibitors of Na/H exchangers and may be used for local chemo neuromodulation of the ANS. The sodium-proton (Na/H) exchange is a predominant pathway for sodium to entry into an energy-deficient neuron, especially under ischemia-induced intracellular acidosis. The inhibition of the Na/H pump by amiloride or its derivative ethyl-isopropyl-amiloride may be used to treat ANS dysfunction.

Cariporide is a selective inhibitor of the Na+/H+ exchanger subtype 1 (NHE-1), also known as the Na+/H+ antiporter. Cariporide has shown to have cardioprotective and antiarrhythmic effects, and has recently been investigated for anticancer activity.

Zoniporide is a potent and selective inhibitor of Na+/H+ exchanger isoform 1 (NHE-1) with an IC50=59 nM at NHE-1, vs. 12,000 nM for NHE-2. It inhibits NHE-1-dependent Na+ uptake with an IC50 of 14 nM and has cardioprotective effects against myocardial injuries and ischemic insults. It inhibits the swelling human platelets and attenuates cardiac contractile dysfunction in rats. Zoniporide may have neurotoxic effects as it causes peripheral sensory axonopathy.

KK4389KR is a Na+/H+ exchanger-1 (NHE-1) inhibitor (IC50=0.23 µM) that may treat ANS dysfunction. It inhibited NHE-1-mediated rabbit platelet swelling, and in anesthetized rats, reduced infarct size from 67% (control) to 43% (at 0.1 mg/kg) and 24% (at 1.0 mg/kg); reduced number of ventricular premature beats from 530 to 266 (at 0.1 mg/kg) and 115 (at 1.0 mg/kg); reduced VF incidence from 17 to 8 (0.1 mg/kg) and 0 (1.0 mg/kg); with demonstrated efficacy for research and treatment of myocardial ischemic diseases in animal model. It may be used to modulate NHE-1 activity on NHE-1 expressing neurons.

CGP-37157 is a specific inhibitor of mitochondrial Na+/Ca2+ exchanger NCLX, as well as sarcoplasmic reticulum calcium-stimulated ATPase and possibly other calcium channels to neuromodulate the ANS. 3',4'-dichlorobenzamil can be used to modulate ANS by inhibiting the Na+/Ca2+ exchanger, Na+ transport and sarcoplasmic reticulum Ca2+ release channels. KB-R7943 (mesylate) is a reverse Na/Ca exchanger inhibitor that may treat ANS disorders.

Na, K, Ca Channel Blockers:

Prilocaine, novocaine, articaine, bupivacaine, and lidocaine block sodium channels and are currently used for local nerve block and for spinal anesthesia. These drugs may be used in conjunction with the above drugs. They may also be mixed with polymers to construct drug formulations where the anesthetic effects last a few weeks to a few years. Methods and formulations are described in the following sections.

Other drugs to locally neuromodulate the ANS and treat medical indications include QX-314 (chloride), a selective sodium channel blocker; glyburide, a potassium channel inhibitor shown to stimulate insulin secretion; and mibefradil hydrochloride, used as a general calcium channel blocker.

Other TRPA, KCNQ and HCN Channel Blockers:

TRPA is a family of transient receptor potential ion channels and TRPA1 is its sole member. It is expressed in the dorsal root ganglia and trigeminal ganglion. A-967079 is a potent inhibitor of TRPA1, which may be delivered locally at or near nerves and ganglia to modulate the ANS.

Humans have over 70 potassium channel genes, but only some are linked to medical conditions. For example, mutations in the KCNQ family of voltage-gated potassium channels (KQT-like, subfamily Q) are associated with cardiac arrhythmias (long QT syndrome 1), deafness and epilepsy. XE 991 is an inhibitor of KCNQ channels, and may be injected locally at or near nerves or ganglia to treat ANS disorders.

Hyperpolarization-activated cyclic nucleotide-gated (HCN) channels are proteins that serve as non-selective ligand-gated cation channels in the plasma membranes of heart and brain cells. HCN channels are also called pacemaker channels because they help generate within the group of neurons and cardiomyocytes. Zatebradine is a HCN channel blocker that is under investigation for bradycardic activity. It may be delivered locally at or near neurons and ganglia to modulate autonomic dysfunction.

Voltage-Gated Channel Blockers:

Lamotrigine is a voltage-gated sodium channel inhibitor. Oxcarbazepine is an inhibitor of voltage gated sodium channels. Phenytoin blocks voltage gated calcium channels and can be used as an anticonvulsant. Tetrodotoxin, saxitoxin, conotoxin, dendrotoxin, iberiotoxin, and heteropodatoxin are naturally occurring or synthetic and block sodium, voltage-gated sodium, or potassium channels. These drugs may be used to locally neuromodulate nerves, ganglia, plexi, or a portion of a nerve to treat chronic medical conditions.

Na/Cl, K/Cl, Na/HCO3 Co-Transport Inhibitors:

The Na—K—Cl cotransporter (NKCC) is a protein that aids in the active transport of sodium (Na), potassium (K), and chloride (Cl) ions across the cell membrane. Two isoforms or this membrane transport protein, NKCC1 and NKCC2, are encoded. Bumetanide is an inhibitor of Na+/K+/Cl— co-transporter that can be used to treat ANS-mediated diseases. CLP257 is a selective K+—Cl— co-transporter and KCC2 (Potassium chloride transporter, a neuron-specific membrane protein expressed in the central nervous system) activator that can be used to restore impaired Cl— transport in neurons with reduced KCC2 activity. Activating the KCC2 transporter is a new mechanism for the treatment of neuropathic pain. Published evidence suggests that CLP257 can modulate plasmalemmal KCC2 protein turnover post-translationally. KCC2 agonists may also be used for local neuromodulation, using methods described herein.

Torsemide is a loop diuretic of the pyridine-sulfonylurea class with anti-aldosteronergic properties and inhibitor of the Na+/K+/2Cl— carrier system. It functions in the thick ascending limb of the loop of Henle and enhances the excretion of sodium, chloride and water from the luminal side of the cells. Furthermore, torsemide may treat oedematous conditions that are associated with diseases such as liver cirrhosis, kidney disorders and chronic congestive heart failure. It may be used to chemically neuromodulate the ANS.

VU0240551 is a potent, selective KCC2 inhibitor. KCC2 is a potassium-chloride exchanger expressed specifically in neurons. KCC2 functions to lower intracellular chloride concentrations below the electrochemical potential of the cells, thereby increasing the hyperexcitability of the neurons. KCC2 activity enhances GABA and other inhibitory neurotransmission and is implicated in pain processing. VU0240551 was discovered in a high-throughput screen, followed by directed medicinal chemistry. VU0240551 is selective for KCC2 over NKCC1 (Na—K—Cl cotransporter). It binds competitively to the K+ site and binds noncompetitively to the Cl— site. It is the only small molecule with specificity for a KCC family member.

Chlorthalidone is a thiazide-like diuretic, an inhibitor of the Na+-Cl— co-transporter. It inhibits Na+ ion transport across the renal tubular epithelium increasing the delivery of Na to the distal renal tubule and indirectly increasing potassium excretion via the Na—K exchange mechanism. Chlorthalidone also promotes Ca++ reabsorption by an unknown mechanism. Several recent comparison studies indicate that chlorthalidone may be a better drug in preventing cardiovascular events than hydrochlorothiazide. It may also be used to modulate GABA-mediated neurotransmission, intracellular chloride concentration, and hypoexcitability or hyperexcitability. Chlorthalidone may also be used to cause neuronal edema and cytolysis by local administration at or near neurons.

S0859 is a selective high-affinity generic inhibitor of the Na+/HCO3-sodium bicarbonate co-transporter (NBC). S0859 does not inhibit Na+—H+ exchange (NHE). It may be a strong mediator of ANS when delivered locally at or near specific neurons and ganglia.

Other Drugs:

Concanamycin A may be used to inhibit acidification of organelles and perforin-mediated cytotoxicity. Sanguinarine is a benzophenanthridine alkaloid isolated from plants belonging to the family Papaveracea. It exhibits anti-bacterial, anti-fungal, anti-inflammatory and anti-cancer properties. It induces cell cycle arrest and sensitizes cancer cells to apoptosis by activating TNF-related apoptosis inducing ligand. It inhibits STAT3, MMP-2, and MMP-9, interacts with glutathione, induces generation of ROS, disrupts the microtubule assembly and causes DNA damage resulting the death of the cancer cells. It may be used to affect nerve cells and modulate the ANS.

Stevioside is a noncaloric natural sweetener, 300 times more potent than sucrose. It inhibits transepithelial transport of p-aminohippurate (PAH) by interfering with the organic anion transport system. At 0.5-1 mM, it showed no interaction with any organic anion transporters (OAT). Stevioside reportedly has genotoxic effects in cultured mammalian cells.

TGN-020 is an inhibitor of Aquaporin 4 (AQP4), the most abundant water channel in brain. Aquaporins (AQPs) are water channels required for maintaining fluid homeostasis and enabling water movement across barrier membranes, but can enhance pathological cellular volume changes and cause edema in injury states. Pretreatment with the AQP4 inhibitor TGN-020 significantly reduced the volume of brain edema associated with ischemic injury in a mouse model of focal cerebral ischemia.

Xipamide is a sulfonamide diuretic that blocks sodium reabsorption in the distal tubules of the kidney, resulting in increased urine output. Xiopamide also blocks the cystic fibrosis transmembrane conductance regulator (CFTR) chloride channel. It may delivered locally at or near neurons, ganglia, and nerve plexi to treat autonomic imbalance.

Drug formulation dose, concentration, and volume used for the local chemo neuromodulation of ganglionic cells, nerves, portions of nerves, plexi or ganglionated plexi by the antagonism of ion channels and ion pumps may vary based on drug half-life, proximity of target ganglia (and other neuronal sites of interest) from the site of administration, pharmacodynamics, and pharmacokinetics. In general, the total dose of the antagonist drug administered to a patient to modulate the ganglia and other target neuronal sites may be, for example, between 0.1 nanograms and 15 milligrams. In other embodiments, the total doses of the ion- and pump-antagonist drugs may be, for example, in the range of 10 nanograms and 30 micrograms.

Different drug formulations and doses may be delivered at or near different target nerves based on their size, morphology, structure, and function. In general, higher drug doses can be delivered locally to generate prolonged ganglionic cell-block or neurotoxicity. Specifically, higher doses may be needed to achieve the desired distribution of the drug to affect cell soma and modulate the stellate ganglion. The total dose of ion-channel or ion-pump antagonist drug delivered to a local tissue for ganglionic cytotoxicity may be, for example, between 0.001 and 15 milligram dose. A smaller volume of drug and a different or diluted concentration may be desirable to modulate individual nerve fibers or axons innervating the ganglionated plexi within fat pads of the heart or the intrinsic cardiac nerves innervating the myocardium.

GPCR Agonists and Antagonists:

G-protein coupled receptors (GPCR) comprise a large superfamily of receptors typically sharing a common structural motif of seven transmembrane helical domains. Some GPCRs instead can be single-spanning transmembrane receptors for cytokines such as erythropoeitin, epidermal growth factor (EGF), insulin, insulin-like growth factors I and II, transforming growth factor (TGF), or multi-polypeptide receptors such as GPIb-V-LX or the collagen receptor that exhibit outside-in-signaling via G proteins. GPCRs play a vital role in the signaling processes that control cellular metabolism, cell growth and filamentation, inflammation, neuronal signaling, and blood coagulation. GPCRs also have a very important role as targets for molecules such as hormones, neurotransmitters and physiologically active substances, and act in a manner that controls, regulates, or adjusts the function of said GPCRs in a particular molecular and cellular context. For instance, GPCRs include receptors for biogenic amines, e.g., dopamine, epinephrine, histamine, glutamate, acetylcholine, and serotonin; for lipid mediators of inflammation such as prostaglandins, platelet activating factor, and leukotrienes; for peptide hormones such as calcitonin, C5a anaphylatoxin, follicle stimulating hormone, gonadotropin releasing hormone, neurokinin, oxytocin, and for proteases such as thrombin, trypsin, and factor VTIa/Xa; and for sensory signal mediators, e.g., retinal photopigments and olfactory stimulatory molecules. In short, GPCRs are a major target for the modulation of ganglionic cell activity and ANS.

Unlike fast ligand-gated receptors, GPCRs are not ion channels. GPCR actions take 100 millisecond to minutes. Fast chemical synapses signal in a fraction of a millisecond. They always evoke complex pleiotropic responses typically involving G proteins, second messengers, and numerous intracellular targets. Fast chemical synaptic receptors only change the membrane potential and sometimes admit calcium ions into the cell. The GPCR coupled monoamines and peptides have longer extracellular lifetimes and thus cannot be targeted for point-to-point wiring to a single postsynaptic cell in a circuit. They work on larger groups of cells.

Common GPCR agonists that signal GPCRs located in ganglia are monoamines like, adrenaline, noradrenaline, serotonin, dopamine, and histamine; small neurotransmitters like acetylcholine (mACh), gamma aminobutyric acid (GABAB), glutamate (metabotropic, mGluR), ATP (P2Y), adenosine, and cannabinoids; peptide neurotransmitters and hormones like opioids, somatostatin, NPY, oxytocin, vasopressin, neurotensins, VIP, galanin, kinins, releasing hormones, and many more; and sensory modalities like light (rhodopsin), odorants, some tastetants including sweet, bitter, and umami.

For most of these GPCR agonists, there are multiple different sensitive GPCRs. In some examples, one agonist can give rise to different intracellular responses depending on the receptor subtypes and splice variants expressed on ganglionic cells. For example, there are nine genes encoding receptors for adrenaline and noradrenaline. Three of them couple to the G-protein $G_q$, often inducing intracellular calcium signaling (al adrenergic receptors), three of them couple to $G_i$, often inhibiting adenylyl cyclase activity, activating GIRK channels, or inhibiting calcium channel activity (α2 adrenergic receptors), and three of them couple to $G_s$, often stimulating adenylyl cyclase activity (β adrenergic receptors).

GPCR agonists are typically released at nerve terminals and varicosities, these fast chemical synapses where presynaptic ACh, glutamate, GABA, or glycine release may activate post-synaptic receptors within nanometers of the release site, triggering the opening of ion channels in one post-synaptic neuron within a fraction of a millisecond. Such agonist action stops in a few milliseconds because agonist is quickly removed from the synaptic cleft. GPCR signaling is fundamentally different because GPCR agonists typically have a half-life of 200 milliseconds to several minutes in tissue.

Importantly, agonist spread over such a time period can act on many cells. Thus, GPCR agonist spread beyond a single synapse (called spillover) can have a distal effect. Agonists can thus be used to affect the mode of operation of neural circuits in a paracrine, hormone-like manner rather than providing specific modulatory effects on a single neural bundle.

In some embodiments, GPCR agonist drugs may be administered locally at or near neurons and ganglia to up-regulate ganglionic cell activity. Agonist drugs that may be administered locally to target the GPCR on nerve tissue and modulate the ANS include: capsaicin; nicotine; glutamate; medroxyprogesterone acetate; genistein; acetylcholine; carbachol; suxamethonium; epibatidine; cytosine; nifene; varenicline; noradrenaline; amantadine; dextromethorphan; mecamylamine; memantine; methylcaconitine; phenylephrine; methoxamine; cirazoline; xylometazoline; midodrine; metaraminol; chloroethylchlonidine; agmatine; dexmedetomidine; medetomidine; romifidine; clonidine; chloroethylclonidine; brimonidine; detomidine; lofexidine; xylazine; tizanidine; guanfacine; amitraz; dobutamine; isoprenaline; noradrenaline; salbutamol; albuterol; bitolterol mesylate; formoterol; isoprenaline; levalbuterol; metaproterenol; salmeterol; terbutaline; ritadrine; L796568; amibegron; solabegron; mirabegron; and others.

In other embodiments, GPCR antagonist drugs may be administered to down-regulate ganglionic cell activity. Antagonist drugs that may be administered at or near neural tissue to target the GPCR include: NPB112; MAb1; MAb23 monoclonal antibody; Nb6B9 nanobody; acepromazine; alfuzosin; doxazosin; phenoxybenzamine; phentolamine; prazosin; tamsulosin; terazosin; trazodone; amitriptyline; clomipramine; doxepin; trimipramine; hydroxyzine; yohimbine; idaxoxan; atipamezole; metoprolol; atenolol; bisprolol; propranolol; timolol; nebivolol; vortioxetine; butoxamine; SR59230A; fasudil; guanfacine; chlonidine; scopolamine; trimethaphan camsylate; guanethidine; galantamine; pentolinium; pancuronium; bupropion; dextromethorphan; diphenidol; ibogaine; hexamethonium; mecamylamine; trimetaphan; conotoxin; bungarotoxin; MDMA; dihydro-beta-erythroidine; and others.

Other examples of drugs that may be administered in a local fashion for the modulation of ganglionic cells via GPCR are listed in Drug Tables 2-4.

TABLE 2

Drugs for local chemoneuromodulation
Annual worldwide sales of drugs acting at GPCRs in the top 100 best selling prescription drugs in 2000.
Compound numbers refer to structures given in Scheme 1.

| Trademark | Generic name | Structure | Company | Disease | Target receptor | million $ |
|---|---|---|---|---|---|---|
| Claritin | loratadine | 1 | Schering-Plough | allergies | $H_1$ antagonist | 3 011 |
| Zyprexa | olanzapine | 2 | Eli Lilly | schizophrenia | mixed $D_2/D_1/5\text{-}HT_2$ | 2 350 |
| Cozaar | losartan | 3 | Merck & Co | hypertension | $AT_1$ antagonist | 1 715 |
| Risperdal | risperidone | 4 | Johnson & Johnson | psychosis | mixed $D_2/5\text{-}HT_{2A}$ | 1 603 |
| Leuplin/Lupron | leuprolide | 5 | Takeda | cancer | LH-RH agonist | 1 394 |
| Neurontin | gabapentin | 6 | Pfizer | neurogenic pain | GABA B agonist | 1 334 |
| Allegra/Telfast | fexofenadine | 7 | Aventis | allergies | $H_1$ antagonist | 1 070 |
| Imigran/Imitex | sumatriptan | 8 | GlaxoSmithKline | migraine | $5\text{-}HT_1$ agonist | 1 068 |
| Serevent | salmeterol | 9 | GlaxoSmithKline | asthma | $\beta_2$ agonist | 942 |
| Plavix | clapidogrel | 10 | Birstol-Myers Squibb | stroke | $P2Y_{12}$ antagonist | 903 |
| Zantac | ranitidine | 11 | GlaxoSmithKline | ulcers | $H_2$ antagonist | 871 |
| Singulair | montelukast | 12 | Merck & Co | asthma | LTD4 antagonist | 860 |
| Pepcidine | famotidine | 13 | Merck & Co | ulcers | $H_2$ antagonist | 850 |
| Cardura | doxazosin | 14 | Pfizer | hypertension | $\alpha_1$ antagonist | 795 |
| Gaster | famotidine | 13 | Yamanouchi | ulcers | $H_2$ antagonist | 763 |
| Zofran | ondansetron | 15 | GlaxoSmithKline | antiemetic | $5\text{-}HT_3$ antagonist | 744 |
| Zoladex | goserelin | 16 | AstraZeneca | cancer | LH-RH antagonist | 734 |
| Diovan | valsartan | 17 | Novartis | hypertension | $AT_1$ antagonist | 727 |
| BuSpar | buspirone | 18 | Bristol-Myers | depression | $5\text{-}HT_1$ antagonist | 709 |
| Zyrtec/Reactine | cetirizine | 19 | Pfizer | allergies | $H_1$ antagonist | 699 |
| Duragesic | fentanyl | 20 | Johnson & Johnson | pain | opioid agonist | 656 |
| Atrovent | ipratropium | 21 | Boehringer Ingelheim | asthma | anticholinergic | 598 |
| Seloken | metoprolol | 22 | AstraZeneca | hypertension | $\beta_2$ antagonist | 577 |

TABLE 3

Drugs for local chemoneuromodulation

| Receptor Target | Antibody | Company | Disease Indication | Status |
|---|---|---|---|---|
| CCR4 | KW-0761/AMG 761/ Mogamulizumab | Kyowa Hakko Kirin | Cancer (adult T-cell leukemia) | Approved in JP (Kyowa) |
| | | | CTCL | Phase 3 |
| | | | Peripheral T and NK-cell lymphoma | Phase 2 |
| | | | PTCL | Phase 2 |
| | | Amgen | Allergy | Phase 1/2 (Amgen) |
| | AT008 | Affitech | Cancer | Preclinical |
| CCR5 | PRO140 | CytoDyn | Human immunodeficiency virus | Phase 2 completed |
| | HGS 1025 | Human Genome Sciences/GSK | Ulcerative colitis | Discontinued (Phase 1b) |
| | HGS 004 | Human Genome Sciences/GSK | HIV | Phase 1 completed |
| | | Human Genome Sciences/GSK | HIV | Preclinical |
| | HGS 101 | Crystal Bioscience | HIV | Discovery |
| | | Pepscan | Undisclosed | Discontinued (Discovery) |
| | (CCR5-2320) Tetravalent bispecific | Roche | HIV | Preclinical |
| CCR2 | MLN1202 | Takeda-Millenium/South-West Oncology Group | Bone metastatsis | Phase 2 completed |
| | | MRCT/Univ Regensberg | RA and MS | Discovery |
| C5aR | NN-8209 | G2 Therapies/Novo Nordisk | RA | Phase 2 completed |
| | NN-8210 (back-up) | | SLE | Phase 1 terminated |
| CGRP-R | AMG-334 | Amgen | Migraine (prophylaxis) | Phase 2 |
| | | | Hot flushes/menopause | Phase 1 |
| CXCR4 | MDX-1338 (BMS936564) | Medarex/Bristol-Myers Squibb | B cell cancers (AML, CML, LBCL, FL) | Phase 1 |
| | ALX-0651 (nanobody) | Ablynx | Stem cell mobilization | Discontinued (Phase 1) |
| | LY_2624587 | Eli Lilly | Cancer | Discontinued (Phase 1) |
| | AT009 | Affitech | Cancer | Preclinical |
| | 515H7 | Pierre Fabre | Cancer/HIV | Preclinical |
| | CX-02 & CX-05 | Northwest Biotherapeutics | Cancer | Preclinical |
| GCG-R | AMG477 | Amgen | Type 2 diabetes | Discontinued (Phase 1) |
| | | Pepscan | Undisclosed | NDRR (Discovery) |
| CXCR5 | SAR113244 | Sanofi | RA/SLE | Phase 1 |
| CCR9 | | Takeda-Millenium | Inflammation (Crohn's Disease) | Discontinued (preclinical) |
| VPAC-1 | | Thrombogenics | Thrombocytopenia | Discontinued (preclinical) |
| FPRL | | Yes Biotech (Anogen) | Alzheimer's disease | NDRR (preclinical) |
| BK2 | DM-204 | DiaMedica | Type 2 diabetes | Preclinical |
| CCR6 | | G2Therapies | Inflammation | Preclinical |
| S1P3 | 7H9 | Expression Drug Designs | Cancer | Preclinical |
| CXCR2 | | Crystal Bioscience | Cancer | Discovery |
| | | MorphoSys | Cancer | Discovery |
| B2AR | | Crystal Bioscience | Respiratory | Discovery |
| PAR1 | | Crystal Bioscience | Cancer | Discovery |
| CXCR3 | AT0010 | Affitech | Inflammation | Discovery |

TABLE 3-continued

Drugs for local chemoneuromodulation

| Receptor Target | Antibody | Company | Disease Indication | Status |
|---|---|---|---|---|
| S1P-R | | Pepscan | Undisclosed | NDRR (Discovery) |
| CCR7 | | Pepscan | Cancer, immunological disorders | Discovery |
| CXCR7 | | Pepscan | Cancer | Discovery |
| GLP-1R | | Abbott/HGS | Type 1 or 2 diabetes Neurological/metabolic | NDRR (early stage) |
| CCR8 | | ICOS/Eli Lilly | Inflammation | Early stage (patent) |
| C3aR | | Human Genome Sciences | Asthma | Early stage (patent) |
| PAR2 | | Boehringer Ingelheim Amgen | Inflammation (IBDS) | Early stage (publication) Early stage (patent) |
| LGR5 | | Kyowa Hakko Kirin | Cancer | Early stage (publication) |
| CRTH2 | | Sosei/Abgenix | Inflammation | NDRR |

TABLE 4

Drugs for local chemoneuromodulation

| Agonist | FFA1 pEC$_{50}$ | GPR120 pEC$_{50}$ | Selectivity and comments | Reference |
|---|---|---|---|---|
| EXAMPLE FFAs | | | | |
| Palmitic acid (C16:0) | 5.2-5.3 | 4.3 | Several actions as nutrients and signaling molecules. Potency observed highly dependent on assay constituents (e.g., BSA) | Briscoe et al. (2003), Itoh et al. (2003), Hirasawa et al. (2005) |
| Oleic acid (C18:1) | 4.4-5.7 | 4.5 | | |
| DHA (C22:6) | 5.4-6.0 | 5.4 | | |
| PPARγ AGONISTS | | | | |
| Rosiglitazone | 5.0-5.6$^a$ | N.D. | GPR40 activity shared by related TZDs such as troglitazone, ciglitazone, and pioglitazone. Low potency GPR120 agonism for rosiglitazone (at 100 μM; Watson et al., unpublished) | Kotarsky et al. (2003), Hara et al. (2009a), Smith et al. (2009) |
| FFAR1 AGONISTS | | | | |
| MEDICA16 | 5.5.-5.9$^a$ | <5.0 | | Kotarsky et al. (2003), Hara et al. (2009b) |
| GW9508 | 6.6-7.3 | 5.5 | GPR40 activity 100-fold selective over a panel of 360 other targets. pEC$_{50}$ values for PPARα, δ, and γ were 4.0, 4.0, and 4.9 respectively | Briscoe et al. (2006), Smith et al. (2009), Sum et al. (2007) |
| Cpd B | 7.1 | N.D. | Lead compound of series inactive at PPARs (<10 μM). GPR40 knockout abolished effects of Cpd B and C on insulin secretion in vivo | Tan et al. (2008), Zhou et al. (2010) |
| Cpd C | 6.8 | | | |
| TUG424 | 7.5$^b$ | N.D. | No activity at FFA2 and FFA3 reported (TUG424). Cpd 37 has 100-fold selectivity for FFA1 over FFA2, FFA3, and PPARs, with improved pharmokinetic properties owing to reduced lipophilicity | Christiansen et al. (2008), Christiansen et al. (2011) |
| Cpd 37 | 7.1$^b$ | N.D. | | |
| TAK-875 | 7.1$^c$ | N.D. | | Sasaki et al. (2011), Tsujihata et al. (2011) |
| GPR120 AGONISTS | | | | |
| Grifolic acid | N.D. | N.D. | Weak GPR120 partial agonist without GPR40 activity (at 100 μM) | Hara et al. (2009b) |
| NCG21 (Cpd 12) | 4.7 | 5.9 | Lacks PPARα, δ, and γ agonist activity (at 100 μM) | Suzuki et al. (2008), Sun et al. (2010) |
| Isoindolin-1-one series (Cpd 2) | N.D. | 6.7 | Banyu patent | Arakawa et al. (2010) |
| Phenyl-isoxazol-3-ol series (Cpd 15) | N.D. | 7.2 | Banyu patent | Hashimoto et al. (2010) |
| Metabolex (Cpd 36) | N.D. | >6.0 | Cpd 36 (100 mg/kg) reduced glucose excursion by 45% after an oral glucose tolerance test in lean C57Bl/6J mice | Ma et al. (2010) |

Agonist pEC$_{50}$ values quoted were obtained from fluorescent indicator measurements of Ca$^{2+}$ mobilization, except $^a$Smith et al. (2009) compared TZD agonism for FFA1 ERK activiation, while Kotarsky et al. (2003) measured FFA1 Ca$^{2+}$ signaling using an aequorin reporter gene; $^b$measurement of insulin secretion/DMR assay; $^c$measurement of inositol phosphate accumulation. N.D.—not determined; pEC$_{50}$ values have not been published.

Doses used for the modulation of ganglionic cells by agonism or antagonism of GPCRs may vary based on drug half-life, proximity of target ganglia from the site of administration (ganglia, plexus, nerve, axon, ganglionated plexus or fat pads), pharmacodynamics, and pharmacokinetics. In general, the total dose of GPCR agonist drugs may be lower than the total dose of GPCR antagonist drug. Additionally, the total dose of drug targeting GPCR in a manner to induce neuronal toxicity may be higher than the total dose of GPCR-targeted drug to stimulate or down-regulate neuronal activity. The total dose of GPCR drug administered to a patient to modulate the autonomic ganglia may be, for example, between approximately 0.1 nanograms and approximately 30 milligrams. In other embodiments, the total dose of GPCR agonist or antagonist drug administered may be, for example, between approximately 10 nanograms and approximately 1 microgram.

In yet other embodiments, higher doses may be delivered locally, to achieve prolonged ganglionic cell block or cell death. In these cases, the total dose of GPCR-targeted drug may, for example, be between approximately 0.01 and approximately 30 mg. In yet other embodiments, lower doses may be delivered locally by mixing the drug with a polymer and releasing the drug over a sustained period of time ranging between a few weeks to few months/years.

In yet other embodiments, different formulations may be delivered to different target sites. For example GPCR antagonist-based formulations may be delivered to the sympathetic ganglia regulating the SNS and GPCR agonist-based formulations may be delivered at or near the vagus PSNS system. In other embodiments, channel blockers may be delivered to the extrinsic sympathetic ganglia and GPCR based formulations may be delivered to the intrinsic cardiac fibers innervating the heart.

Norepinephrine Transporter (NET) Inhibitors:

Norepinephrine transporter (NET) is protein that is responsible for reuptake of the extracellular NE and dopamine, especially in regulating the concentration of neurotransmitters in the synaptic cleft. NET and dopamine transporter (DAT) can transport NE and dopamine at the synapse and inside the neuronal cell. Different NET antagonists can inhibit NE reuptake through various mechanisms, when delivered locally, can modulate the ANS and treat diseases. Drugs may include dihydropyridine calcium antagonists (nifedipine, amlodipine), non-dihydropyridine calcium antagonists (diltiazem, verapamil), uptake-1 inhibitors (alkaloid-cocaine, desipramine, fluoxedine, and opioid analgesics, like tramadol), antidepressants (trazodone, which acts by depletion of neurosecretory vesicle content), sympathomimetics (pseudoephedrine), and mixed type inhibitors (a-b blockers, labetalol and reserpine).

Other Drug Classes:

Chemotherapeutic agents like doxorubicin, anthracyclines, paclitaxel, taxol, and cisplatin may be injected locally at or near nerves and ganglia to neuromodulate and affect nerve function, organ function, and treat various medical conditions. Injection of demyelinating agents (like lipocalin-2) and angiogenesis inhibitors (that specifically targets proliferating endothelial cells, like, vasostatin) may also be used for local neuromodulation.

Drug Combinations

The formulations described may contain one or more drugs and other constituents for specific functions beyond excipients and buffers used in pharmaceuticals to achieve the desired pH level, viscosity, and solubility. These include compounds to improve the visibility of the drug formulation during delivery to the target tissue under different imaging conditions; and anesthetics to reduce local pain associated with nerve block and nerve damage during the procedure. Currently, in pain blockade, a combination of local anesthetic, epinephrine, a steroid, and an opioid is often used to achieve temporary nerve block. Epinephrine constricts blood vessels to slow the diffusion rate of the anesthetic, the steroid is used to reduce inflammation surrounding the overactive ganglionic cells, and the opioids block the pain. These embodiments may be included into a drug formulation as an injectable for local injection or into a polymer. Specific compounds and polymers are described in the following sections.

In addition, two or more drugs may be used in combinatorial form to develop a therapeutically efficacious drug formulation for local neuromodulation using individual drug component dose levels that are safe and significantly below their local dose or concentration levels required for neuromodulation. This mitigates the risk for toxicity associated with potentially higher dose needed for local therapeutic neuromodulation. In one embodiment, patients may be pretreated with precursor agents, either systemically or locally, to prepare the nerve of ganglion for neuromodulation. Pretreatment of the nerve with a precursor drug formulation facilitates the local injection of a lower drug dose (volume or concentration) locally, to achieve prolonged ganglionic cell block or cell death. This allows for the selective use of drugs and concentrations that are below their systemic toxicity levels, yet be efficacious to locally neuromodulate and treat various medical conditions. One example of such combinatorial treatment is to pretreat patients with parasympathomimetic and b-adrenolytic agents that diminish the toxicity of cardiac glycosides. For example, diazepam may be administered as a precursor agent before local neuromodulation of nerves and ganglia using cardiac glycosides and other ion channel blockers.

Drug Formulations

The active pharmaceutical ingredient (API) or bioactive molecule(s) is present in a therapeutically effective amount, i.e., an amount sufficient when administered locally to treat a disease or medical condition mediated thereby. The compositions may also include various other agents to enhance delivery, safety, efficacy, and stability of the active ingredients.

For example, the drug compositions may also include, depending on the formulation desired, pharmaceutically-acceptable, non-toxic carriers such as polyethylene glycol (PEG) or diluents, which are defined as vehicles commonly used to formulate pharmaceutical compositions for animal or human administration. The diluent may be selected so as not to affect the biological activity of the combination. Examples of such diluents include distilled water, buffered water, physiological saline, phosphate-buffered saline (PBS), Ringer's solution, dextrose solution, and Hank's solution. In addition, a pharmaceutical composition or formulation may include other carriers, adjuvants, or non-toxic, nontherapeutic, non-immunogenic stabilizers, excipients, and the like. Compositions may also include additional substances to approximate physiological conditions, such as pH adjusting and buffering agents, toxicity adjusting agents, wetting agents, and detergents. Compositions may also include any of a variety of stabilizing agents, such as an antioxidant.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

Pharmaceutical compositions may be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices may be used.

The data obtained from cell culture and/or animal studies can be used in formulating a range of dosages for humans. The dosage of the active ingredient may lie within a range of circulating concentrations that include the ED50 with little or no toxicity. The dosage may vary within this range depending upon the dosage form employed and the route of administration utilized.

To achieve local drug administration, a parenteral liquid formulation may be generated by reconstituting lyophilized drug with solubilizer. Reconstituted drug and its formulation can be packaged in a vial, ampule, or prefilled syringe. Said liquid may include a solution, emulsion, or suspension. To generate said formulation, an effective amount of neuromodulatory drug may be formulated in the presence of one or more of a solubilizer, stabilizer, buffer, tonicity modifier, bulking agent, viscosity modifier, surfactant, chelating agent, and adjuvant.

In one embodiment, the drug may be formulated with a hydrophobic moiety. A hydrophobic moiety may include a lipid moiety or an amino acid. A hydrophobic moiety may include: phospholipids, steroids, sphingosines, ceramides, octyl-glycine, 2-cyclohexylalanine, benzolylphenylalanine, propionoyl ($C_3$); butanoyl; pentanoyl ($C_5$); caproyl ($C_6$); heptanoyl ($C_7$); capryloyl ($C_8$); nonanoyl ($C_9$); capryl ($C_{10}$); undecanoyl ($C_{11}$); lauroyl ($C_{12}$); tridecanoyl ($C_{13}$); myristoyl; pentadecanoyl ($C_{15}$); palmitoyl ($C_{16}$); phtanoyl (($CH_3$)$_4$); heptadecanoyl ($C_{17}$); stearoyl ($C_{18}$); nonadecanoyl ($C_{19}$); arachidoyl ($C_{20}$); heniecosanoyl ($C_{21}$); behenoyl ($C_{22}$); tracisanoyl ($C_{23}$); lignoceroyl (C2); alcohols; glycerol; polyethylene glycol; dimethylsulfoxide; mineral oil, and cholesterol; wherein said hydrophobic moiety is formulated in the presence of drug.

In another embodiment, the drug may be formulated with a salt. In yet another embodiment, the drug may be formulated in the presence of an ion. For example, anions of chloride; fluoride; or bromide may be used. Additionally, cations of calcium; potassium; sodium; or zinc may be used.

In yet another embodiment, the drug composition may include a nontherapeutic compound (contrast agent) to assist with the visualization of the drug injection to the target nerve tissue under different body imaging conditions. Contrast agents that may be mixed into the drug formulation for visibility under x-ray, electron-beam CT, external and intravascular ultrasound, and MRI are described in subsequent sections.

The components used to formulate the pharmaceutical compositions may be of high purity and may be substantially free of potentially harmful contaminants (e.g., at least National Food (NF) grade, generally at least analytical grade, and more typically at least pharmaceutical grade). Moreover, compositions intended for in vivo use may be sterile. To the extent that a given compound must be synthesized prior to use, the resulting product may be substantially free of any potentially toxic agents, such as any endotoxins, which may be present during the synthesis or purification process. Compositions for parental administration may also be sterile, substantially isotonic, and made under GMP conditions.

Sustained-Release Formulations

The above drug formulations may also be incorporated into a polymer matrix to release the drug over a period of time, ranging between a few weeks to a few months/years, and affect the nerves and ANS function. The polymers may be biostable or biodegradable and constitute good matrices for controlled drug delivery. Using different delivery methods and devices, generally described in U.S. Pat. Nos. 6,923,986, 6,703,047, 6,639,014, 6,632,457 and 6,514,534, different composite hydrogel-based drug formulations, gels, plugs, and microspheres containing the therapeutic drug molecules described in the present invention may be administered at or near the specific nerve target sites, sympathetic chain ganglia, and nerve fibers to treat disease by local chemical neuromodulation.

The bioactive agent or therapeutic drug molecule is trapped in a polymeric network of hydrophobic regions which prevent the loss of the drug. In some cases, the composite material has two phases, where both phases are absorbable, but are not miscible. The continuous phase may be a hydrophilic network (such as a hydrogel, which may or may not be crosslinked) and the dispersed phase be hydrophobic (such as an oil, fat, fatty acid, wax or fluorocarbon, or other synthetic or water immiscible phase). In some cases, especially water soluble drugs, a release rate modifying agent may also be used to incorporate the drug and control its release profile. Examples of macromers, polymers, cross-linkable groups, hydrophilic components and hydrophobic components and rate-releasing modifying agents are described below.

In one embodiment, biodegradable macromers are provided in an acceptable carrier and crosslinking, covalently or non-covalently, to form hydrogels which are thermoresponsive. The drug formulations described above (biologically active drugs) may be incorporated in the macromer solution or in the resulting hydrogel after crosslinking. The hydrogel formulations are optimized for volume and drug release rate, which are temperature dependent. The hydrogels may be formed in situ, for example, at a tissue site, and may be used for controlled release of drugs at or near nerve tissue. The macromers used to form the hydrogels may also be optimized for selective properties including hydrophobicity, hydrophilicity, thermosensitivity or biodegradability, and combinations thereof. The gels permit controlled drug delivery and release the drug or biologically active agent in a predictable and controlled manner locally at the targeted nerve site.

The macromers may include cross-linkable groups which form covalent bonds with other compounds, while in aqueous solution. This allows crosslinking of the macromers to form a gel, either after, or independently from thermally dependent gellation of the macromer. Chemically or ionically crosslinkable groups known in the art may be provided in the macromers. Polymerization chemistries may include, for example, reaction of amines or alcohols with isocyanate or isothiocyanate, or of amines or thiols with aldehydes, epoxides, oxiranes, or cyclic imines; where either the amine or thiol, or the other reactant, or both, may be covalently attached to a macromer. Mixtures of covalent polymerization system, sulfonic acid, or carboxylic acid groups may be used.

The macromers may include hydrophobic domains and the hydrophobicity of the gel may be tailored to achieve a desired drug-release profile. The cell membrane is composed of a lipid bilayer with the inner region being hydrophobic. A hydrophobic tail may be incorporated into the macromer so that the biologically active drug molecule can diffuse into the lipid bilayer. Examples of tail groups include fatty acids, diacylglycerols; molecules from membranes such as phosphatidylserine, and polycyclic hydrocarbons and derivatives, such as cholesterol, cholic acid, steroids and the like. In addition, more than one hydrophobic group may be incorporated into the macromer to improve adherence of the hydrogel to the target tissue, the neuron. Examples of hydrophobic groups include oligomers of hydroxy acids such as lactic acid or glycolic acid, or oligomers of caprolactone, amino acids, anhydrides, orthoesters, phosphazenes, phosphates, polyhydroxy acids or copolymers of these subunits. Also, the hydrophobic regions may be formed of poly(propylene oxide), poly (butylene oxide), or a hydrophobic non-block mixed poly (alkylene oxide) or copolymers thereof. Poly L-lactide, or poly D,L-lactide or polyester, which is a copolymer of poly(lactic-co glycolic) acid (PLGA), may also be used.

The biodegradable macromers may also include hydrophilic regions by incorporating water-soluble hydrophilic oligomers available in the art. They may include polymer blocks of poly(ethylene glycol), poly(ethylene oxide), poly (vinyl alcohol), poly(vinylpyrrolidone), poly(ethyloxazoline), or polysaccharides or carbohydrates such as hyaluronic acid, dextran, heparan sulfate, chondroitin sulfate, heparin, or alginate, or proteins such as gelatin, collagen, albumin, ovalbumin, or polyamino acids.

The biodegradable polymers incorporated into the formulation may be hydrolyzable under in vivo conditions. Hydrolyzable groups include polymers and oligomers of glycolide, lactide, epsilon-caprolactone, and other hydroxy acids. Poly (alpha-hydroxy acids) include poly(glycolic acid), poly(DL-lactic acid) and poly(L-lactic acid). Other materials include poly (amino acids), polycarbonates, poly(anhydrides), poly (orthoesters), poly(phosphazines), and poly(phosphoesters). Polylactones such as poly(epsilon-caprolactone), poly(delta caprolactone), poly(delta-valerolactone) and poly(gamma butyrolactone). Monomeric, dimeric, trimeric, oligomeric, and polymeric regions may be used to yield a target polymer-drug formulation that is substantially water soluble.

Release rate modifying agents may also be incorporated into drug-polymer formulations to control drug release. Hydrophobic agents are able to form a relatively stable dispersed phase within a continuous hydrogel matrix and may be used as a secondary container for substantially water soluble therapeutic drugs. A list of rate-release modifying agents may be found in Table I of U.S. Pat. No. 6,633,457. Degradation times and drug release profiles may be tailored by selecting appropriate polymers or monomers using linkages susceptible to biodegradation, such as ester, peptide, anhydride, and orthoester, phosphazine, and phosphoester bonds. Crystallinity and molecular weight may also significantly alter degradation rates.

The hydrogel matrix may also include a biologically active agent, either singly or in combination with different agents. Examples of therapeutic or bioactive agents are described in previous sections.

Drug and/or drug-polymer formulations may also incorporate contrast agents to visualize the target site for delivery during the clinical procedure. Ionic contrast agents for visibility under x-ray fluoroscopy and CT include diatrizoate (Hypapaque) and metrizoate (Isopaque 370) monomers and ioxaglate (Hexbrix) dimer; non-ionic kind include iopamidol (Isovue 370), iohexol (Omnipaque 350), iopromide (Oxilan 350), iopromide (Ultravist 370), iodixanol (Visipaque 320) monomers, and ioversol dimer. Contrast agents for visibility under ultrasound include microbubbles of suphur hexafluoride (Sonovue, Bracco) and albumin shell with octofluoropropane gas (Optison, GE heathcare) or lipid microspheres (Perflexane, Alliance Pharmaceutical; Perflutren). Barium sulphate may also be mixed into the formulation to improve the visibility of the drug formulation during injection to the target nerve site. For treatment procedures under MRI, contrast agents based on gadolinium like gadoterate (Dotarem), gadodiamide (Omniscan), gadobenate (MultiHance), gadopentetate (Magnevist), gadoteridol (ProHance), gadoversetamide (OptiMARK), gadobutrol (Gadavist), and gadopentetic acid dimeglumine (Magnetol) may be incorporated into the polymer and/or drug formulation. Many other gadolinium, iron-oxide, iron-platinum, manganese, and protein-based contrast agents may also be incorporated into the drug or drug-polymer formulations to improve the visibility of drug injection under MRI.

Drug and/or polymer formulations may also incorporate anesthetic agents to reduce pain during the clinical procedure. Examples of ester-based anesthetic agents that may be incorporated into the formulation include procaine, amethocaine, cocaine, benzocaine, and tetracaine. Examples of amide-based are lidocaine, prilocaine, bupivicaine, levobupivacaine, ropivacaine, mepivacaine, dibucaine, and etidocaine. They may be included in the injectable (non-polymer) or polymer-based drug formulations.

Polymer-based drug formulations may be prepared outside the body in solid or gel form and delivered using different delivery systems to the target nerve locations. Ingredients or precursors of the formulations may be pre-packaged and sterilized, in dry or liquid forms, at a manufacturing facility. The dry or aqueous precursors may be premixed by medical personnel in the clinical setting and injected at the target nerve site. Water in the aqueous environment surrounding the target nerve or ganglion initiates transformation and the formation of the drug-releasing hydrogel implant. Alternatively, the finished product may be mixed, sterilized, and packaged at a manufacturing facility or mixed by medical personnel.

Dry powder formulations may include a mixture of two or more individual dehydrated precursors and the drug formulation. The precursors activate upon exposure to water in bodily tissue, dissolve and simultaneously cross link to form the hydrogel implant containing the drug formulation. In one embodiment, the precursors may comprise a lyophilized, or freeze-dried forms that are compounded together with the drug. As an example, a two-part dehydrated hydrogel precursor mixture may include an electrophilic, multifunctional poly(ethylene glycol) ("PEG") precursor and a multifunctional, nucleophilic PEG precursor. These two components may be compounded together with the drug, when dry. Upon exposure to an aqueous environment, rapid chemical cross-linking occurs and forms a drug-releasing hydrogel implant. Another embodiment may include a fully-synthetic, solid PEG particulate hydrogel composition. A degradable PEG hydrogel is fabricated, then dried or lyophilized, pulverized, and mixed with the drug (biologically active ingredient) powder to form the hydrogel implant at or near the target nerve site using specific delivery systems.

Polymer-based drug formulations may also be prepared or cross-linked inside the body to form the drug formulation described in this invention using different delivery systems. Two or more ingredient formulations may be prepared, packaged, and sterilized at a manufacturing facility (separate packages or a combined package with multiple chambers). They may be mixed using mixers, injecting guns, and delivery systems so that the polymers cross-link at the target nerves site location and release the drug over time.

In another embodiment, a hydrogel-based drug formulation product may be fabricated in the anhydrous form and delivered to the target site in solid form. In situ swelling after the plug comes into contact with water in the tissue initiates drug release to the target tissue.

Clinical Procedure and Devices

Agents described in the above sections may be injected locally, at or near the target nerve sites in the body with a device, using different imaging techniques such as x-ray (fluoroscopy or angiography), electron beam computed tomography (EBCT or CT), magnetic resonance imaging (MRI), optical coherence tomography (OCT), external ultrasound or intravascular ultrasound (IVUS) techniques. Imaging may be used to navigate a device to the target nerve site, visualize the nerves and tissue structure surrounding the nerve, make necessary measurements about the nerve anatomy, orient the device, inject the drug locally, and deliver treatment. Imaging of organs and nerve stimulation may also be done to confirm the nerve target nerves innervating organs and measure the nerve activity before, during, and after treatment.

External Needle-Based Devices:

The device may include a syringe with a long 20-33 gauge needle to reach the nerve site under X-ray, CT, MM, or ultrasound imaging. Various approaches may be used to puncture the skin and advance the needle to reach the stellate ganglion, other sympathetic chain ganglia and nerves.

One method may use a direct, anterior paratracheal approach to reach the target ganglion or nerve. A 5 cm long, 22 G needle may be inserted perpendicular to the skin (near the neck) until bone contact is made. The needle may be slightly withdrawn to rest anteriorly to the precervical fascia to access the stellate ganglion. After a negative aspiration test to verify that the location of the needle is (outside blood vessels adjacent to the sympathetic ganglia, indicated by the lack of blood draw during aspiration, and) at or near the target ganglion, approximately 0.01 to 20 mL of the drug formulation may be injected. Other sympathetic chain ganglia, interconnecting nerve fibers, and rami communicantes may be similarly accessed and treated. The needle may be removed and the access site closed.

A second method may use an anterior paratracheal approach to reach the target ganglion or nerve under external ultrasound guidance. The patient is placed in the supine posture and the neck region may be visualized under real-time ultrasound imaging using a 3-12 MHz linear array probe (HD11-XE® Philips, Wash., USA). A 5 cm long, 22 G needle may be inserted in the neck and then advanced to reach the stellate ganglion, so that the needle tip lays anterior to the longus coli muscle (anterior to C6 transverse process). After a negative aspiration test to verify that the needle is at the target nerve location, approximately 0.01 to 20 mL of the drug formulation may be injected. Other sympathetic chain ganglia, interconnecting nerve fibers, and rami communicantes may be similarly accessed and treated.

A third method may use an anterior paratracheal approach to reach the target ganglion or nerve under external x-ray fluoroscopy guidance. The patient is positioned supine on a fluoroscopy table, placed into cervical extension with a shoulder roll and hemodynamically monitored (e.g., pulse oximetry, electrocardiogram). The patient is sedated or placed under local anesthesia. The right C6 vertebral body is identified, local anesthetic administered, and a 22-gauge needle may be advanced percutaneously to the anterolateral C6 vertebral body. The needle location may be confirmed by x-ray and by negative aspiration to verify that no blood and cerebrospinal fluid is retrieved. A small amount of contrast media may be injected through the needle to further confirm needle location and assess the spread over the pre-vertebral plane. Digital subtraction angiography may be used to verify the absence of vascular uptake. A small amount of local anesthetic may be injected to further verify target site location. Then, approximately 0.01 to 20 mL of the drug formulation, described below, may be injected gradually. The needle may be removed and the procedure is complete. Other nerve target sites may be similarly accessed, including the cervical ganglia and thoracic ganglia of the sympathetic chain, ganglia, plexi, nerves, and portions of a nerve.

Other imaging methods like CT and MM imaging methods may similarly be used to treat the sympathetic chain ganglia and nerves. Currently most needles are made of metals and alloys like stainless steel and cobalt-chromium alloys. Metallic needles cause large imaging artifacts under CT and MM imaging which makes it difficult to image and identify surrounding tissue during the clinical procedure. Mill and CT compatible needles may be made from niobium, tantalum, platinum, zirconium, and palladium-based alloys, which have low magnetic susceptibility, and produce less artifacts and improve needle visibility during imaging. Other examples of non-metallic materials include ceramics, carbon fibers, polymers and their composites, etc. Metallic needle tip designs may also be coated with bismuth and other low magnetic susceptibility materials to clearly identify the target nerve tissue.

In one embodiment of the microneedle, one or more nanoelectrode sensors may be incorporated at the tip of the microneedle, on the surface, to measure the electrical signals transmitted from the target nerve, ganglion, or portion of the nerve. Sympathetic nerve activity may be measured directly using a wired connection to a datalogger or remotely using a wireless connection. For example, planar nanoelectrode arrays (PNAs) have been used to measure SNA near the stellate ganglion using a wireless transmitter.

In another embodiment, the microneedle itself may be used to measure the SNA activity of the nerve, ganglion, or portion of the nerve. Typically, the microneedles are made of metals like stainless steel, high-carbon steel. Further, they may be coated with high conductivity elements like gold, tungsten, tantalum and chromium to improve signal measurements. Typically, the peak nerve signals measurements from an exposed stellate ganglion in dogs varied between 100-1500 microvolts. Such measurements may be used to study the efficacy of treatment by monitoring the signal, before, during, and after treatment, i.e., local administration of a drug formulation to modulate and/or interrupt nerve signaling.

Endoscope-Based Devices:

Another embodiment of a device may include an endoscope with capabilities to visualize the target nerve and administer the drug formulation locally at the nerve target site, similar to a transthoracic endoscopic sympathectomy procedure. To treat the stellate ganglion, for example, the patient may be placed under general anesthesia and about a 6 mm incision may be made near the tip of the shoulder blade. Through this incision, a small endoscope, 5 mm in diameter, may be introduced into the chest between the ribs. The lung may be retracted out of the way, and the sympathetic ganglia and nerves may be visualized with the endoscope. Through a second incision, a smaller device or instrument may be introduced and advanced to the stellate ganglion under endoscopic guidance. The drug formulation may be gradually administered to the stellate ganglion. Both instruments may be removed and the treatment is complete.

Another endoscopic method to access the stellate ganglion, other sympathetic chain ganglia, and interconnecting nerves may use a supraclavicular approach. A small incision may be made above the left clavicle, and the platysma and the clavicular head of the sternocleidomastoid muscle may be transected, avoiding injury to the thoracic duct. The scalene fat pad may be retracted laterally and the anterior scalene muscle (anterior to the carotid artery) and the phrenic nerve (anterior to the scalene muscle) may be identified. The phrenic nerve may be gently mobilized and the scalene muscle may be transected and retracted upward to sufficiently expose the thoracic ganglia. Then, the seventh cervical transverse process (behind the subclavian artery) may be exposed along with the pleural dome, and the apical pleura may be freed from its ligament (Sibson's fascia). The lung may be deflected caudally to expose the stellate ganglion and the second thoracic ganglion. A small volume of the drug formulation, described above, may be injected locally at or near the stellate ganglion, other sympathetic chain ganglia, or interconnecting nerve fibers between the ganglia. Nerve activity at the stellate and sympathetic chain ganglia may be monitored before and after local drug injection to verify the reduction in SNA and verify the acute efficacy of treatment using an electrophysiology catheter or a high-frequency stimulation catheter. Once the treatment efficacy is verified, the lung may be repositioned, the muscles may be sutured, and the incision may be closed. No pleural drainage is needed because this approach does not require pleural incision. Although the anatomical field of view is limiting with the supraclavicular approach, the complications associated with pulmonary (pneumothorax), trauma, and aesthetics are reduced.

Yet another endoscopic method to access the sympathetic chain ganglia and interconnecting nerves between them may use a transaxillary approach. The upper arm may be abducted to about 100 degrees and the pectoralis major and intercostal muscles may be divided. The pleura may be opened carefully avoiding the long thoracic nerve, the intercostal vessels, the azygos vein, and the thoracic duct. The lung may be depressed to expose the posterior thoracic wall, the first rib may be identified, and the pleura may be incised over the sympathetic trunk and the appropriate ganglia or nerve fibers may be exposed. A small volume of the drug formulation, described above, may be injected locally inside or adjacent to the stellate ganglion, other sympathetic ganglia, or the interconnecting nerve fibers between them. Nerve activity inside the stellate and other ganglia may be monitored before and after local drug injection to verify the reduction in SNA and verify the acute efficacy of treatment. Once the treatment efficacy is verified, the lung may be repositioned, the different muscles may be sutured, and the incision may be closed. This approach is a good alternative to open surgery especially in select patients and infants.

Other video assisted thoracic endoscopy procedures may be done through the chest (anterior and posterior) to reach the stellate ganglion and the sympathetic chain ganglia. Other nerve target sites may be similarly accessed, including the cervical and thoracic ganglia of the sympathetic chain, ganglia, plexi, nerves, and portions of a nerve using endoscopy techniques. For example, two incisions on the fourth and fifth intercostal spaces may be used to reach and treat the second and third sympathetic ganglia and the interconnecting nerves between them.

The endoscopic procedures are less risky compared to open thoracotomy with reduced complication rates, and may need less pleural drainage time and shorter hospital stays. The magnified surgical field of view and minimally invasive access (small scars in the axilla and the left chest) are the major advantages. However, there are limitations to the endoscopic approach. They include accidental hemorrhages, dedicated instrumentation and training, and incidence of pneumothorax (0.2-10%) and prolonged intercostal neuralgia (1-2%).

Catheter-Based Devices:

Another embodiment of the device may include an endovascular catheter, with multiple lumens, ports, and elements, to assist navigation through the vascular bed of the human body to the nerve target site and locally administer the drug. The catheter may be advanced from the venous or arterial blood circulation system. Typical endovascular access or puncture sites for treatment include the femoral artery, femoral vein, brachial artery, brachial vein, radial artery, radial vein, carotid artery, carotid vein, subclavian artery, and subclavian vein. Catheters may be advanced from one of these puncture sites to reach one of the blood vessels adjacent to the target nerve location under X-ray fluoroscopy, CT, ultrasound, OCT, or MM guidance. The catheter may then be positioned in the vessel wall using an anchoring element and confirmed using imaging. The injection element may then be activated and its location relative to the target nerve issue is verified under different imaging conditions. After confirming the location, the drug formulation may be injected at or near the target nerve site. After treatment, the injection element may be deactivated, the anchoring element released, and the catheter removed from the body.

In one embodiment of the device, an anchoring element to stabilize the position of the catheter may include a compliant balloon made from a homogenous material. In other embodiments, the balloon may be made from different materials so that portions of the balloon are compliant to ensure that the injection element is oriented towards the target nerve location. In another embodiment, the balloon may incorporate an electrical sensor (that accommodates balloon expansion) to locate the stellate or other sympathetic ganglion based on their local nerve-signaling activity. In yet another embodiment, the anchoring element may include a spring or self-expanding mesh or stent-like structure. The anchoring element may be constrained with a sheath of the catheter. Once the catheter is advanced to the target nerve site, the sheath may be retracted so that the anchoring element is released to expand and conform to the vessel wall. The self-expanding anchoring element may be pre-shaped and constrained in such a way as to orient the injection element towards the nerve target site upon release.

In one embodiment of the device, the injection element may include a microneedle (or an equivalent drug delivery element). The injection element may be activated by the anchoring element (balloon expansion or unconstraining the self-expanding mesh) or activating it separately using a handle to advance the microneedle across the vessel wall to reach the target nerve location. The microneedle may have sufficient strength and caliber (for example, between approximately 10-200 microns in diameter) to penetrate the vessel wall, yet small in diameter to minimize vessel trauma, vessel perforation, and bleeding complications.

In another embodiment, the injection component may include a needle-less component with a micro-aperture. The injection element may administer a small volume (for example, approximately 10-500 microliters) of drug formulation to the target nerve tissue through a small aperture from a reservoir by piercing the tissue under transient conditions (<1 second) of high pressure (between 100-10,000 psi). The method may comprise positioning a delivery device including the aperture within the artery and injecting the drug formulation at high velocity out of the aperture, across the artery wall. The drug acts on the local nerve tissue to disrupt nerve signal transmission and treat disease. The micro-aperture may be of sufficient caliber (for example, between approximately 10-200 microns in diameter) to avoid injury to the vessel wall (perforation, bleeding) and surrounding tissue. The needle-less component may be in communication with the drug reservoir and the high-pressure injection system on one end (outside the body) and the micro-aperture in contact with the vessel wall (inside the body). The needle-less component may include a balloon, a long injection tube, or a series of injection tubes, with a micro-aperture in fluid communication with the drug reservoir.

The metallic injection elements (microneedles and hollow tubes) may be used as microelectrodes to monitor nerve signal activity before, during, and after treatment. In one embodiment, one or more nanoelectrode sensors may be incorporated on surfaces of the microneedle tips or injection tubes to measure the electrical signals transmitted from the target nerve or ganglion. The Injection elements may be coated with gold, silver, carbon, tungsten, or other conductive coatings to monitor local ganglionic and nerve activity during the procedure. Both wired and wireless sensors may be used to monitor local nerve activity.

In another embodiment, the metallic injection elements (microneedles and hollow tubes) may be used to stimulate the cardiac nerves and measure the extent of sympathetic nerve overactivity (stellate ganglion and other ganglia of the ECNS) or identify the regions of conduction inhomogeneity (in the myocardium). The microelectrodes may be connected to a generator to stimulate the nerves and monitor nerve signal activity before, during, and after treatment. In one embodiment, one or more nanoelectrode sensors may be incorporated into the anchoring element to amplify the local nerve signal and assist measurement. Injection and anchoring elements incorporate additional sensors for activating and receiving local nerve signals.

Delivery Systems for Injecting Polymer and Gel-Based Formulations:

The composition mixtures of the dehydrated hydrogel precursors and the drug molecules may be delivered using several delivery systems that are known in the medical and pharmaceutical art. They may be delivered using pre-filled syringes or gas powered atomizers. Other delivery methods include aerosolizing apparatus (Inhale Therapeutics, Aradigm Corp.) and pneumatic, needle-less injectors (Powderject Ltd., U.K.; Bioject, Portland, Oreg.). Pneumatic injectors may be actuated by compressed gases (argon, carbon dioxide, nitrogen, or helium), or springs. The injectors may be partially or fully disposable and often come packaged with a fill needle or vial adaptor to draw the medication or an implant-forming material or solution from a vial into a syringe.

Figure 2A:
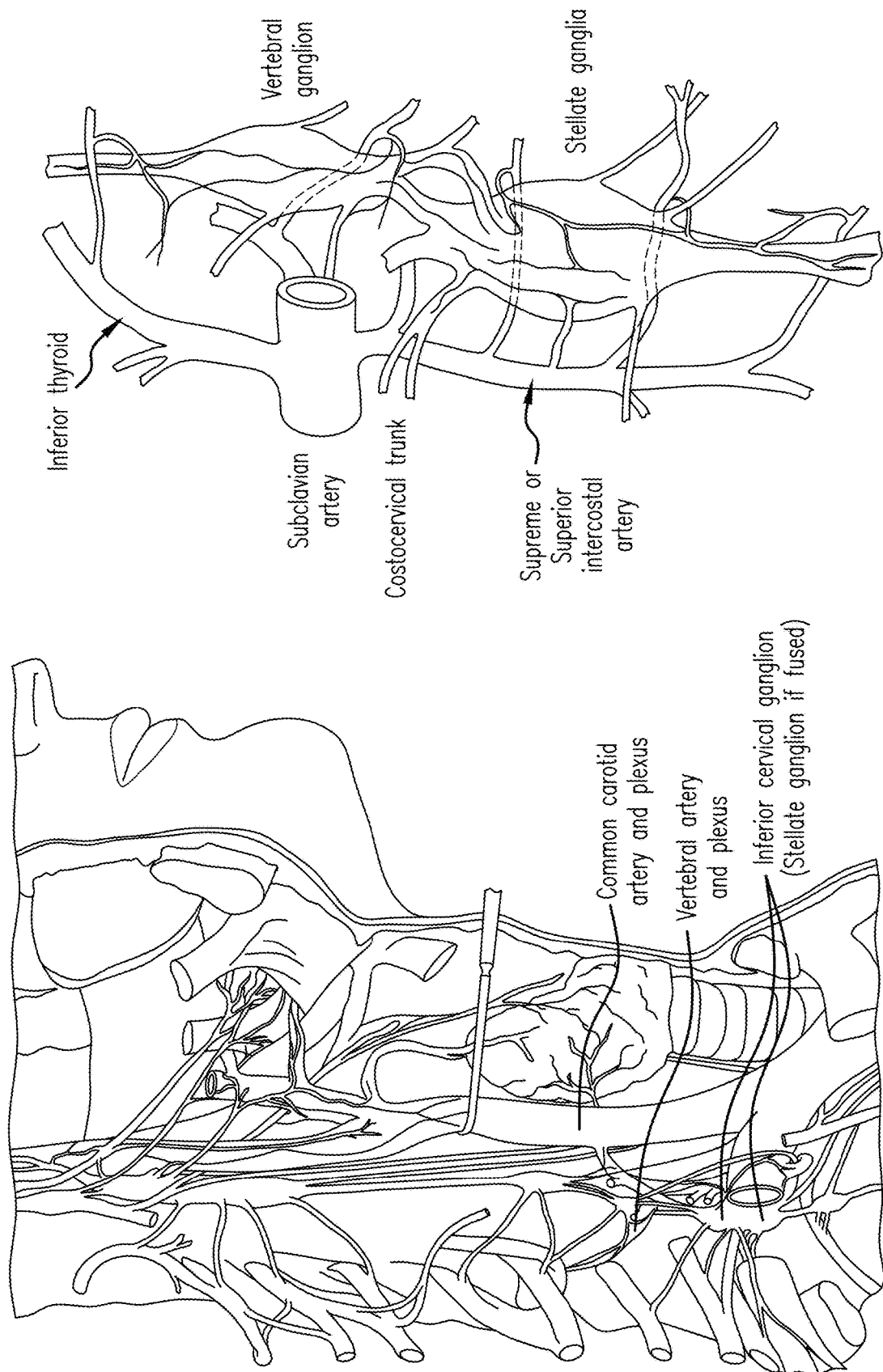
FIG. 2A shows the anatomy of the stellate ganglion, ganglia of the sympathetic chain, and nearby tissue and vascular structures in the neck.
Figure 2B:
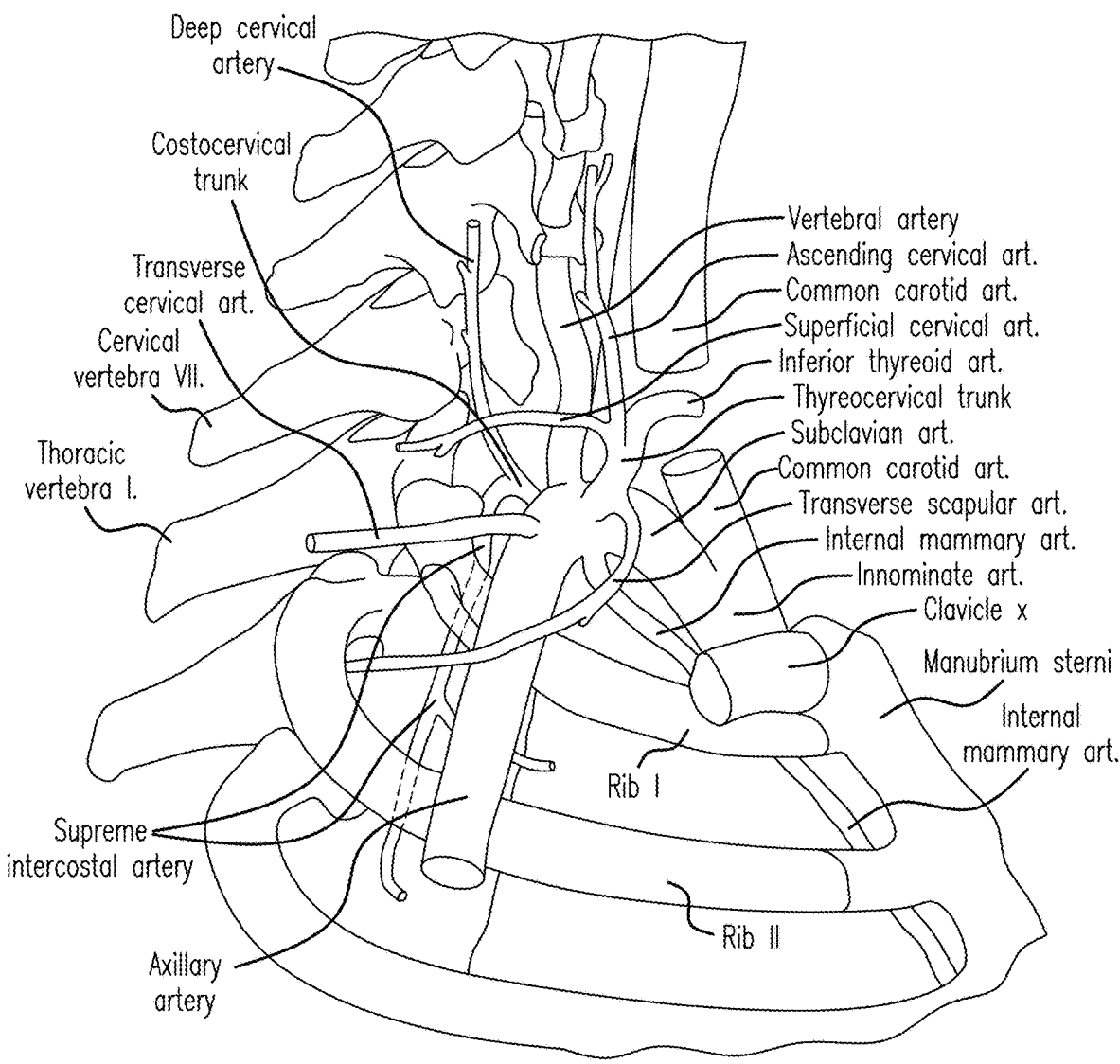
FIG. 2B shows the skeletal structure and blood vessels surrounding the stellate ganglion, which may be used for surgical and for vascular access.
Figure 2C:
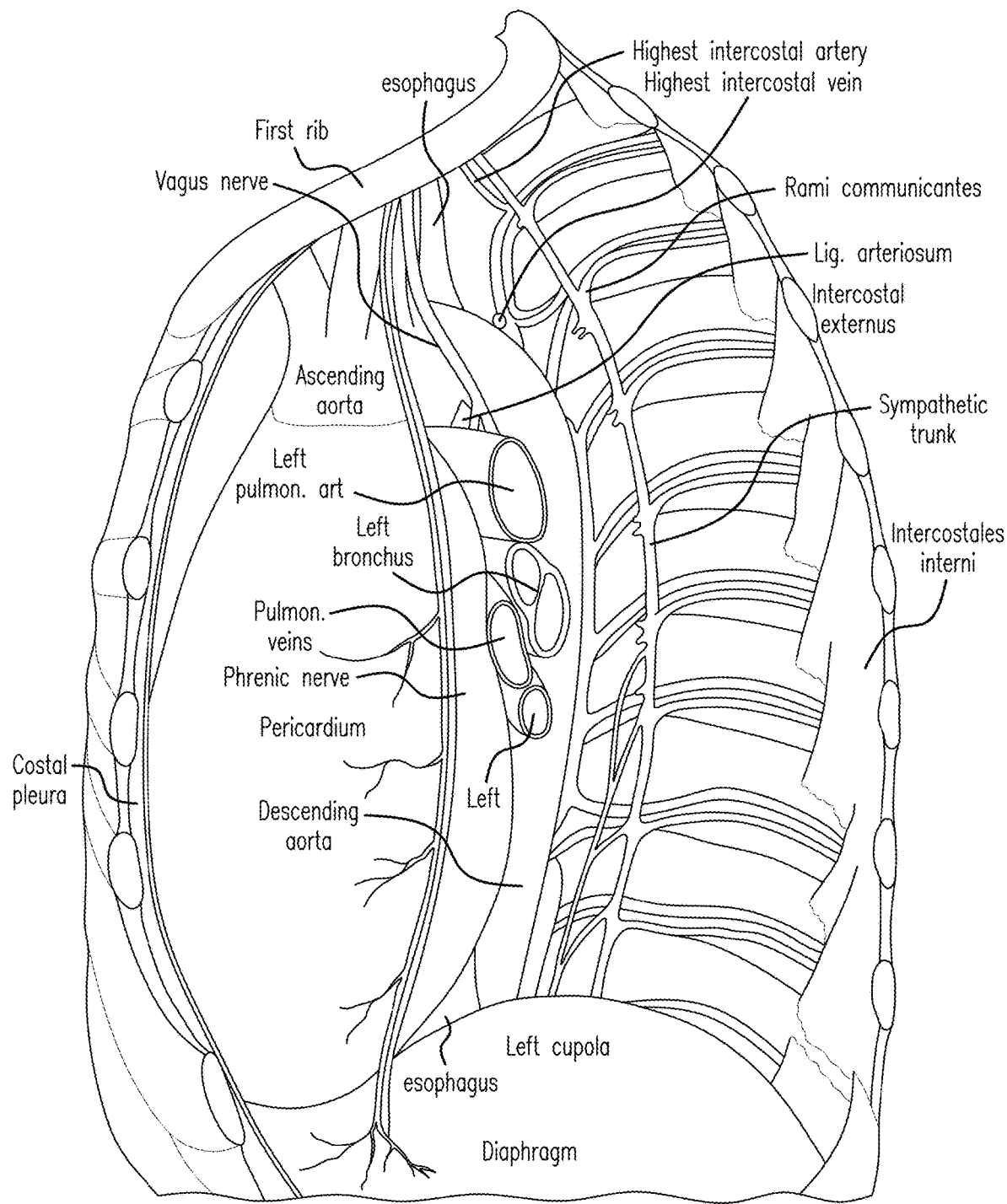
FIG. 2C shows the intercostal arteries and intercostal veins adjacent to the thoracic sympathetic chain and ganglia (sympathetic trunk) in relation to the ribs and heart inside the thoracic cavity.

Methods of Access—ECNS:

Using a catheter, there are several endovascular navigation methods and endovascular locations for accessing different nerve target sites of the ANS to treat various disease conditions, described above. In one embodiment, the stellate ganglion may be accessed by introducing the catheter through the femoral artery using standard endovascular methods under fluoroscopy. Typically, the methods involve using flexible guidewires, guiding catheters, sheaths, and other ancillary devices to reach the vessel location. The catheter may then be advanced from the femoral artery through the aorta and the subclavian artery and may be positioned in any of the vessels adjacent to the stellate ganglion. The catheter may be positioned in the vessel or at the junction (intersection or bifurcation) between two vessels. As shown in FIGS. 2A-2C, the vessel locations include the subclavian artery, the axillary artery, the costocervical trunk, the deep cervical artery, the supreme or superior intercostal artery, the transverse cervical artery, the vertebral artery, the superficial cervical artery, the common carotid artery, the subclavian-vertebral artery ostium or bifurcation, etc. An angiogram may be performed to confirm the position of the catheter. A microneedle may be activated to advance it across the vessel wall to reach the stellate ganglion. The position of the microneedle may be confirmed through a test injection of contrast, and the drug formulation may be gradually injected through the injection port of the catheter. The microneedle may be retracted and the catheter may be removed to complete the treatment procedure.

In another embodiment, the catheter may be introduced through the femoral vein and advanced through the inferior venacava to reach the venous circulation system adjacent to the stellate ganglion. These veins include and are not limited to the subclavian vein, the axillary vein, the costocervical vein, the deep cervical vein, the supreme or superior intercostal vein, the transverse cervical vein, the vertebral vein, the superficial cervical vein, the internal jugular vein, the external jugular vein, the innominate vein etc., and the junction (bifurcation or intersection) etc. Catheters may be positioned in the veins on the left vascular bed to access the left stellate ganglion and in the veins on the right vascular bed to access the right stellate ganglion. The radial vein or brachial vein may be used to introduce the catheter in place of the femoral vein.

In another embodiment, the catheter may be introduced through the radial artery or brachial artery to reach the subclavian artery and the nearby vasculature surrounding the cervical and thoracic ganglia, related sympathetic nerves, and nerve fibers shown in FIGS. 2A-2C. The radial or brachial veins may be punctured to introduce and advance the catheter to reach the venous vasculature adjacent to target ganglia, sympathetic nerves, and nerve fibers.

In another embodiment, the catheter may be introduced through the various intercostal arteries or veins that run parallel to the ribs of the thoracic cavity to reach the cervical and thoracic ganglia, related sympathetic nerves, and nerve fibers, as shown in FIGS. 2A-2C. A small incision may be made in the thoracic cavity to access the intercostal artery or vein to introduce and advance the catheter to reach the target ganglia, sympathetic nerves, and nerve fibers.

Endovascular devices and methods of vascular access for the treatment of the stellate ganglion and other ganglia of the sympathetic chain described provide safety advantages over nerve block treatments using needle injections or video-assisted thoracic surgical procedures. Surgical trauma to the brachial plexus, trachea, esophagus, pleura, and the lung, and related complications are avoided. Catheter-based treatment also reduces infections like local abscess, cellulitis, and osteitis. Voice loss and respiratory complications from paralysis of the recurrent laryngeal and phrenic nerves are also reduced through the delivery of specific compositions and formulations (described below) that localize the drug effects to target neurons, plexi, and ganglia with minimal drug exposure and effects to surrounding tissue.

Other sympathetic chain ganglia may similarly be accessed through the thoracic vascular bed adjacent to the target nerve sites and treated using the procedures described above. For example, catheters may be navigated and positioned in the posterior intercostal artery or vein to treat the thoracic sympathetic chain ganglia, thoracic sympathetic nerves, and nerve fibers, as shown in FIGS. 2A-2C.

Methods of Access—ICNS:

In another embodiment, target nerve tissue in the myocardium, epicardial fat pads, and ganglionated plexi may be treated by chemo neuromodulation of the ICNS by injecting the drug formulations locally at or near the heterogeneous (arrhythmic myocardial) substrate regions of the heart. The catheter may be introduced under fluoroscopy through the femoral, brachial, or radial arteries and advanced to any of the arteries supplying the heart and surrounding the heart (via the aorta) using standard endovascular or interventional techniques used by cardiologists, radiologists, and peripheral vascular physicians. The catheter may be positioned in the vessel or at the junction (intersection or bifurcation)

between two vessels. Vessel locations include the left anterior descending (LAD) artery and its branches, the right coronary artery (RCA) and its branches, the left circumflex artery (LCx) and its branches, and pulmonary veins and their bifurcations. An angiogram may be performed to confirm the position of the catheter near the target site after the anchoring element is activated. The injection element may be activated and verified that it can administer drug into the epicardial surface of the myocardium. A small volume of drug formulation may be injected to affect the intrinsic cardiac nerves in the myocardium to treat the medical condition. High frequency stimulation (HFS) or similar electrophysiology (EP) mapping techniques may be used to identify the arrhythmic regions of the cardiac substrate before and after treatment.

In another embodiment, the venous system may be used to access the heart at its vasculature for local neuromodulation of the ICNS. Catheters may be introduced through the femoral, radial, or brachial vein to reach the heart through the venacava. The catheter may be positioned in the vessel or at the junction (intersection or bifurcation) between two vessels. The vessel locations include the great cardiac vein and its branches, the middle cardiac vein and its branches, the small cardiac vein and its branches, the anterior cardiac veins and its branches, coronary sinus, and pulmonary arteries and their bifurcations. An angiogram may be performed to confirm the position of the catheter at the target nerve site after the anchoring element is activated. The injection element may be activated and verified that it can administer drug into the epicardial surface of the myocardium. The drug formulation may be injected locally at or near the intrinsic cardiac nerves in the myocardium to treat the medical condition.

Other vascular access sites (like, carotid artery or jugular vein, etc.) may also be used to introduce the catheter and advance it to the target nerve site for treatment.

In another embodiment, the drug may be administered into the myocardium from the endocardial surface of the heart. The catheter may be advanced into the right or left atria or ventricles from the arterial or venous side. HFS and other EP mapping techniques may be used to identify the arrhythmic regions of the cardiac substrate. The catheter may be positioned near the myocardial regions with heterogeneous innervation and the drug formulation may be injected locally to affect the intrinsic cardiac nerves and treat arrhythmias. HFS may be used to verify the efficacy of treatment and additional injections may be done to completely treat the disease.

In another embodiment, the drug may be administered to extrinsic and intrinsic cardiac nerves innervating the epicardial surface of the heart. Drug formulations may be injected into the pericardial sac to neuromodulate the cardiac nerves in the pericardium and the epicardium. Drugs may injected into the pericardium through any of the vascular methods described above. Drug formulations may also be injected into the pericardium using non-vascular techniques, i.e., thoracoscopically (by making an incision between the ribs) using an endoscope Surgical Access:

When minimally-invasive and endovascular methods to reach the stellate ganglion or the sympathetic chain ganglia are not feasible, the target nerve may be accessed directly through surgery and formulations described in the present invention may be injected locally. Open thoracotomy, including anterior transthoracic and axillary approaches, may be used to expose and treat the sympathetic chain. Thoracoscopic sympathectomy may also be used to treat the sympathetic chain ganglia. Minimally invasive surgical methods, using the supraclavicular and the transaxillary approaches may also be used.

Methods of Clinical Diagnosis, Screening, and Treatment

Medical conditions described above have multiple pathological origins. Treatments, methods, devices and formulations are described to treat medical conditions mediated by an overactive ANS. Also described are methods to measure ANS activity and screen and qualify patients that can benefit from the treatment. Also described are methods to monitor ANS activity during and after treatment to monitor the efficacy of treatment.

Direct measurement and stimulation of the target nerve signals may be done using a needle with sensors or a microneedle element of a catheter used to inject a drug. They may be used to measure nerve signals during and after drug injection to monitor the efficacy of treatment. The needles may be connected to electrical signal generators to stimulate the nerves before, during, and after drug injection to monitor treatment efficacy.

Other methods may be used to measure and monitor nerve signals before, during, and after treatment. These may include cardiac or other organ-related EKG/ECG changes on the skin, which may be monitored to verify the efficacy of local neuromodulation treatment. Changes in QRS, RR and QT interval, APD, EAD, ARI, and DAD may be monitored to test the efficacy of treatment. For example, stellate ganglion treatments may generate an increase in QT interval and decrease in RR interval and may be detected using a 12-lead ECG.

Thoracic skin nerve activity (TSNA) may be used to estimate the nerve activity of the stellate ganglion. The skin of the upper thorax is innervated by sympathetic nerve fibers originating from the stellate ganglion and is easily accessible. Changes in skin blood flow (using a laser Doppler flowmeter), skin temperature, and skin conductance ('sympathogalvanic reflex') may be measured with changes in ANS and stellate ganglion nerve activity. The rise in skin temperature in the hand (index finger) may be used to monitor treatment of the stellate ganglion and other ganglia of the sympathetic chain. An increase and difference in skin temperature of 1.5-2.0 degrees centigrade, between the treated and untreated side, may be a good predictor for hyperhidrosis treatment.

Imaging and nerve stimulation and imaging may be used to verify the innervated regions of the nerves, ganglia, and nerve fibers targeted for treatment. They may also be used to verify the efficacy of treatment by imaging and/or stimulation after drug injection to the target site. For example, completeness of cardiac denervation may be confirmed at surgery by direct electrical stimulation of the left and right ansae subclaviae (10 Hz, 5 msec, 5-7 V) and the left and right thoracic vagi (20 Hz, 5 msec, 5-7 V). The absence of a change in heart rate and/or heart rhythm with electrical stimulation of the cardiac nerves, at the time of surgery, confirms total denervation. Other techniques are described below.

Baroreflex sensitivity (BRS) is a powerful tool for risk stratification of patients before and after MI. The vagal parasympathetic nerve of the baroreflex transports burst-like patterns to the heart, while the sympathetic limb inhibits the response. Baroreflex efferent nerves connect to the sinoatrial node and control heart rate and heart rate variability (HRV). Occurrence of VF is inversely related to BRS. A weak baroflex causes frequent arrhythmias in patients and BRS<3 milliseconds/mm Hg is a strong risk factor for sudden cardiac death. BRS is measured by changes in blood pressure and heart rate to intravenous injection of phenylnephrine; vagal reflex is measured by lengthening of the RR interval. It can also be measured by blood pressure variation (BPV) from a continuous non-invasive finger arterial pressure (Finapress method). Variations of 0.1 Hz (0.04-0.15 Hz) are termed low frequency and variability around 0.25 Hz (0.15-0.4 Hz) is termed high frequency (HF). Variations in HRV translate to variations in BPV. Blood pressure variation can be continuously monitored before, during, and after drug injection to ensure that treatment is complete.

Autonomic sensitivity testing may also be used for monitoring and treat patients. Heart rate testing at rest, during exercise (treadmill testing), and recovery is a good marker of autonomic dysfunction and predictor of sudden death. Chronotropic incompetence (<80% heart rate reserve), resting tachycardia (>100 beats/minute), and reduced heart rate recovery (at 1 minute <18 beats) are good predictors of long-term mortality, MI, or stroke in type 2 diabetes patients without known coronary artery disease. Heart rate variability (HRV) analysis based on a 10-minute ECG recording in a well-controlled environment is also a good measure of autonomic function. HRV, also measured as the ratio of the HF and LF spectral components can be used to monitor sympathetic nerve overactivity and autonomic dysfunction.

Autonomic GPs in the heart may be located by rapid atrial pacing using a temporary pacemaker or high frequency stimulation (HFS) to induce firing and map the ectopic nerve conduction sites in the heart. HFS is delivered during the refractory period of the atrium and the PVs at a frequency of 20 Hz, amplitude of 20 volts, and pulse duration of 10 milliseconds for 5 seconds per each site (BC-1100; Fukuda Denshi, Tokyo); or achieved at 1000 beats/minute (output of 18V and pulse duration of 0.75 milliseconds) by placing tweezers on the left-atrial epicardium. Target sites are considered for treatment when they demonstrate a vagal reflex (prolonged RR interval and ventricular slowing) and a decrease of >20 mmHg in blood pressure.

Stimulation of the Sympathetic Ganglia and Ansae Subclaviae:

Stimulation of the left or right stellate ganglion or left or right ansae subclaviae may be performed to confirm the target nerve location for treatment. This may include placing the electrode or electrode element of the catheter at the nerve location, connecting it to an external stimulator, and measuring the cardiac EP activity in the heart. EKG, APD, EAD and DAD patterns may be analyzed to confirm the treatment site—unilateral, left or right, or bilateral. As noted above, other sympathetic chain ganglia between C7 to T5 may be involved. These ganglia may be similarly accessed, stimulated, and EP measurements made to confirm treatment location. The electrodes and electrode elements may be used to monitor EP changes during and after local administration of the drug formulation to the target nerve site to confirm treatment.

MIBG:

Cardiac sympathetic denervation of the heart substrate and its functionality may be assessed using 123-iodine metaiodobenzylguanidine (123-I MIBG) planar and single-photon emission computed tomography (SPECT) imaging. Heart to mediastinum ratios (H/M ratio) may be computed for early and late planar imaging. MIBG-SPECT defect scores may be calculated by measuring tracer uptake within tissue. MIBG-SPECT defect scores were predictive of cardiac arrhythmic events in patients indicated for ICD implantation. MIBG imaging also demonstrated that myocardial scarring and abnormalities in cardiac innervation were predictive of cardiac mortality in HF patients, independent of left ventricular ejection fraction. Global cardiac sympathetic innervation, assessed using H/M ratio, was also found to be associated with appropriate ICD therapy.

Typically, the left and right stellate ganglia widely innervate the posterior and anterior ventricular walls of the heart, respectively. MI and hypertrophy induced nerve sprouting can innervate other regions. The myocardium may be imaged using iodine-123 MIBG not only measure the extent of cardiac denervation and/or innervation but also locate the target regions of the heart that are innervated by the right or left stellate ganglion. Once this determination is made, unilateral (left or right), or bilateral stellate ganglion treatment is performed.

Positron Emission Tomography (PET) may also be used to quantify the inhomogeneities in myocardial sympathetic innervation and used to identify patients at highest risk for sudden cardiac arrest. PET imaging, assessed by 11C-meta-hydroxyephedrine (11C-HED), resting perfusion with 13N-ammonia and viability with 18F-2-deoxyglucose during a hyperinsulinemic-euglycemic clamp, and predicted mortality from sudden cardiac arrest independently of left-ventricular ejection fraction and infarct volume in ischemic cardiomyopathy patients.

Magnetic resonance imaging (MRI) may also be used to identify patients at risk for arrhythmias and sudden cardiac death. Late gadolinium enhancement and the presence and extension of myocardial scarring at cardiac MIll were associated with life-threatening ventricular arrhythmia.

One or more of these methods can be used to diagnose patients with medical conditions mediated by the ANS, treat the medical conditions using methods described, and verify the efficacy of treatment during or after the procedure.

REFERENCES

1. M P Schlaich, E Lambert, D M Kaye, Z Krozowski, D J Campbell, G Lambert, J Hastings, A Aggarwal and M D Esler, Sympathetic Augmentation in Hypertension Role of Nerve Firing, Norepinephrine Reuptake, and Angiotensin Neuromodulation, Hypertension, 2004; 43: 169-175.
2. O A Ajijola, D Yagishita, N K Reddy, K Yamakawa, M Vaseghi, A M Downs, D B Hoover, J L Ardell and K Shivkumar, Remodeling of stellate ganglion neurons after spatially targeted myocardial infarction: neuropeptide and morphologic changes, Heart Rhythm, 2015; 12(5), 1027-1035.
3. SF Fernandez and J M Canty Jr., Adrenergic and Cholinergic Plasticity in Heart Failure, Circulation Research, 2015; 116: 1639-1642.
4. K Fukuda, H Kanazawa, Y Aizawa, J L Ardell and K Shivkumar, Cardiac Innervation and Sudden Cardiac Death, Circulation Research, 2015; 116: 2005-2019.
5. C M Ripplinger, S F Noujaim, D Linz, The nervous heart, Progress in iophysics and Molecular Biology, 2016; xx: 1-11.
6. M J Shen and DP Zipes, Role of the Autonomic Nervous System in Modulating Cardiac Arrhythmias, Circulation Research, 2014; 114: 1004-1021.
7. O A Ajijola, N Lellouche, T Bourke, R Tung, S Ahn, A Mahajan and K Shivkumar, Md. PhD*, †Bilateral cardiac sympathetic denervation for the management of electrical storm, JACC, 2012; 59(1): 91-92.
8. M. Vaseghi, J Gima, C Kanaan, O A Ajijola, A Marmureanu, A Mahajan and K Shivkumar, Cardiac sympathetic denervation in patients with refractory ventricular arrhythmias or electrical storm: Intermediate and long-term follow-up, Heart Rhythm, 2014; 11: 360-366.
9. P Schwartz, M Motolese, G Pollavini, A Lotto, U Ruberti, R Trazzi, C Bartorelli, A Zanchetti and the Italian Sudden Death Group, Prevention of Sudden Cardiac Death After a First Myocardial Infarction by Pharmacologic or Surgical Antiadrenergic Interventions, J. Cardiovasc Electrophysiol, 1992; 3: 2-16.
10. C A Collura, J N Johnson, C Moir and M J Ackerman, Left cardiac sympathetic denervation for the treatment of long QT syndrome and catecholaminergic polymorphic ventricular tachycardia using video-assisted thoracic surgery, Heart Rhythm, 2009; 6: 752-59.

What is claimed is:

1. A method for treating angina in a patient, the method comprising:
   delivering a composition comprising amiodarone locally to a stellate ganglion of the patient in an amount sufficient to affect function of the stellate ganglion and alleviate one or more symptoms of angina in the patient.

2. The method of claim 1, comprising delivering the agent in a composition comprising a PEG carrier.

3. The method of claim 1, comprising delivering the agent in a composition comprising a contrast agent.

4. The method of claim 1, comprising delivering the agent in a composition comprising a hydrogel.

5. The method of claim 1, comprising delivering the agent in a composition comprising a biostable polymer.

6. The method of claim 1, comprising delivering the agent in a composition comprising a biodegradable polymer.

7. A method for treating angina in a patient, the method comprising:
   delivering a composition comprising amiodarone locally to a stellate ganglion of the patient in an amount sufficient to affect function of the stellate ganglion and alleviate one or more symptoms of angina in the patient; and
   measuring electrical signals directly transmitted from the stellate ganglion.

8. The method of claim 7, wherein the stellate ganglion is accessed via an anterior paratracheal approach.

9. The method of claim 7, comprising measuring the electrical signals transmitted from the stellate ganglion before and after delivering the agent to the stellate ganglion.

10. The method of claim 7, wherein the stellate ganglion is accessed via a supraclavicular approach.

11. The method of claim 7, wherein the stellate ganglion is accessed via an endovascular approach.

12. The method of claim 7, wherein the composition further comprises a hydrogel.

13. The method of claim 12, wherein the hydrogel comprises PEG.

14. A method for treating angina in a patient, the method comprising:
   delivering a composition comprising a dihydropyridine calcium antagonist locally to a stellate ganglion of the patient in an amount sufficient to affect function of the stellate ganglion and alleviate one or more symptoms of angina in the patient.

15. The method of claim 14, wherein the dihydropyridine calcium antagonist comprises amlodipine.

16. The method of claim 14, wherein the dihydropyridine calcium antagonist comprises nifedipine.

* * * * *

UNITED STATES PATENT AND TRADEMARK OFFICE
CERTIFICATE OF CORRECTION

| | |
|---|---|
| PATENT NO. | : 11,246,879 B2 |
| APPLICATION NO. | : 16/076308 |
| DATED | : February 15, 2022 |
| INVENTOR(S) | : Corinne Bright et al. |

It is certified that error appears in the above-identified patent and that said Letters Patent is hereby corrected as shown below:

On the Title Page

Page 3, Column 1 (Other Publications), Line 6, delete "Cardopulmonary" and insert
-- Cardiopulmonary --.

Page 4, Column 2 (Other Publications), Line 65, delete "fordrug" and insert -- for drug --.

Page 5, Column 2 (Other Publications), Line 19, delete "Hearth" and insert -- Heart --.

Page 5, Column 2 (Other Publications), Line 20, delete "denevation" and insert -- denervation --.

Page 5, Column 2 (Other Publications), Line 39, delete "Arryhtmias"" and insert -- Arrhythmias" --.

In the Specification

Column 8, Line 42, delete "CAF" and insert -- ('AF --.

Column 36, Line 11, delete "(al" and insert -- ($\alpha$1 --.

Signed and Sealed this
Seventeenth Day of May, 2022

*Katherine Kelly Vidal*

Katherine Kelly Vidal
*Director of the United States Patent and Trademark Office*